US012594239B2

(12) United States Patent
Saffie-Siebert et al.

(10) Patent No.: US 12,594,239 B2
(45) Date of Patent: Apr. 7, 2026

(54) PROTECTION OF BIOLOGICAL SPECIES FROM DEGRADATION

(71) Applicant: SISAF LTD, Guildford (GB)

(72) Inventors: Roghieh Suzanne Saffie-Siebert, Guildford (GB); Flavia Sutera, Guildford (GB)

(73) Assignee: SISAF LTD, Guildford (GB)

(*) Notice: Subject to any disclaimer, the term of this patent is extended or adjusted under 35 U.S.C. 154(b) by 276 days.

(21) Appl. No.: 18/580,570

(22) PCT Filed: Jul. 22, 2022

(86) PCT No.: PCT/GB2022/051939

§ 371 (c)(1),
(2) Date: Jan. 18, 2024

(87) PCT Pub. No.: WO2023/002224

PCT Pub. Date: Jan. 26, 2023

(65) Prior Publication Data

US 2025/0228773 A1 Jul. 17, 2025

(30) Foreign Application Priority Data

Jul. 23, 2021 (GB) ..................................... 2110645

(51) Int. Cl.

| | |
|---|---|
| ***A61K 47/54*** | (2017.01) |
| ***A61K 9/00*** | (2006.01) |
| ***A61K 9/06*** | (2006.01) |
| ***A61K 31/7105*** | (2006.01) |
| ***A61K 31/713*** | (2006.01) |
| ***A61K 39/00*** | (2006.01) |
| ***A61K 47/02*** | (2006.01) |

(52) U.S. Cl.

CPC .............. *A61K 9/06* (2013.01); *A61K 9/0019* (2013.01); *A61K 9/0053* (2013.01); *A61K 31/7105* (2013.01); *A61K 31/713* (2013.01); *A61K 47/02* (2013.01); *A61K 47/544* (2017.08); *A61K 39/00* (2013.01)

(58) Field of Classification Search

None

See application file for complete search history.

(56) References Cited

FOREIGN PATENT DOCUMENTS

| | | |
|---|---|---|
| WO | WO 2011/001456 A2 | 1/2011 |
| WO | WO 2011/012867 A1 | 2/2011 |
| WO | WO 2018/089688 A1 | 5/2018 |
| WO | WO 2020/193995 A1 | 10/2020 |
| WO | WO 2020/193996 A1 | 10/2020 |
| WO | WO 2020/193999 A1 | 10/2020 |
| WO | WO 2012/005783 A1 | 1/2021 |

OTHER PUBLICATIONS

International Search Report issued in International Application No. PCT/GB2022/051939, mailed Nov. 10, 2022.

Written Opinion of the International Searching Authority issued in International Application No. PCT/GB2022/051939, mailed Nov. 10, 2022.

International Preliminary Report on Patentability (IPRP) mailed Oct. 13, 2023 in International Application No. PCT/GB2022/051939.

GB Search Report under Section 17(5) issued in GB211064.5 mailed May 4, 2022.

Giovannini, Giorgia et al.: "Stabilizing silica nanoparticles in hydrogels: impact on storage and polydispersity",RSC Advances, vol. 7, No. 32, Jan. 1, 2017 (Jan. 1, 2017), pp. 19924-19933, XP055909604, D01: 10.1039/C7RA02427D.

Jung, Yuna et al.: "Recent advances in surface engineering of porous silicon nanomaterials for biomedical applications",Microporous and Mesoporous Materials, Elsevier, Amsterdam ,NL, vol. 310, Oct. 1, 2020 (Oct. 1, 2020), XP086323682, ISSN: 1387-1811, DOI: 10.1016/J.MICROMES0.2020.110673.

Vigata, Margaux et al.: "Hydrogels as Drug Delivery Systems: A Review of Current Characterization and Evaluation Techniques", Pharmaceutics, vol. 12, No. 12, Dec. 7, 2020 (Dec. 7, 2020), p. 1188, XP055909598, DOI: 10.3390/pharmaceutics12121188.

Li, Wei et al.: "Hierarchical structured and programmed vehicles deliver drugs locally to inflamed sites of intestine", Biomaterials, vol. 185, Dec. 1, 2018 (Dec. 1, 2018), pp. 322-332, XP55910113, Amsterdam, NL ISSN: 0142-9612, DOI: 10.1016/j.biomaterials.2018.09.024.

Rocha-Garcia Denisse et al.: "Gelatin-based porous silicon hydrogel composites for the controlled release of tramadol", European Polymer Journal, vol. 108, Nov. 1, 2018 (Nov. 1, 2018), pp. 485-497, XP055910209, GB ISSN: 0014-3057, DOI: 10.1016/j.eurpolymj.2018.09.033.

ZHANG Zipei et al.: "Designing hydrogel particles for controlled or targeted release of lipophilic bioactive agents in the gastrointestinal tract", European Polymer Journal, vol. 72, Nov. 1, 2015 (Nov. 1, 2015), pp. 698-716, XP055909601,GB ISSN: 0014-3057, DOI: 10.1016/j.eurpolymj. 2015.01.013.

(Continued)

*Primary Examiner* — Robert A Wax

(74) *Attorney, Agent, or Firm* — Marian E. Fundytus; Amster Rothstein & Ebenstein LLP

(57) ABSTRACT

A method of preparing an injectable or oral storage stable formulation, comprising: contacting a biological species with a delivery system comprising biocompatible solid particles to form a complex; then optionally, lyophilising the complex to form a powder, and then dispersing the complex in a biodegradable gel material to form the formulation, comprising the complex embedded in the biodegradable gel material. Also related products, methods, and medical uses.

23 Claims, 32 Drawing Sheets

(56) References Cited

OTHER PUBLICATIONS

Bovone, Giovanni et al. "Engineering Hydrogel Adhesion for Biomedical Applications via Chemical Design of the Junction", ACS Biomater. Sci. Eng., 7, Apr. 2021, pp. 4048-4076.
NIST—NCL Joint Assay Protocol, PCC-X, version 1.1, "Measuring the size of nanoparticles using TEM", revised Feb. 2010, https://tsapps.nist.gov/publication/get_pdf.cfm?pub_id=854083.

M: DNA ladder 1: Naked mRNA 2: 1- KTTKS-BC -mRNA 3: Naked siRNA 4: 1- KTTKS-BC -siRNA 5: 1-KTTKS-BC 9: SIS0012 10: SIS0013

PROTECTION OF BIOLOGICAL SPECIES FROM DEGRADATION

CROSS REFERENCE TO RELATED APPLICATIONS

The present application is a § 371 National Phase application based on PCT/GB2022/051939, filed on Jul. 22, 2022, which claims the benefit of GB application No. 2110645.5 filed Jul. 23, 2021 the subject matter of each of which is incorporated by reference in their entirety.

FIELD OF INVENTION

The invention relates to methods and compositions (particularly injectable or oral compositions) for protecting biological species (such as nucleic acids, antigens and vaccines) from degradation. Such methods and compositions are especially useful in, although not limited to, the field of pharmaceuticals.

BACKGROUND

There is a need for improvements in excipients for biologically active agents, particularly in the field of injectable or oral formulations. The provision of suitable excipients is required for advances in biomedical research to be fully translated into effective, safe and cost-effective treatments. In particular there is a need to stabilise biological species to reduce degradation during storage. There is also a need for biocompatible excipients for oral or injectable compositions, which enable oral administration or administration by injection without intervening steps of (i) extraction of the active biological species from the compositions and (ii) reformulation.

Biological species, such as nucleic acids, antigens and vaccines, can be effective agents for use in the treatment or prophylaxis of various medical conditions. However, unlike small chemical entities, biological species can be difficult to store, often requiring storage at low (e.g. −20° C.) or ultra low (e.g. −70° C.) temperatures. This makes many pharmaceutical products comprising biological species difficult to store and transport to patients, especially in less developed countries.

One reason for the instability of pharmaceutical products comprising biological species is that manufacturing processes for biological species, especially those containing nucleic acids such as mRNA, pDNA, saRNA, shRNA and siRNA, result in residues of enzymes being present in the product. For example, use of a microbial fermentation expression system to produce a biological species results in a crude product containing enzymatic residues, which are difficult to remove completely. Even with substantial amounts of downstream processing, some low level contaminants that have potential to degrade the biological species remain. mRNA in particular is vulnerable to enzymatic and chemical degradation. Enzymatic activity may be slowed by low temperature and/or by lyophilisation of the biological species, but each of those solutions come with disadvantages. Furthermore, even if the biological species can be rendered storage stable by low temperature or the removal of water from the storage medium, instability of the products obtained on conversion of the stored formulation into a dosage form suitable for administration remains an issue. On reconstitution of a lyophilised formulation or thawing of a frozen dosage form, enzymatic residue contaminants that were dormant on storage are reactivated leading to reduced shelf life of the final dosage form. In addition the presence of water and free radicals in biological systems such as mRNA-lipid nanoparticle vaccines, can result in hydrolysis or phosphate clipping of the phosphate backbone rendering the nucleic acid unreadable.

A number of mRNA vaccines against SARS-CoV-2, including the Pfizer BioNTech vaccine BNT162b2 ("Comirnaty") and the Moderna CX-024414 vaccine, require cold-chain storage and transport. This limits accessibility to the vaccine for low-income countries and adds cost and logistical complexity in all markets. The cold chain requirement also limits the volumes of vaccines that can be manufactured, stored and transported thus restricting supply of vaccines hindering their effective roll out in a short time-frame, which can often be crucial to curtailing the spread of infections. It would be advantageous if vaccines could be stored and transported at standard refrigerator temperature (about −5° C.) or room temperature (about 20° C.). It would also be of benefit if vaccines could tolerate higher temperatures (for example, 30, 40 or 50° C.) for storage, or at the very least in the short-term for transport and distribution purposes.

Maintaining RNA stability in an injectable composition, for example a vaccine composition, by means of low temperatures, as well as bringing logistical challenges, also has the technical limitation that the RNA must be defrosted before injection, and that after injection it must remain stable in the body for long enough to show sufficient biological activity. This may require stability to be maintained during translocation around the body and/or escape from the endosomal compartment. Stability in vivo must also be maintained for long enough for sufficient translation into protein to take place and/or for transportation to the location in the body where translation into protein occurs.

There is a need for formulations capable of stabilising biological species, such as mRNA vaccines, allowing long term storage at standard fridge temperature, room temperature or above. Likewise there is a need to stabilise formulations for delivery of biological material to cell in vivo such that the biological species payload is only released on internalisation into the desired cell. Formulations that stabilise biological species ideally comprise solely pharmaceutically acceptable excipients, to allow the formulation to be administered (particularly, administered orally or by injection) without the need to extract the active biological species from the formulation and then reformulate. For example, the formulation used to stabilise a biological species advantageously is able to be administered (particularly, administered orally or by injection) directly; or administered (particularly, administered orally or by injection) after addition of further agents or excipients, for example on dilution with a solvent, or following simple reconstitution steps.

Gel materials, especially hydrogels, have previously been used as adhesives in various biomedical applications. For example, hydrogels are used to seal wounds in tissues and organs, to adhere bioelectronics to the body or to bond drug delivery devices, such as patches, to the skin. A number of biocompatible and biodegradable hydrogels have been developed for such purposes as described by Bovone et al. in *ACS Biomater. Sci. Eng.* April 2021, "*Engineering Hydrogel Adhesion for Biomedical Applications via Chemical Design of the Junction*". However, the use of biocompatible gels, particularly in injectable or oral formulations, to stabilise biological species complexed with biocompatible solid particles, has not previously been suggested.

BRIEF DESCRIPTION OF INVENTION

The present invention is based on an appreciation that if biological species are contacted with a delivery system comprising biocompatible solid particles to form a complex, and then the complex is embedded in a biodegradable gel material, degradation of the delivery system and hence the biological species can be arrested or at least slowed; particularly where the particles comprise hydrolysable silicon. Thus, embedding said complex in said biodegradable gel material can be used to stabilise the complex. A stabilised complex is better able to protect the biological species contained therein from degradation on storage or in vivo.

Furthermore, the delivery system may function as a biocompatible excipient for oral or injectable administration of the biological species, which enables said oral administration or administration by injection without intervening steps of (i) extraction of the active biological species from the compositions and (ii) reformulation.

According to a first aspect of the invention, therefore, there is provided a method of preparing formulation, advantageously a oral or injectable formulation, and advantageously a storage stable formulation, the method comprising (i) contacting a biological species with a delivery system comprising biocompatible solid particles to form a complex; then (ii) optionally, lyophilising the complex to form a powder; and then (iii) dispersing the complex in a biodegradable gel material, to form the formulation, comprising the complex embedded in the biodegradable gel material.

According to a second aspect of the invention, there is provided a method of protecting a biological species from degradation, comprising (i) contacting the biological species with a delivery system comprising biocompatible solid particles to form a complex; then (ii) optionally, lyophilising the complex to form a powder; and then (iii) dispersing the complex in a biodegradable gel material to form a formulation, advantageously an oral or injectable formulation, comprising the complex embedded in the biodegradable gel material.

The method of the second aspect of the invention may further comprise the steps of (iv) optionally, storing the formulation; and then (v) preparing a medicament for administration, preferably oral administration or administration by injection, from the formulation; preferably, without any intervening steps of extraction of the active biological species from the compositions and reformulation. Thus, in preferred embodiments, the step (v) of preparing the medicament does not include any extraction steps, such that the medicament comprises all the constituents of the formulation. Therefore the preparation step may, for example, simply be or comprise a dilution step and/or a reconstitution step.

According to a third aspect of the invention, there is a provided a formulation, preferably an oral or injectable formulation, comprising a biodegradable gel matrix in which is embedded a biological species complexed to a delivery system comprising solid biocompatible particles. The formulation of the third aspect of the invention is advantageously a storage stable formulation. The formulation of the third aspect of the invention advantageously comprises a lipid component comprising a cationic lipid and/or an ionisable lipid; and, optionally, a non-reducing disaccharide.

The formulation (preferably, oral or injectable formulation) of the third aspect of the invention may be prepared in accordance with the first aspect of the invention. The formulation of the third aspect of the invention is typically a gel or a solid. The formulation of the third aspect of the invention may be a pharmaceutical composition suitable for direct administration. For example, the formulation may be administered topically e.g. a gel for administration to the skin or a membrane or surface of the body, or the formulation may be a solid oral dosage form, or an injectable dosage form (e.g. an injectable solution). Alternatively, the formulation of the third aspect of the invention may be suitable for converting to a pharmaceutical composition for administration, particularly oral administration or administration by injection, in a preparation step. For example, the formulation may be reconstituted and/or diluted to provide an injectable solution, reformulated as a lotion or ointment, reformulated into an oral dosage form, or included as the active component of a transdermal delivery patch that has a multiplicity of microneedles for injection of a composition through one or more skin layers. Advantageously, the entire formulation of the third aspect of the invention may be suitable for converting to a pharmaceutical composition for administration, without any constituents of the formulation needing to be extracted other than the optional removal of solvents such as water, e.g. in an evaporation step or a freeze-drying step. Additional ingredients may be added to the formulation on conversion to a pharmaceutical composition, e.g. pharmaceutical acceptable excipients, diluents and adjuvants. Thus, the formulation of the third aspect of the invention and medicaments prepared from it meet the need for biocompatible excipients, particularly for oral or injectable compositions, which enable administration, particularly oral administration or administration by injection, without an intervening step of extraction of active biological species from the compositions and without an intervening step of reformulation. This may particularly be the case where the biocompatible solid particles comprise hydrolysable silicon.

According to a fourth aspect of the invention, there is provided a method of preparing a medicament comprising a biological species for administration, advantageously oral administration or administration by injection, the method comprising: either preparing a formulation in accordance with the method of the first aspect of the invention, or providing a formulation in accordance with the third aspect of the invention; then (ii) optionally storing the formulation; and then (iii) preparing a medicament comprising the biological species for administration preferably oral administration or administration by injection, such as a dilution and/or reconstitution step.

As such, the method of the fourth aspect of the invention, when comprising preparing a formulation in accordance with the method of the first aspect of the invention, may comprise: contacting the biological species with a delivery system comprising a solid biocompatible particle to form a complex; then, optionally, lyophilising the complex to form a powder; then dispersing the complex in a biodegradable gel material to form a formulation; then optionally storing the formulation; and then preparing a medicament comprising the biological species and delivery system for administration, preferably oral administration or administration by injection.

Alternatively, the method of the fourth aspect of the invention, when comprising providing a formulation in accordance with the third aspect of the invention, may comprise providing a formulation, preferably an oral or injectable formulation, comprising biological species complexed to a delivery system comprising biocompatible solid particles embedded in a biodegradable gel matrix; and then preparing a medicament comprising the biological species and delivery system for administration, preferably oral administration or administration by injection.

The step of preparing the medicament for administration may, for example, be a step of preparing the medicament for administration by injection, such as a step in which the biodegradable gel material containing the dispersed biological species and delivery system is diluted and/or reconstituted; or in another example, it may be a step of preparing the medicament for oral administration, for example, by tableting with pharmaceutically acceptable excipients, such as fillers, disintegrants, etc.

According to a fifth aspect of the invention, there is provided a method of treating or preventing a disease or disorder, the method comprising administering, preferably orally or by injection, the medicament of the fourth aspect of the invention to a subject in need thereof, for example by subcutaneous or intramuscular injection.

As such, the method of the fifth aspect of the invention may comprise: contacting a biological species with a delivery system comprising biocompatible solid particles to form a complex; then, optionally, lyophilising the complex to form a powder; then dispersing the complex in a biodegradable gel material to form a formulation, preferably an oral or injectable formulation; then, optionally, storing the formulation; then preparing a medicament comprising the biological species and delivery system for administration, preferably oral administration or administration by injection; and then administering the medicament, preferably orally or by injection, to a subject in need thereof.

Alternatively, the method of the fifth aspect of the invention may comprise providing a formulation, preferably an oral or injectable formulation, comprising a biodegradable gel material in which is embedded a biological species complexed to a delivery system comprising biocompatible solid particles; then preparing a medicament comprising the biological species and delivery system for administration, preferably orally or by injection, such as a step in which the biodegradable gel material containing the embedded biological species and delivery system is diluted and/or reconstituted; and then administering the medicament, preferably orally or by injection, to a subject in need thereof. The step of preparing the medicament for administration, preferably orally or by injection may, for example, be or comprise a step in which the biodegradable gel material containing the embedded biological species and delivery system is diluted and/or reconstituted; or, in another example, may be or comprise a step of preparing the medicament for oral administration, for example by tableting with pharmaceutically acceptable excipients, such as fillers, disintegrants etc. The step of administering the medicament may, for example, be a step of subcutaneous or intramuscular administration by injection, or oral administration of a solid dosage form.

Preferably, the method of preparing a medicament of the fourth aspect of the invention, and/or the method of treating or preventing a disease or disorder of the fifth aspect of the invention, does not or do not include any extraction steps; such that the medicament for administration, preferably oral administration or administration by injection, includes all constituents of the (preferably oral or injectable) formulation produced in the method of the first aspect of the invention, or the (preferably oral or injectable) formulation of the third aspect of the invention. A method (of the fourth or fifth aspect of the invention) that does not include extraction steps may include steps to remove solvents, such as water, from the (preferably oral or injectable) formulation produced in the method of the first aspect of the invention or the (preferably oral or injectable) formulation of the third aspect of the invention, e.g. an evaporation step, freeze drying or filtration step.

In a sixth aspect, the invention provides a (preferably oral or injectable) medicament. The medicament may comprise a biological species complexed with a delivery system embedded in a biodegradable gel material. Alternatively, the medicament may comprise a biological species complexed with a delivery system, together with compounds capable of forming the matrix of a biodegradable gel dispersed in a carrier system, which may be a liquid carrier system, such as an aqueous solution, or a solid carrier system. The medicament may, for example, be of an injectable dosage form, comprising a biological species complexed with a delivery system together with compounds capable of forming the matrix of a biodegradable gel dispersed in a liquid carrier system. Alternatively, the medicament may, for example, be a solid or gel dosage form, comprising the biological species complexed with the delivery system, together embedded in a biodegradable gel, for example, for oral administration.

In the methods of the first, second, fourth and fifth aspects of the invention, following the step of contacting the biological species with a delivery system, the biological species in contact with the delivery system is optionally lyophilised in a lyophilisation step to form a powder. It has been found that lyophilisation can be advantageous in increasing the stability of the formulation, for example during optional storage of the formulation.

The biological species is optionally, or optionally comprises, one or more of a nucleic acid, antigen and vaccine. The biological species typically comprises a nucleic acid, especially siRNA or mRNA or plasmid DNA. When the biological species is a vaccine, the method of preventing a disease or disorder of the fifth aspect of the invention may be a method of vaccination.

The delivery system of the first to sixth aspects of the invention is a particulate delivery system comprising biocompatible (and, optionally, biodegradable) solid particles. The delivery system comprising biocompatible particles advantageously comprises particles of hydrolysable silicon. The delivery system may, for example, comprise biocompatible particles of hydrolysable silicon, in the presence of a lipid component comprising at least one lipid, (such as a cationic or ionisable lipid) and optionally a non-reducing disaccharide (such as trehalose).

Thus, the method of the first aspect of the invention, or the method of the second aspect of the invention (and, consequently, the method of the fourth aspect of the invention or the method of the fifth aspect of the invention) may comprise contacting a biological species comprising a nucleic acid with a delivery system comprising biocompatible particles of hydrolysable silicon, in the presence of at least one lipid, such as a cationic or ionisable lipid, and optionally a non-reducing disaccharide such as trehalose; then, optionally, lyophilising the biological species in contact with the delivery system to form a powder; and then embedding the combined biological species and delivery system in a biodegradable gel material. The formulation of the third aspect of the invention and/or the medicament of the sixth aspect of the invention may comprise a biological species comprising a nucleic acid complexed to particles comprising hydrolysable silicon, at least one lipid, such as a cationic or ionisable lipid, and optionally a non-reducing disaccharide such as trehalose, embedded in a biodegradable gel material.

The biological species, or one or more constituents thereof, contacted with the delivery system, may function as a vector for delivery of the biological species, or one or more other constituents thereof, to a cell, e.g. as a transfection vector or other vector that can be internalized and allow endosomal escape to deliver the biological species to the cytoplasm. The transfection vector may be used to target the biological species to a cell. The biological species may therefore include a nucleic acid for transcription within a cell, together with other constituents providing a transfection vector, especially a non-viral transfection vector, or a vector that allows uptake by immune cells, leading to endosomal escape of the nucleic acid for release into the cytoplasm.

The (preferably oral or injectable) formulation produced in accordance with the method of the first or second aspect of the invention, or provided by the third aspect of the invention, advantageously can be stored at a relatively high temperature (e.g. −10° C. or higher, especially 4° C. or higher) for a substantial period (e.g. 6 weeks or longer), without substantial degradation occurring, e.g. without 10% or more (such as without 8, 7, 6, 5, 4, 3, 2 or 1% or more) of the biological species being degraded. Furthermore, when the (preferably oral or injectable) formulation of the third aspect of the invention is prepared as a medicament for administration, for example in accordance with the method of the fourth aspect of the invention, the biological species present in the medicament advantageously remains protected from degradation, for example, compared to conventional reconstituted or thawed pharmaceutical products comprising biological species.

When in a solid structure, the movement of molecules is restricted and their normal resonance amplitude is reduced. It is postulated that when a composition comprising a biological species and trace levels of contaminants, such as enzymes (e.g. residual enzymatic species from manufacturing processes for biological species), are bound into a matrix structure, the contaminants in the system (e.g. enzymes) do not have sufficient movement to act on the biological species and cause degradation. For example, enzymes (e.g. residual enzymatic species) do not have sufficient freedom of movement to bind to the correct part of a nucleic acid or other biological species and will not have the ability to effect the enzyme cleavage. Similarly, without wishing to be bound by theory, it is thought that there may be a reduction in the number of water molecules available for enzyme-catalysed reactions with the biological species, for example water molecules may be removed by reaction of water with hydrolysable silicon.

Thus, the embedding of a complex of the biological species with a delivery system comprising particles of biocompatible solid material within a biocompatible gel has been found to stabilise the complex, preserving the constituents of the complex both on storage and in vivo following administration to the human body.

Contact of the biological species with a delivery system comprising particles of biocompatible solid material, especially hydrolysable silicon, has been found to be particularly effective in preventing degradation of the biological species. It is postulated that biological species, such as one or more nucleic acids, are bound on the surface of the porous silicon, protecting the cleavage sites of the nucleic acid, such as sites on the phosphate backbone, from enzymatic degradation.

It is believed that there are three primary factors for overall product stability on storage: prevention of degradation of the biological species, e.g. RNA; slowing of oxidation of lipids, e.g. those involved in transfection; and colloidal stability of a particulate suspension preventing aggregation of particles. The formulation and medicament of the present invention advantageously provide some or all of those three factors. In addition, following administration, preferably oral administration or administration by injection, it is believed that the complex of biological species with a delivery system may continue to be stabilised in vivo by the presence of the gel until it has fully degraded. This enhanced biological stability may assist in increasing the prospect that the biological species is delivered to the desire location, for example, internalised by target cells.

DETAILED DESCRIPTION

Figure 1:
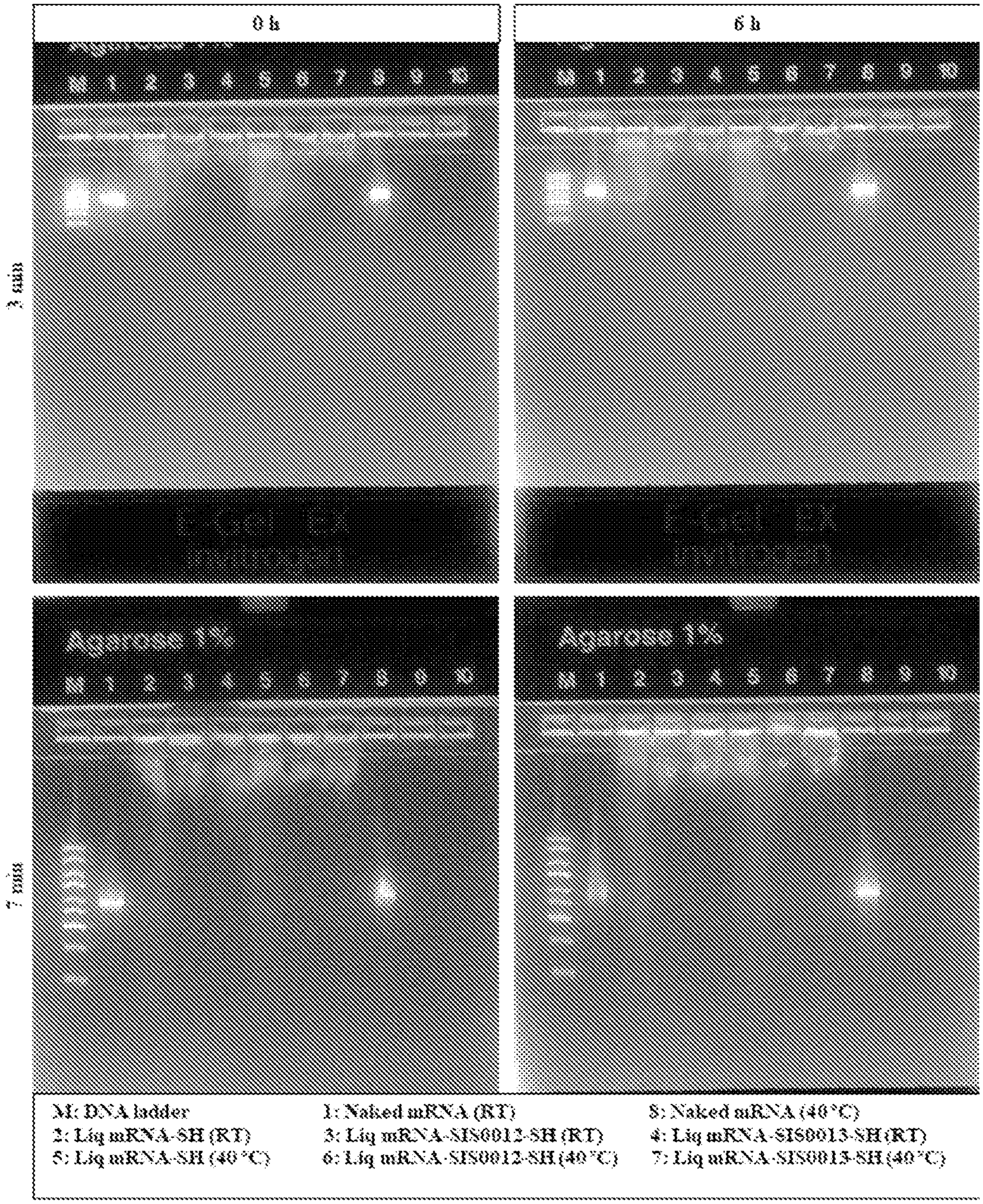
FIG. 1 Gel electrophoresis images of liquid mRNA-Biocourier formulations embedded in sodium hyaluronate biodegradable gels at the time of preparation and 6 h after storage at room temperature (RT) or 40° C.

Without wishing to be bound by any theory, the inventors have come to the realisation that the complexing of a nucleic acid or other biological species to a solid biocompatible particle, such as hydrolysable silicon, restricts the mobility (molecular motion) not only of the biological species but also of positively charged components which may be present in a composition such as lipids, polymers and peptides used to form a lipid membrane. This stabilises their positive charge which in turn enables them to retain their function in stabilising the biological species. It is believed that modified and derivatised silicon particles stabilise not only the biological species but also the integrity of the positively charge components, by preserving their positive charge and preventing dissociation of the biological species and positive charge component. Unlike liposomes that are the result of an oil/water/surfactant interaction or lipid nanoparticles, which are believed to still contain some pockets of water within the lipid nanoparticles, and therefore expose a biological species to an aqueous environment, no or little moisture is advantageously present in the complex of the invention. Therefore there is no solvent/aqueous environment for enzymes or free-radicals to operate in. This dual action of silicon binding and reduction in local water availability could also be a reason why it increases the stability of the biological species when stored at room temperature.

Building on that realisation, the inventors have investigated the effect of the entrapment of the entire complex in a matrix system (of a biodegradable gel material) to further protect and immobilise the constituents of the complex. Physical protection of biological species such as nucleic acids from the environment is provided by a combination of encapsulation by a lipid layer and adsorption onto a solid support (e.g., a particle comprising hydrolysable silicon) in the complex of the invention and via the entrapment of the entire complex in a matrix system (of a biodegradable gel material). This provides a high level of protection from degradation, by avoiding interactions with outside species. While adsorption or encapsulation alone can restrict some of these interactions, such as access of enzymes and microorganisms, contact with environmental moisture, and the mobility of the biological species, inclusion in a matrix system (of a biodegradable gel material) has been found to be highly advantageous in preventing interactions during long term storage under mild conditions. The effectiveness of a gel, a material that necessarily includes a substantial amount of liquid, typically water, to swell a polymeric matrix, to stabilise the complex is surprising, it having previously been supposed that the presence of liquid would destabilise the complex and/or lead to degradation of the biological species or other constituents. Thus, gels have not previously been widely used for the protection of active pharmaceutical ingredients particularly in oral or injectable formulations, nor to promote storage stability, but more for applications such as tissue binding or topical applications.

A further advantage of the (preferably oral or injectable) formulations of the present invention (e.g. those of the third aspect of the invention) is that they are ready to convert to a medicament for administration, particularly oral administration or administration by injection (e.g. medicaments of the sixth aspect of the invention) without any extraction steps. Thus the formulations may, for example, be being ready to dilute and inject without an extraction step; or to make into a solid oral dosage form without an extraction step. Thus, the formulations meet a need for biocompatible excipients, particularly for oral or injectable compositions, which enable administration, particularly oral administration or administration by injection, without intervening steps of extraction of the active biological species from the compositions and reformulation. Without wishing to be bound by any theory, it is thought that this may be the case because the solid particles of the delivery system of the invention are biocompatible. Thus, it may particularly be the case where the particles comprise hydrolysable silicon. In contrast, for example, silica particles administered orally or by injection are not biocompatible thus may cause inflammation.

Oral or Injectable Formulations and Medicaments

The methods, formulations and medicaments of the first to sixth aspects of the invention preferably are, or preferably result in, an oral or injectable product. Gels, such as those present in the formulations and medicaments of the third or sixth aspect of the invention, have not previously been widely used for the protection of biological species in oral or injectable formulations (nor to promote storage stability) but more for applications such as tissue binding, or topical applications such as in cosmetics or the treatment of burns.

For example, advantageously, the entire formulation of the third aspect of the invention may be suitable for converting to a pharmaceutical composition for administration, without any constituents of the formulation needing to be extracted; other than the optional removal of solvents such as water, e.g. in an evaporation step or a freeze-drying step. It will also be appreciated that additional ingredients may be added to the formulation on conversion to a pharmaceutical composition, e.g. additional pharmaceutically acceptable excipients, diluents and adjuvants; still without extraction and/or reformulation steps.

Thus, the formulation of the third aspect of the invention and medicaments prepared from it meet the need for biocompatible excipients for oral or injectable compositions, which enable oral administration or administration by injection without an intervening step of extraction of active biological species from the compositions and without an intervening step of reformulation. This may particularly be the case where the biocompatible solid particles comprise hydrolysable silicon.

Accordingly, in preferred embodiments, the formulation is an injectable formulation and the medicament is an injectable medicament. The mode of injection may be is subcutaneous or intradermal (e.g. by a transdermal patch comprising microneedles); intramuscular; or intravenous. Thus, provided herein is an injection device, comprising a formulation of the third aspect of the invention, or a medicament prepared from a formulation of the third aspect of the invention. The injection device may be or comprise a syringe comprising a plunger, cartridge (also known as a barrel) and needle. The cartridge of the syringe may contain the formulation of the third aspect of the invention, or a medicament prepared from it. The cartridge may contain a single dose, or multiple doses, for example 1, 2, 3, 4 or 5 doses, of said formulation or medicament. The syringe may be or comprise a safety syringe. The syringe may be or comprise a disposable syringe. The syringe may be or comprise a hypodermic syringe. The injection device may be or comprise an auto injector system, such as a system that is or includes an injection pen. The injection device may be or comprise a needleless injector. The injection device may be or comprise a transdermal delivery device, such as a delivery patch equipped with a multiplicity of microneedles for injection. The injection device may be or comprise an autoinjector. The injection device may be or comprise an infusion pump device. In all its embodiments, the injection device comprises a formulation of the third aspect of the invention, or a medicament prepared from a formulation of the third aspect of the invention.

Also provided herein is an oral dosage form, comprising a formulation of the third aspect of the invention, or a medicament prepared from a formulation of the third aspect of the invention. The oral dosage form may comprise one or more physiologically compatible carriers and/or excipients and may be in solid (e.g. tablet, capsule or powder) or liquid (e.g. solution) form. Tablets and capsules may be prepared with binding agents, for example, syrup, acacia, gelatin, sorbitol, tragacanth, or poly-vinylpyrrolidone; fillers, such as lactose, sucrose, corn starch, calcium phosphate, sorbitol, or glycine; lubricants, such as magnesium stearate, talc, polyethylene glycol, or silica; and surfactants, such as sodium lauryl sulfate. A liquid composition may contain conventional additives such as suspending agents, for example sorbitol syrup, methyl cellulose, sugar syrup, gelatin, carboxymethyl-cellulose, or edible fats; emulsifying agents such as lecithin, or acacia; vegetable oils such as almond oil, coconut oil, cod liver oil, or peanut oil; preservatives such as butylated hydroxyanisole (BHA) and butylated hydroxytoluene (BHT). The oral dosage form may be or comprise a liquid composition which may be encapsulated in, for example, gelatin, to provide a unit dosage form. The solid oral dosage form may include tablets, two-piece hard shell capsules and soft elastic gelatin (SEG) capsules. The solid oral dosage form may be or comprise a dry shell formulation, which typically comprises about 40% to 60% concentration of gelatin, about a 20% to 30% concentration of plasticizer (such as glycerin, sorbitol or propylene glycol) and about a 30% to 40% concentration of water. Other materials such as preservatives, dyes, opacifiers and flavours also may be present. The liquid fill material may comprise a solid form of the formulation or medicament, which has been dissolved, solubilized or dispersed (with suspending agents such as beeswax, hydrogenated castor oil or polyethylene glycol 4000) or a liquid form of the formulation or medicament, in vehicles or combinations of vehicles such as mineral oil, vegetable oils, triglycerides, glycols, polyols and surface-active agents.

Extraction Step

Advantageously in the method of the fourth aspect of the invention, preparing the medicament for administration does not include any extraction steps, such that the medicament comprises all the constituents of the formulation. As used herein, the term "extraction step" may refer to removing a biological species from a composition comprising said species. Removal steps may include one or more of physical separation (such as centrifugation and/or filtration) and chemical separation (such as dissolving the species in a solvent in which other components of the composition are poorly soluble and/or dissolving said other components in one or more solvents in which the species is poorly soluble; this may be followed by physical separation, such as filtration mentioned above, and/or evaporation, such as rotary evaporation). When the biological species is unstable under the conditions of extraction, which may particularly be the case where the biological species is or comprises a nucleic acid, such as mRNA, extraction may risk decomposition of the biological species. Further, the term "reformulation" or "reformulate" as used herein may refer to adding one or more excipients to a biological species after it has been extracted from a previous composition.

Advantageously, as described herein, formulations and medicaments are provided in all aspects of the invention, which do away with extraction and reformulation steps, or alternatively do away with extraction steps only.

Delivery System

The delivery system of the first to sixth aspects of the invention typically comprises particles of biocompatible material, for example particles of hydrolysable silicon, together with a lipid component, typically comprising at least one cationic lipid or ionizable lipid, and optionally a non-reducing disaccharide, such as trehalose.

Biocompatible Particles

The delivery system comprises particles of a solid material that is biocompatible. The particles are thus not harmful to living tissue. Advantageously the particles are also biodegradable and are capable of being broken down in vivo into degradation products that are not harmful to living tissue. The particles are solid particles that do not melt or thermally degrade at temperatures below 60° C., preferably at temperatures below 80° C.

Known suitable biocompatible solid materials that may be used in the invention are metallic particles, metalloid particles, especially silicon particles, and graphene particles. Metallic nanoparticles, particularly those containing gold and iron oxides, are widely used in medicine for diagnosis and therapy and have been used as delivery systems for drugs and vaccines.

The biocompatible solid particles may comprise silicon, for example, mesoporous silicon particles. Advantageously, the biocompatible particles may be pure silicon or another hydrolysable silicon-containing material. If they are not pure silicon, they contain at least 50% by weight silicon, i.e. comprise at least 50% by weight silicon atoms based on the total mass of atoms in the particles. For example, the silicon particles may contain at least 60, 70, 80, 90 or 95% silicon. The silicon particles preferably show a rate of hydrolysis, for example in PBS buffer at room temperature, of at least 10% of the rate of hydrolysis of pure silicon particles of the same dimensions. Assays for hydrolysis of silicon-containing material are widely known in the art, see for example WO2011/001456. It will be appreciated that silica ($SiO_2$) nanoparticles, which do not comprise 50% by weight elemental silicon, do not fall under the definition of silicon nanoparticles. Nor are silica nanoparticles hydrolysable, since to hydrolyse silica is thermodynamically unfavourable under the conditions present in vivo. Hydrolysable silicon particles have the advantage that they can degrade to beneficial orthosilicic acid in vivo, for example when formulated as described in WO 2011/012867. A lipid component and/or additional components such as amino acids in the delivery system advantageously act as a stabilizing agent or agents, that modifies or modify the rate of hydrolysis of the silicon in the delivery system in vivo and/or inhibits or inhibit the rate of orthosilicic acid polymerization on degradation of the delivery system in vivo, as discussed in WO 2011/012867.

According to all aspects of the invention, the particles, including those comprising hydrolysable silicon, may be nanoparticles. Nanoparticles have a nominal diameter of between 5 and 300 nm, for example 8 to 200 nm, for example 10 to 150 nm, for example 15 to 100 nm, such as 18 to 80 nm. The nominal diameter referred to above may refer to the mean diameter and at least 90% of total mass of particles in a sample of particles may fall within the size range specified. Particle size may be ascertained or confirmed by transmission electron microscopy (TEM), for example using the NIST-NCL Joint Assay Protocol, PCC-X, version 1.1, "Measuring the size of nanoparticles using TEM", revised February 2010: https://tsapps.nist.gov/publication/get_pdf.cfm?pub_id=854083

The biocompatible particles are preferably etched. If the particles are etched, their total surface area will be increased by virtue of their increased porosity. For example, the surface area may be increased by at least 50% or at least 100% over the surface area of a corresponding non-porous particle. In many circumstances, porous particles in accordance with all aspects of the invention will in reality have a much greater increase in total surface area by virtue of their porosity. Particles comprising hydrolysable silicon can be made porous by standard techniques such as contacting the particles with a hydrofluoric acid (HF)/ethanol mixture and applying a current. By varying the HF concentration and the current density and time of exposure, the density of pores and their size can be controlled and can be monitored by scanning electron micrography and/or nitrogen adsorption desorption volumetric isothermic measurement. According to certain embodiments, the porosity is at least 30, 40, 50 or 60%. This means that, respectively, 30, 40, 50 or 60% of the particle volume is pore space. Preferred pore diameters range from 1 nm to 50 nm, for example from 5 nm to 25 nm. It is preferred that particles are porous, more preferred that they are mesoporous.

The particles in all aspects of the invention may conveniently be prepared by techniques conventional in the art, for example by milling processes or by other known techniques for particle size reduction. The silicon-containing particles may be made from sodium silicate particles, colloidal silica or silicon wafer materials. Macro or micro scale particles are ground in a ball mill, a planetary ball mill, or other size reducing mechanism. The resulting particles may be air classified or sieved to recover particles. It is also possible to use plasma methods and laser ablation for the production of particles.

Lipids

The delivery system of the first to fifth aspects of the invention typically comprises a lipid component.

Lipids, in the present technical field, are generally understood to include fatty acids and fatty acid derivatives, glycerolipids, glycerophospholipids, sphingolipids, saccharolipids and polyketides.

As used in the present application, the term "lipid" may also cover lipidated oligopeptide (a term used interchangeably herein with the term lipopeptide) wherein a short peptide sequence (such as a peptide sequence having 3 to 20 amino acid residues, such as 5 to 15 amino acid residues, especially 3, 4, or 5 amino acid residues, and most especially 5 amino acid residues) is conjugated to one or more fatty acid chains (especially a fatty acid chain having a 10 to 24 carbon chain length, preferably, a 12 to 18 carbon chain length; for example a 14, 15 or 16 carbon chain length; for instance, the peptide moiety may optionally be lipidated with a palmitoyl, cetyl or myristoyl moiety).

A lipidated oligopeptide may optionally be a lipidated tetrapeptide, lipidated pentapeptide or lipidated hexapeptide. Preferably, the amino acid residues include at least one amino acid residue (for example, 2 or 3 amino acid residues) that is cationic at a pH of 7.4 (physiological pH), such as lysine or arginine. For example, the lipidated oligopeptide may include one or more (for example 2) lysine resides. Thus, a particular example is palmitoyl-pentapeptide-4 (CAS number 214047-00-4; abbreviated as PAL-KTTKS):

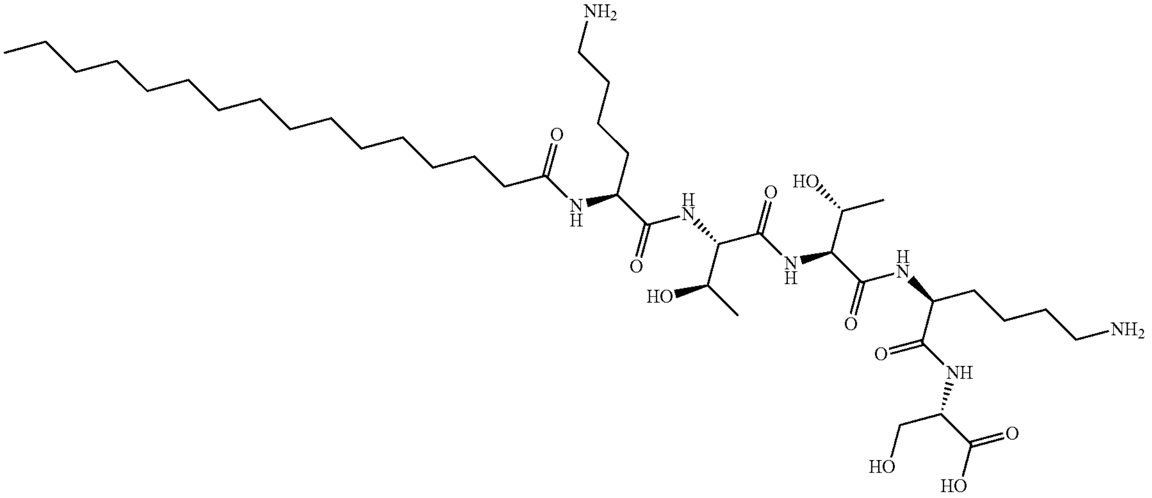 [SMILES: CCCCCCCCCCCCCCCC(=O)N[C@@H](CCCCN)C(=O)N[C@H](C(=O)N[C@H](C(=O)N[C@@H](CCCCN)C(=O)N[C@@H](CO)C(=O)O)[C@@H](C)O)[C@@H](C)O]

Palmitoyl Pentapeptide-4

Thus, in certain preferred embodiments according to all aspects of the invention, the one or more lipids is or comprises one or more lipidated oligopeptides, particularly those having one or more amino acid residues that is or are cationic at a pH of 7.4 (physiological pH; examples include lysine and arginine).

The lipidated oligopeptide may be used in combination with one or more phospholipids, such as DOPE or DPPC. It is thought that the alkyl chain of a lipopeptide may advantageously be assimilated in a phospholipid bilayer, while the surface of the bilayer is decorated with the peptide moiety. It is thought that in this way, the peptide may provide for tissue and/or cell targeting; and, for example where the peptide bears a cationic charge at physiological pH, may stabilise negatively charged APIs, such as nucleic acid, such as mRNA.

According to all aspects of the invention, the lipid component advantageously contains a cationic lipid and/or an ionisable lipid. The lipid component may additionally include a helper lipid, e.g. a phospholipid; a structural lipid, e.g. a cholesterol-based lipid; and/or a PEG-lipid. Preferred lipid components comprise at least a cationic or ionisable lipid and a phospholipid, and optionally a PEG-lipid and/or structural lipid, preferably at least one of a PEG-lipid and structural lipid.

The type of lipid used to treat the surface of a biodegradable biocompatible solid particle of the delivery system may affect its rate of degradation in vivo. For example, the presence of at least one lipid in the delivery system comprising silicon particles has been found to allow for the rate of hydrolysis of the silicon to be controlled, such that the silicon hydrolyses to the bioavailable orthosilicic acid degradation product rather than insoluble polymeric hydrolysis products. It has also been found that surface treating the particle with a lipid may aid uptake of a biological species, such as a nucleic acid, by the delivery system and/or may aid in controlling the rate of release of the biological species from the delivery system. In particular, surface treating silicon particles with a lipid has been found to have a beneficial effect on the surface charge of the silicon particles, providing them with the requisite zeta potential to allow for improved loading of siRNA (short interfering RNA) or mRNA (messenger RNA), and controlling the rate of release of the loaded molecules at a target site.

According to all aspects of the invention, the lipid or lipids of the lipid component may have an average molecular weight in the range of from 300 to 1200 Daltons, such as from 500 to 1000 Daltons.

The lipid component may be or comprise a cationic lipid. The term "cationic lipid" refers to positively charged molecules having a cationic head group attached via some spacer to a hydrophobic tail. Examples include DTDTMA (ditetradecyl trimethyl ammonium), DOTMA (2,3-dioleyloxypropyl-1-trimenthyl ammonium), DHDTMA (dihexadecyl trimethyl ammonium), DOTAP (1,2-dioleoyl-3-trimethylammonium propane) and SA (stearylamine). The positive charge is typically stabilised by a negative counter ion, e.g. a chloride ion. The negative charge of the lipid may be also, or further, stabilised by association with the material of the solid biocompatible particles, e.g. by association with hydrolysable silicon. The presence of cationic lipids has been found to promote cell internalisation by cells in a tissue or organ of interest. The positively charged cationic lipids facilitate take up of the delivery system and biological species, enabling nucleic acid constituents of the biological species to be transcribed in the cells of the tissue or organ of interest producing a therapeutic effect.

The lipid component may be or comprise an ionizable lipid. The term "ionizable lipid" refers to lipids with a group capable of becoming positively charged typically having a Lewis base (hydrogen acceptor) head group attached, e.g. via some spacer, to a hydrophobic tail. Ionizable lipids typically include a head portion containing tertiary amine moieties. Ionizable lipids may be neutral at physiological pH but becomes cationic at lower pH, e.g. below pH 6.5, such as the pH found inside a vacuole as part of endosomal escape. Ionizable lipids are described, for example, in *Nano Lett.* 2020 Mar. 11; 20(3): 1578-1589. Many vaccine platforms use lipid systems that are neutral at physiological pH and then become cationic only when endocytosed into an endosome and pH reduces to around pH 6.2, then the lipids that become cationic allow endosomal escape. Delivery systems comprising neutral lipids allows more of the particle to migrate from the muscle to the lymph node and become phagocytosed by dendritic cells. The ionisable lipid may be stabilised by association with the material of the solid biocompatible particles, e.g. by association with hydrolysable silicon.

The lipid component may comprise a phospholipid as a helper lipid. The term "phospholipid" refers to a lipid comprising a fatty acid chain and a phosphate group. Phospholipids are typically neutral molecules in that they do not have an overall charge or may carry a negative charge, unlike a cationic lipid which is positively charged. Phospholipids are typically zwitterionic compounds comprising both positive and negatively charged components, but no overall charge. As such, phospholipids are typically classified as neutral lipids. Particularly suitable phospholipids are glycerophospholipids. Particularly suitable phospholipids are those in which the polar head group is linked to quaternary ammonium moieties, such as phosphatidylcholine (PC) or hydrogenated phosphatidylcholine. Other examples of phospholipids are fusogenic lipids, such as DOPE (phosphatidyl ethanolamine or 1,2-dioleoyl-sn-glycero-3-phosphoethanolamine). The type of lipid may be selected depending on the nature of the formulation, with neutral or negatively charged phospholipids being preferred for aprotic formulations, while positively charged cationic lipids and small $CH_3$ chain lipids are preferred for protic formulations. The phospholipid may be, or be derived from lecithin. Preferably, the side chain(s) of the phospholipid is/are (an) aliphatic side chain(s) with 15 or more carbon atoms, or an ether side chain with 6 or more repeating ether units, such as a polyethylene glycol or polypropylene glycol chain.

The lipid component may additionally or alternatively comprise a PEG-lipid. Lipids with polyether side chains, may be referred to as "PEG-lipids" or "PEG-ylated" lipids. The PEG-lipid may be a phospholipid such as 1,2-distearoyl-sn-glycero-3-phosphoethanolamine (DSPE) with a PEG side chain, e.g. DSPE-mPEG2000.

The lipid component may include one or more of phosphatidylcholine (PC), hydrogenated PC, stearylamine (SA), dioleoylphosphatidylethanolamine (DOPE), cholesteryl 3β-N-(dimethylaminoethyl)carbamate hydrochloride (DC)-cholesterol, and derivatives thereof. In certain embodiments the lipid component may consist substantially of phosphatidylcholine, hydrogenated phosphatidylcholine, stearylamine, or combinations thereof.

Preferably, in accordance with all aspects of the invention the ratio of lipid(s) (i.e. total lipid component) to silicon, before any further processing of materials (i.e. by means of filtration or sterilization process), is between 0.5:1 and 45:1, for example between 0.8:1 and 20:1, 1:1 and 16:1, 1:1 and 12:1, 1:1 and 11:1, 1:1 and 10:1, 1:1 and 9:1, 1:1 and 8:1, 1:1 and 13:1, 2:1 and 12:1, 2:1 and 11:1, 2:1 and 10:1, 2:1 and 9:1, 2:1 and 8:1, for example between 1:1 and 7:1, between 2:1 and 7:1, between 3:1 and 6:1, between 4:1 and 5:1. It has been found that lipid component to silicon molar ratios of between 0.8:1 and 20:1 are particularly advantageous, for example 16:1, 12:1, 8:1, or 2.5:1. Advantageously, this ratio of lipid to silicon provides a multilamellar vesicle system able to control the release of, and stabilise, the nucleic acid in contact with the particle of hydrolysable silicon and to facilitate the controlled release of the bioavailable degradation product of the silicon, i.e. orthosilicic acid.

Advantageously, the lipid component can exert a significant effect on the surface charge of the silicon particles. Particles comprising hydrolysable silicon treated with phosphatidylcholine (PC), phosphatidylethanolamine (PE) and lecithin demonstrated a negative surface charge when zeta potential analysis was performed (ranging from −60 to −20 mV, with ratios of silicon:Lipid ranging between 1:1 to 1:3). Particles surface treated with stearylamine demonstrate a positive zeta potential (ranging from 0 to 40 mV, with ratios of silicon:lipid ranging from 1:1 to 1:3). The lipid component may be stabilised by association with the material of the solid biocompatible particles, e.g. by association with hydrolysable silicon. Conversely the solid biocompatible particles, hydrolysable silicon particle, may be stabilised by association with the lipid components.

Non-Reducing Disaccharide

According to all aspects of the invention there is optionally included in the delivery system at least one non-reducing disaccharide. The non-reducing disaccharide may optionally be selected from sucrose, trehalose, raffinose, stachyose and verbascose or mixtures of any thereof, most preferably the non-reducing disaccharide is trehalose, or a mixture comprising trehalose.

When the delivery system comprises silicon particles, the non-reducing disaccharide (for example, trehalose or a mixture comprising trehalose) is optionally present at a weight ratio to silicon of at least 1000:1, at least 100:1, at least 50:1, at least 10:1, at least 1:1, or at least 0.5:1. Preferably, the non-reducing disaccharide is trehalose which is optionally present a weight ratio to silicon of at least 1000:1, at least 100:1, at least 50:1, at least 10:1, at least 1:1, or at least 0.5:1

It is postulated that non-reducing disaccharides, especially trehalose may act as a desiccation-protectant. Non-reducing disaccharides may act as a cocoon that traps the biomolecule inside a glassy sugar matrix such that the movement of proteins is restricted by the sugar matrix. Trehalose may be particularly effective due to its ability to transit between one crystalline form and another, without relaxing its structural integrity and/or due to its particularly high glass transition temperature compared to other disaccharides such as sucrose. In addition, in amorphous trehalose, local pockets of crystalline dihydrate exist, which trap residual water molecules, immobilizing them when water is scarce. An additional advantage of including a non-reducing disaccharide, such as trehalose, is that the presence of the non-reducing disaccharide facilitates resuspension of a powdered material.

Amino Acids

The delivery system according to all aspects of the invention may include the additional optional presence of one or more amino acids.

In its broadest sense, the term "amino acid" encompasses any artificial or naturally occurring organic compound containing an amine ($-NH_2$) and carboxyl ($-COOH$) functional group. It includes an α, β, γ and δ amino acid. It includes an amino acid in any chiral configuration. According to some embodiments (for example, when the nanoparticles of the invention are formulated with one or more of PC, hydrogenated PC, SA, DOPE, DC-cholesterol, and derivatives thereof) the amino acid is preferably a naturally occurring α amino acid. It may be a proteinogenic amino acid or a non-proteinogenic amino acid (such as carnitine, levothyroxine, hydroxyproline, ornithine or citrulline).

In preferred embodiments the amino acid comprises arginine, histidine, lysine, proline or glycine or a mixture thereof, especially a mixture of arginine and glycine or a mixture of glycine and lysine. Preferably the amino acid is arginine or glycine or a combination of glycine and arginine or a combination of glycine and lysine. In particularly preferred embodiments, the amino acid comprises glycine, or a combination of glycine and lysine. Such amino acids may function to stabilise the solid biocompatible particle, especially and biodegradable biocompatible particles such as silicon particles. The amino acid advantageously controls, e.g. reduces the rate of, the hydrolysis of silicon both in storage and in vivo.

When the delivery system comprises silicon particles, the amino acid (for example glycine, or a mixture of glycine and lysine) is optionally present at a weight ratio to silicon of at least 500:1, at least 50:1, at least 5:1, at least 2.5:1, at least 1:1, or at least 0.5:1 or 0.05:1. Preferably, the amino acid is glycine, which is optionally present a weight ratio to silicon of at least 500:1, at least 50:1, at least 5:1, at least 2.5:1, at least 1:1, or at least 0.5:1 or 0.05:1. Advantageously, this ratio of amino acid to silicon further affects the rate of release of, and stabilises, a biological species, such as an RNA molecule, associated with the particle.

According to all aspects of the invention, the delivery system advantageously comprises biocompatible particles treated with a lipid component (for example, comprising a cationic lipid) and an amino acid. The delivery system may additional comprise a non-reducing disaccharide, such as trehalose.

Biological Species

According to all aspects of the invention the biological species may comprise a nucleic acid, an antigen or a vaccine. The nucleic acid may be a DNA or RNA, especially RNA or plasmid DNA. The RNA may, for example, be mRNA or saRNA, shRNA or siRNA, especially an mRNA vaccine. The mRNA may be a self-amplifying mRNAs capable of amplifying in vivo. The methods and formulations of the invention have been found to be particularly effective in stabilising RNA which is particularly susceptible to degradation, both ex vivo during storage and in vivo following administration to a patient.

The nucleic acid may be derived from a biological source, for example, an in vitro transcribed nucleic acid or a plasmid nucleic acid. Advantageously, the formulation of the invention protects a nucleic acid (e.g. RNA) derived from a biological source from degradation by enzymes from said biological source. Thus formulation of the third aspect of the invention may protect a biologically derived nucleic acid from degradation by enzymes from said biological source during storage. Likewise the method of the second aspect of the invention may be a method of protecting a nucleic acid derived from a biological source from degradation by enzymes from said biological source. Certain embodiments of the biological species according to the invention comprise nucleic acid (such as mRNA) from a biological source and a low but measurable level of degradative enzyme deriving from that biological source.

In its broadest sense, the term "siRNA" encompasses small interfering RNA (siRNA), sometimes known as short interfering RNA or silencing RNA, and comprise double-stranded RNA molecules of 5 to 50 base pairs in length, and operate within the RNA interference (RNAi) pathway. For example 10 to 45 base pairs, 15 to 40 base pairs, of 20-30 base pairs, especially 20 to 25 base pairs in length.

The term "mRNA" encompasses messenger RNA and may optionally include mRNA comprising a 5-prime cap and/or a poly-adenylated terminus. Alternatively, one of both of those features may be absent. mRNA may be in certain embodiments at least 100, at least 200, at least 300, at least 500, at least 1000, base pairs in length.

RNA according to embodiments of all aspects of the invention may be naturally occurring or chemically modified to enhance their therapeutic properties, such as enhanced activity, increased serum stability, fewer off-targets and lower immunological activation. Chemical modifications to the RNA may include any modifications commonly known in the art. mRNA of the invention may encode multiple proteins. For example a viral antigen and an adjuvanting protein or multiple viral antigens.

The biological species may be an antigen or mRNA that encodes an antigen, thereby providing a formulation which is a vaccine. The antigen may be an antigen of a pathogen or a viral antigen, for example an antigen of SARS-CoV-2, for example an antigen deriving from the spike protein of SARS-CoV-2.

Nucleic acids such as RNAs for use in accordance with the invention include double- and single-stranded DNA, RNA, DNA:RNA hybrids, and hybrids between PNAs (peptide nucleic acids) or RNA or DNA. The terms also include known types of modifications, for example, labels which are known in the art, methylation, "caps," substitution of one or more of the naturally occurring nucleotides with an analog, internucleotide modifications such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalklyphosphoramidates, aminoalkylphosphotriesters), those containing pendant moieties, such as, for example, proteins (including nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide or oligonucleotide.

It will be appreciated that, as used herein, the terms "nucleoside" and "nucleotide" will include those moieties which contain not only the known purine and pyrimidine bases, but also other heterocyclic bases which have been modified. Such modifications include methylated purines or pyrimidines, acylated purines or pyrimidines, or other heterocycles. Modified nucleosides or nucleotides will also include modifications on the sugar moiety, e.g., wherein one or more of the hydroxyl groups are replaced with a halogen, an aliphatic group, or are functionalized as ethers, amines, or the like. Other modifications to nucleotides or polynucleotides involve rearranging, appending, substituting for, or otherwise altering functional groups on the purine or pyrimidine base which form hydrogen bonds to a respective complementary pyrimidine or purine, e.g., isoguanine, isocysteine, and the like. In some embodiments, the oligonucleotides and/or probes include at least one, two, three or four modified nucleotides.

In some embodiments, the nucleic acids such as the RNAs disclosed herein include one or more universal bases. As used herein, the term "universal base" refers to a nucleotide analogue that can hybridize to more than one nucleotide selected from A, U/T, C, and G. In some embodiments, the universal base can be selected from the group consisting of deoxyinosine, 3-nitropyrrole, 4-nitroindole, 6-nitroindole, 5-nitroindole.

Biological species containing siRNA may optionally include siRNA which is synthetically manufactured by chemical synthesis outside of a biological system. Such siRNA can be manufactured free of nucleic acid degradative enzymes. However the preferred way of manufacturing longer nucleic acids such as mRNA (for example for use in vaccine formulations) involves the use of a biological system. The mRNA is typically purified from that biological system in order to reduce the level of degradative enzymes (for example RNA-ases). It may be difficult to completely eliminate all degradative enzymes. This would normally necessitate storage at low temperature to minimise enzyme activity. However it has been found that according to the invention formulating nucleic acid (such as mRNA) with a delivery system according to the invention, especially a delivery system comprising particles comprising hydrolysable silicon, a lipid component and a non-reducing disaccharide to form complex and then dispersing the complex in a biodegradable gel matrix, can increase the storage life of the mRNA in a formulation possibly negating, mitigating or reducing the need for low temperature storage.

Accordingly, methods of the second aspect of the invention include methods of protecting the biological species (for example mRNA, saRNA, shRNA or siRNA) from degradation due to enzymes present in the nucleic acid preparation. Preferably enzymatic degradation at room temperature (20° C.) is reduced by at least half, more preferably by a factor or at least 5, 10, 35, 50, 100, 500 or 1000 compared to an equivalent composition without particles of hydrolysable silicon-containing material. Preferably the biological species in the formulation of the invention has a half-life at 4° C. of at least 3 months, at least 6 months or at least 12 months. It has been found that formulations prepared by the method of the invention do not degrade when stored at 40° C. for at least 48 hours nor when stored at room temperature (20° C.) for at least 8 days.

Biological Species—Particle Association

The biological species and the delivery system with which it is contacted are advantageously associated together in a complex. Typically, the biological species is loaded onto a delivery system comprising biocompatible solid particles, e.g. silicon particles, onto which a lipid component, e.g. comprising a cationic lipid and/or ionisable lipid, preferably together with a phospholipid and also a PEG-lipid and/or a structural lipid, has previously been loaded optionally along with a non-reducing disaccharide, especially trehalose, and other optional components such as an amino acid. Contacting of the biological species with the delivery system thus typically forms a complex comprising biocompatible solid particles, especially silicon particles, loaded with a lipid component, a non-reducing disaccharide and the biological species, together with any additional components, such as amino acids.

Advantageously at least 80%, for example at least 90% of the nucleic acid (for example siRNA or mRNA) or other biological species by weight present in the formulation of all aspects of the invention is associated with particles of the delivery system. By this it is meant that the biological species is non-covalently associated with the biocompatible and biodegradable particles, for example, nucleic acid is non-covalently associated with silicon particles. It is hypothesised that when that takes place, the random movement of the biological species is reduced and opportunities for it to be degraded, for example by degradative enzymes presence in a formulation, are reduced.

The rate of degradation of a silicon particle and the end of its association with the biological species is governed by the hydrolysis of the silicon in the particles. As this rate can be controlled, the rate at which the nucleic acid or other biological species (such as siRNA saRNA, shRNA or mRNA) becomes bioavailable can also be controlled in order to avoid dose-dumping and/or to ensure gradual release over a suitably long period of time.

Treating lipid-treated biodegradable biocompatible particles with an amino acid (for example, one or more of glycine, arginine, lysine and histidine, preferably glycine or a combination of glycine and lysine) has been found to provide a beneficial stabilising effect on a biological species, such as nucleic acids (for example, mRNA, saRNA, shRNA or siRNA). In particular, treating the lipid-treated particles with amino acids has been shown to stabilise biological species such as RNA in biological fluids, for example in ocular tissues. Lipid-treated particles formulated with an amino acid in this manner are particularly suitable for delivery to the body for example delivery by transcutaneous injection, intravitreal injections and intraocular implantations.

To assist in the complexing of the biological species with a particle of the delivery system, the delivery system may optionally further comprise a polycationic nucleic acid-binding component. The term "polycationic nucleic acid-binding component" is well known in the art and refers to polymers having at least 3 repeat cationic amino acid residues or other cationic unit bearing positively charged groups, such polymers being capable of complexing with a nucleic acid under physiological conditions. An example of a nucleic acid-binding polycationic molecule is an oligopeptide comprising one or more cationic amino acids. Such an oligopeptide may, for example, be an oligo-lysine molecule, an oligo-histidine molecule, an oligo-arginine molecule, an oligo-ornithine molecule, an oligo diaminopropionic acid molecule, or an oligo-diaminobutyric acid molecule, or a combined oligomer comprising or consisting of any combination of histidine, arginine, lysine, ornithine diaminopropionic acid, and diaminobutyric acid residues. Further examples of polycationic components include dendrimers and polyethylenimine.

Preferred Combinations

According to all aspects of the invention, especially preferred embodiments relate to an active ingredient which is a nucleic acid (especially mRNA, and especially a mRNA encoding an antigen of a mRNA vaccine). In some embodiments, cationic lipid is present, for example a lipid which is or comprises DOTAP. However, it has been found that DOTAP is not always necessary for the present formulations, as shown in the Examples hereinbelow. In accordance with the Examples, therefore, in especially preferred embodiments, the one or more lipids is, are or comprise(s) one or more of a phospholipid (such as DPPC and/or DOPE) and a lipidated oligopeptide having one or more amino acid residues that is or are cationic at a pH of 7.4 (physiological pH; examples include lysine and arginine). Optionally also present are one or more sugars (particularly trehalose) and/or one or more amino acids (particularly glycine).

Alternatively, in other preferred embodiments, the one or more lipids are or comprise one or more of a phospholipid (such as DPPC and/or DOPE), and are formulated with one or more coenzymes (for example, NAD); one or more flavanols (for example, quercetin) and/or one or more amino acids (for example, tyrosine). Optionally also present are one or more sugars (particularly trehalose) and/or one or more amino acids (particularly glycine).

Biodegradable Gel Material

A "gel" is defined by IUPAC as non-fluid colloidal network or polymer network that is expanded throughout its whole volume by a liquid. Gels are typically dilute cross-linked system, which exhibits no flow when in the steady-state consisting of two or more components, one of which is a liquid, present in substantial quantity and one of which is a cross-linked polymeric matrix swollen by the liquid. Crosslinking at network junction points may be provided by chemical bonds between polymer chains, or through the physical aggregation of polymer chains at network junction points. The biodegradable gel material of the invention is a gel that does not have a harmful effect on the human body and which is degraded in vivo to non-harmful degradation products.

In step (iii) of the methods of the invention (i.e. the methods of the first, second, fourth and fifth aspects of the invention) the biological species and a delivery system is dispersed in a biodegradable gel material. Likewise the formulation of the third aspect of the invention comprises a biodegradable gel material. The medicament of the sixth aspect of the invention may comprise the biodegradable gel material or may comprise residues of the biodegradable gel material. The material that forms the matrix of the biodegradable gel of the formulation of the third aspect of the invention is advantageously present in the medicament of the sixth aspect of the invention but not necessarily in gel form. For example the material that forms the biodegradable gel may be dissolved in a liquid medium in the medicament of the sixth aspect of the invention. Advantageously, the material that forms the matrix of the biodegradable gel is not removed on preparation of the medicament.

The gel material is typically a polymer network formed through the physical aggregation of polymer chains. Aggregation may for example be a result of hydrogen bonding and/or crystallization, that results in regions of local order acting as the network junction points. The swollen network may be a thermos-reversible gel in which the regions of local order are thermally reversible. Alternatively the gel material may be a covalent polymer network, e.g. a network formed by crosslinking polymer chains.

The gel may be in the form of a xerogel in which the liquid swelling agent, e.g. water, has been removed to leave and open network of the of crosslinked polymer. As such xerogels lack water, the embedded delivery system and biological species is protected from degradation mechanisms involving water.

The gel may be a hydrogel in which the swelling agent is water. Hydrogels are inherently hydrated materials, and the polymer network often comprises only a small fraction of the total volume. Therefore, in comparison with dry materials, the adhesion of hydrogels relies primarily on sparse and loosely packed adhesion junctions surrounded by water. A hydrogel material is typically formed of a hydrophilic polymer that is capable of absorbing water without dissolving in water. A hydrogel material is capable of absorbing 5% by weight water, typically at least 10% by weight water. Hydrogels may be formed from natural, synthetic, or semi-synthetic polymers, which are physically or covalently crosslinked. Hydrogels of natural origin include; chitosan-, alginate-, fibrin-, gelatin-, cellulose- and hyaluronic acid-based hydrogels. Examples include some naturally occurring starches such as potato starch. Synthetic hydrogels include poly(ethylene glycol) or poly(vinyl alcohol) polymer matrices. Semi-synthetic hydrogels are typically functionalised natural hydrogels such as gelatin methacryloyl hydrogels, which are gelatin-based polymers functionalized by synthetic methacryloyl groups, and hydroxypropyl methylcellulose (HPMC) “hypromellose”. The hydrogel used in the invention is biocompatible and biodegradeable. Preferred hydrogels include hyaluronic acid-based hydrogels, such as sodium hyaluronate and cellulose-based hydrogels such as hypromellose.

Gels are believed to protect embedded substances from degradation due, at least in part, to a reduction the ability of two functional groups of substances embedded in the gel to find each other to react. As such even gels containing water, i.e. hydrogels, have been found to be effective in stabilizing the complexes of the invention, due to their ability to immobilizing species with the gel matrix preventing degradation reactions from occurring.

Non-covalent interactions between the solid particles of the delivery system (e.g. silicon particles) is believed to stabilize the gel structure. In particular non-covalently cross-linked gel structures have been found to be stabilized by the embedding of the solid particles of the delivery system. As a result the gel structure protects the embedded delivery system and biological species from degradation while in turn being stabilized. The biodegradable gel based formulations of the invention have therefore been found to be advantageous for the storage and protection of biological from degradation without requirement of permeant binding within gel matrix. Furthermore the storage stable formulations comprising a biodegradable gel can be used as a medicament, or used to prepare a medicament, without the need to extract the biological species.

Preparation of Formulations

Preparation of the Particles of Biocompatible and Biodegradable Material

The delivery system comprises particles of biocompatible solid material. The biocompatible material may be a metal, metalloid material, typically gold, carbon tube, graphene, silica, porous elemental materials including porous diamond, gold, silver, and hydrolysable silicon.

In a preferred embodiment, the solid biocompatible particles are hydrolysable silicon particles. Hydrolysable silicon may conveniently be prepared by techniques conventional in the art, for example by milling processes or by other known techniques for particle size reduction. The silicon-containing particles may, in certain embodiments, be made from sodium silicate particles, colloidal silica or silicon wafer materials. Macro or micro scale particles are ground in a ball mill, a planetary ball mill, plasma or laser ablation methods or other size reducing mechanism. The resulting particles may be air classified to recover nanoparticles. It is also possible to use plasma methods and laser ablation for nanoparticles production.

Porous silicon particles can, for example, be produced by anodically etching silicon wafers using aqueous HF acid then crushing the etched wafers and sieving or air-classified to obtain a uniform particle size selection. Alternatively silicon powder can be prepared or purchased and then etched to increase the porosity of the powder. Etching may increase the surface area of a silicon material by a factor of at least 1.5, 2, 2.5, 3, 3.5 or 4 over the surface area of an equivalently sized non-porous material. By varying the HF concentration and the current density and time of exposure, the density of pores and their size can be controlled and can be monitored by scanning electron micrography and/or nitrogen adsorption desorption volumetric isothermic measurement.

According to certain embodiments the porosity is at least 30, 40, 50 or 60%. This means that, respectively, 30, 40, 50 or 60% of the particle volume in pore space. Preferred pore diameters range from 1 nm to 50 nm, for example from 5 nm to 25 nm.

Formation of the Delivery System

Further constituents of the delivery system may be loaded onto the particles of biocompatible and biodegradable material prior to contact with the biological species, concurrently with contact of the particles with the biological species or subsequent to contacting of the particles with the biological species. Typically non-reducing disaccharide and amino acid components are combined with the particles prior to contact with the biological species. The lipid components of the delivery system may be combined with the particles prior to, concurrently with or subsequent to contact of particles with the biological species.

The delivery system may be prepared by dispersing the particles (e.g. porous silicon nanoparticles) in a volatile alcohol solvent (such as methanol, ethanol or propanol, e.g. methanol) to activate the particles, followed by mixing with an aqueous solution containing non-reducing disaccharide (e.g. trehalose) and amino acid (e.g. glycine). Alternatively, the solvent is removed from the activated particles and the activated particles are dispersed in nuclease-free water together with the non-reducing disaccharide (e.g. trehalose) and amino acid (e.g. glycine). Subsequently, the lipids are added as a solution or dispersion (e.g. in methanol). Sonication may optionally be employed to enhance dispersion. The resulting dispersion is extruded in flow at elevated temperature (e.g. 60° C.) over an extrusion membrane. Multiple passages can be employed. After the extrusion, the methanol and potential other impurities are removed, for example, using tangential flow filtration.

Contact of the Biological Species with the Delivery System

In step (i) of the method of the first and second aspect of the invention, and certain embodiments of the fourth and fifth aspects of the invention, the biological species is contacted with the delivery system. The contacting step may merely involve mixing a solution of the biological species with the delivery system, for example under conditions leading to the complexation of the biological species with the delivery system. The contacting step may involve contacting the biological species with the particles of biocompatible and biodegradable material prior to addition of the lipid components. Addition of the lipid components after contact of the biological species with the particles of biocompatible and biodegradable material may facilitate the formation of a lipid encapsulation layer on the surface of the particles encapsulating both the biocompatible and biodegradable material and the biological species. Typically particles of biocompatible and biodegradable material, such as porous hydrolysable silicon, are mixed with the non-reducing disaccharide, the biological species and optional amino acid(s) and then contacted with the lipid components to form lipid-encapsulated particles in which the biological species is associated with the silicon or other biocompatible and biodegradable material within a lipid encapsulation.

It is postulated that a delivery system comprising particles, especially particles of hydrolysable silicon, increase the stability of a biological species, especially a nucleic acid, by restricting the mobility (molecular motion) of the biological species. In addition when additional components of the delivery system such as lipids and peptides are bound to silicon particles a stabilised complex can be formed in which both the hydrolysable silicon and the additional components of the delivery system such as lipids and peptides are stabilised. For example lipid, components may form a lipid membrane round the silicon particle which both protects the silicon from hydrolysis and stabilised the lipid molecules from degradation as well as stabilises biological species such as RNA complexed to the silicon. Positively charged species such as cationic lipids and other lipid components bearing a positive charge including phospholipids are believed to bind to silicon thereby stabilising the integrity of the positive charge components. Unlike liposomes that include an oil/water/surfactant interaction, no moisture is present within the system of the invention that includes lipids-silicon and other organic molecules in a non-vesicle structure, thus removing an aqueous environment for enzymes or free-radicals to operate. It is believed that inclusion of the biological species with the non-vesicle structure formed by the silicon particles and lipid component thus protects the biological species from degradation.

The solid material may optionally be conveniently passed through a filter (a process which may be referred to as "extrusion") or subjected to a tangential flow filtration/sterilization process, depending on the nature of the intended product profile.

Lyophilisation

In step (ii) of the method of the first and second aspect of the invention, and certain embodiments of the fourth and fifth aspects of the invention, the biological species and the delivery system are optimally lyophilised, for example to form a powder. Lyophilisation removes water from the biological species and the delivery system and enables a dry powder to be dispersed in a highly concentrated biodegradable gel in the subsequent dispersion step (iii), thereby minimizing the presence of water. It is also postulated that a lyophilisation step promotes complexation of the biological species and the delivery system, for example, promoting binding of a nucleic acid and lipid component with silicon particles.

Dispersion of the Biological Species and the Delivery System into the Biodegradable Gel In step (iii) of the method of the first and second aspect of the invention, and certain embodiments of the fourth and fifth aspects of the invention, the biological species and the delivery system are dispersed in a biodegradable gel. Dispersion in a biodegradable gel typically involves preparation of an aqueous dispersion of the biodegradable gel material and introduction of the biological species and the delivery system to the aqueous dispersion, either as an aqueous dispersion or as a solid powder. Preferably the biological species and the delivery system have been lyophilised following contact and are introduced to the biodegradable gel as a powder. After the biological species and delivery system have been dispersed in an aqueous dispersion of the biodegradable gel the resulting dispersion may be stored as a liquid dispersion or converted to a solid or semi-solid gel, for example in a gelation step optionally involving the removal of water. The biological species and the delivery system are advantageously embedded in the matrix of the biodegradable gel. Embedding in the biodegradable gel may facilitate immobilisation of the biological species, a lipid component and any contaminants that could promote degradation, such as enzymes, thus arresting degradation.

Medicaments

The (optionally, oral or injectable) medicament of the invention, e.g. the medicament of the sixth aspect of the invention may, for example, be a liquid or solid dosage form. The medicament may be in the form of an injectable dosage form comprising biological species complexed with a delivery system together with compounds capable of forming a hydrogel matrix dispersed in a liquid carrier system. Solid dosage forms include those for oral administration, such as capsules and tablets, suppositories, dissolvable films, e.g. for sub-lingual administration, and transdermal delivery patches, such as delivery patches using a multiplicity of microneedles for injection.

A formulation or medicament of the invention may be provided in a delivery device, for example in an injection device such as a syringe or a multiplicity of microneedles.

EXAMPLES

Various aspects and embodiments of the invention are now described with reference to the following non-limiting examples. Where the examples fall outside the scope of some aspects of the invention, they are included as comparative examples.

Overview of Experimental Results

A binding efficiency study was performed with Delivery Systems dispersed in a glue-like biodegradable gel matrix, and exposed to 40° C. for at least 48 consecutive hours. In particular, a gel retardation assay was performed on siRNA loaded on Delivery System formulations SIS0012 & MVI0010 (silicon) and SIS0013 (boron-doped silicon) embedded into sodium hyaluronate (1% w/w) or hypromellose (2% w/w) biodegradable gels following storage at room temperature or at 40° C. and analyzed at designated time points (0, 2, 4, 6, 24, and 48 h) by gel electrophoresis. The gel electrophoresis system used for these experiments consists of a gel electrophoresis device, precast agarose gels (1%, with running buffer and electrode provided within the gel) and a camera. The samples, control (naked siRNA), and DNA ladder were mixed with the required amount of the loading buffer to make a total volume of 20 μL. The amount of RNA used per well cell was 200 ng/well which follows the standard protocol for agarose gel assay and which is below saturation amount.

The results revealed that the nucleic acid binding efficacy of Delivery System SIS0012 & MVI0010 (with silicon) and Delivery System SIS0013 (with boron doped silicon) is retained even when samples are exposed to 40° C. for 48 consecutive hours. It was observed that all of the tested Delivery System-formulations were able to form complexes with siRNA and completely stop its migration through the gel. Furthermore, both SIS0012-formulations and SIS0013-formulations were found to be stable at room temperature and also at 40° C. for up to 48 hours.

Preparation of a Lipid-Functionalised Silicon Nanoparticle (SiNP) Delivery System Lipid components were dissolved in methanol. Simultaneously, porous silicon dioxide nanoparticles (SiNPs) of 30 nm diameter of either undoped silicon from American Elements (CAS #7440-21-3, supplier code SI-E-0181M-NP100N) or Boron doped silicon are dispersed in methanol and subsequently the solvent is evaporated in a slow evaporation process to yield the activated SiNPs. This activation step is aimed at rendering the SiNPs amenable to dispersion in water. The activated SiNPs are dispersed in nuclease-free water together with glycine and optionally trehalose.

In the preparation of complexes SIS0012 and SIS0013, the dispersion of activated SiNPs together with glycine and trehalose n nuclease-free water are used to hydrate the lipids. The dispersion is extruded over extrusion filters. After solvent evaporation, the lipid-functionalised SiNP delivery system is collected.

In the preparation of MVI0010, the lipids are solubilised in methanol and then slowly injected into the dispersion of SiNPs together with glycine and trehalose in nuclease-free water and then tangential flow filtration is applied using 3 cycles at 0.8 μm, 3 cycles at 0.4 μm and 3 cycles at 0.1 μm.

The compositions of the delivery systems SIS0012/MVI0010 and SIS0013 are provided in Table 1.

TABLE 1

| Delivery System composition before applying extrusion | | | | | | |
|---|---|---|---|---|---|---|
| Lipids | | | Activated | | | |
| DOTAP | DOPE | mPEG2000-DSPE | SiNPs (≤100 nm) | Glycine | Trehalose | Nuclease-free water |
| 7.25 mg | 7.30 mg | 1.45 mg | 1 mg | 0.5 mg | 1 mg | Up to 10 ml |
| 1.45 mL | 1.46 mL | 0.29 mL | | 1 mL | | Up to 10 ml |

Characterisation of Boron-Doped Silicon Present in SIS0013

Single side polished wafer, CZ

Diameter: 150±0.2 mm

Orientation: (100)±1°

Type: p/boron resistivity: 0.014±25% Ohmcm. Close to 5×10^18 Atoms/cm$^3$.

Primary flat: 57.50±2.5 mm

Primary flat1 Location: D <100> to {110}

Thickness: 675±15 μm

TTV: <=18 μm

TIR: <=5 μm

The films are around 40% porosity and up to 50 μm thick prior to being crushed into particles.

Preparation of Stock Solutions a) Si-NPs+GLY+THR: 50 mg of SiNPs, 50 mg of Trehalose and 25 mg of Glycine were suspended in 50 ml of nuclease-free water and sonicated for 60 minutes.

b) DOTAP-Cl: 50 mg of DOTAP were solubilized in 10 ml of methanol and sonicated until fully solubilised.

c) DOPE: 60 mg of DOPE were solubilized in 12 ml of methanol and sonicated until fully solubilised.

d) mPEG2000-DSPE: 40 mg of mPEG2000-DSPE were solubilized in 8 ml of methanol and sonicated until fully solubilised.

Film Preparation a) Lipids, in amounts given in Table 1 were transferred from the stock solution in a clean glass round bottom flask and mix.

b) The solvent was evaporated using rotary evaporator using a water bath at 23° C. and vacuum.

Rehydration of the Film a) Add the Si-NPs+GLY (+THR) solution to give a lipid:SiNP: ratio of 16:1 to the lipid film and adjust the final volume to 10 mL, using nuclease free water.

b) Cover the flask with parafilm and rehydrate the film, agitating the flask in a water bath (60° C.) for 5 minutes.

c) Split 1 mL of the samples in an RNA-free Eppendorf, 10 Eppendorf in total. Store the suspension in the fridge.

Extrusion Process a) The lipid suspension is passed through a membrane filter of the pore sizes 0.4 μm and 0.1 μm, 20 times, at 60° C.

Example 1

Evaluation of the Stability of Formulations Loaded with a Commercial mRNA and Embedded in Sodium Hyaluronate Biodegradable Gels at Different Temperatures Using Agarose Gel Electrophoresis Preparation of mRNA-Delivery System Complexes Dasher GFP mRNA stock solution has a concentration of 1 mg/mL in nuclease-free water. This stock solution was diluted using an equal volume of nuclease free water to obtain a working solution with a concentration of 0.5 mg/mL.

The mRNA-delivery system complexes were prepared by mixing 50 μL (25 μg) of mRNA solution with 200 μL of the delivery system dispersion (delivery system/RNA weight ratio: 12:1). The mixtures were incubated at room temperature for 40 min to allow for complete complexation and then either used in the liquid form or freeze-dried and redispersed in 250 μL of nuclease free water. The mRNA-delivery system complexes were then embedded by being mixed with equal volume (250 μL) of sodium hyaluronate hydrogel. To prepare the controls, naked mRNA either in the liquid form or as freeze dried and reconstituted solution was mixed with equal volume of sodium hyaluronate hydrogels (1% w/w). Naked mRNA solution with the same concentration was also used as an additional control. The final concentration of mRNA in all samples was 0.05 μg/μL. The final preparations were split into 30 μL aliquots (for each analysis time point) to minimize the risk of cross-contamination during storage and analysis. All samples and controls were stored at two different temperatures, room temperature and in a water bath set to 40° C. The amount of RNA used per well cell was 200 ng/well which follows standard protocols for agarose gel assay which is below saturation amount. The performance of a gel electrophoresis assay like any other biological assays can be at some level dependent on correct parameters being used. Molecular weight of the nucleic acid, selection of right buffers and gel loading volume can all be important. 200 ng/well was chosen to ensure that the gel was neither under-loaded nor overloaded.

Agarose Gel Electrophoresis

At designated time points (0 h, 6 h, 24 h, and 48 h), the mRNA-Delivery system-Biodegradable gel formulations and the controls were subjected to gel electrophoresis. The DNA ladder (E-Gel™ 1 Kb plus Express DNA ladder) was also used as a size guide. The samples were loaded onto the E-Gel™ agarose gel (1%) in the E-Gel™ Power Snap electrophoresis device. The gel was transilluminated and imaged at 3 min and 7 min using the E-Gel™ Power Snap lectrophoresis camera. The total amount of mRNA loaded onto the gel was 0.2 μg/well for all of the samples and controls.

Test 1: Stability of the Liquid mRNA-Delivery System Complexes

Figure 2:
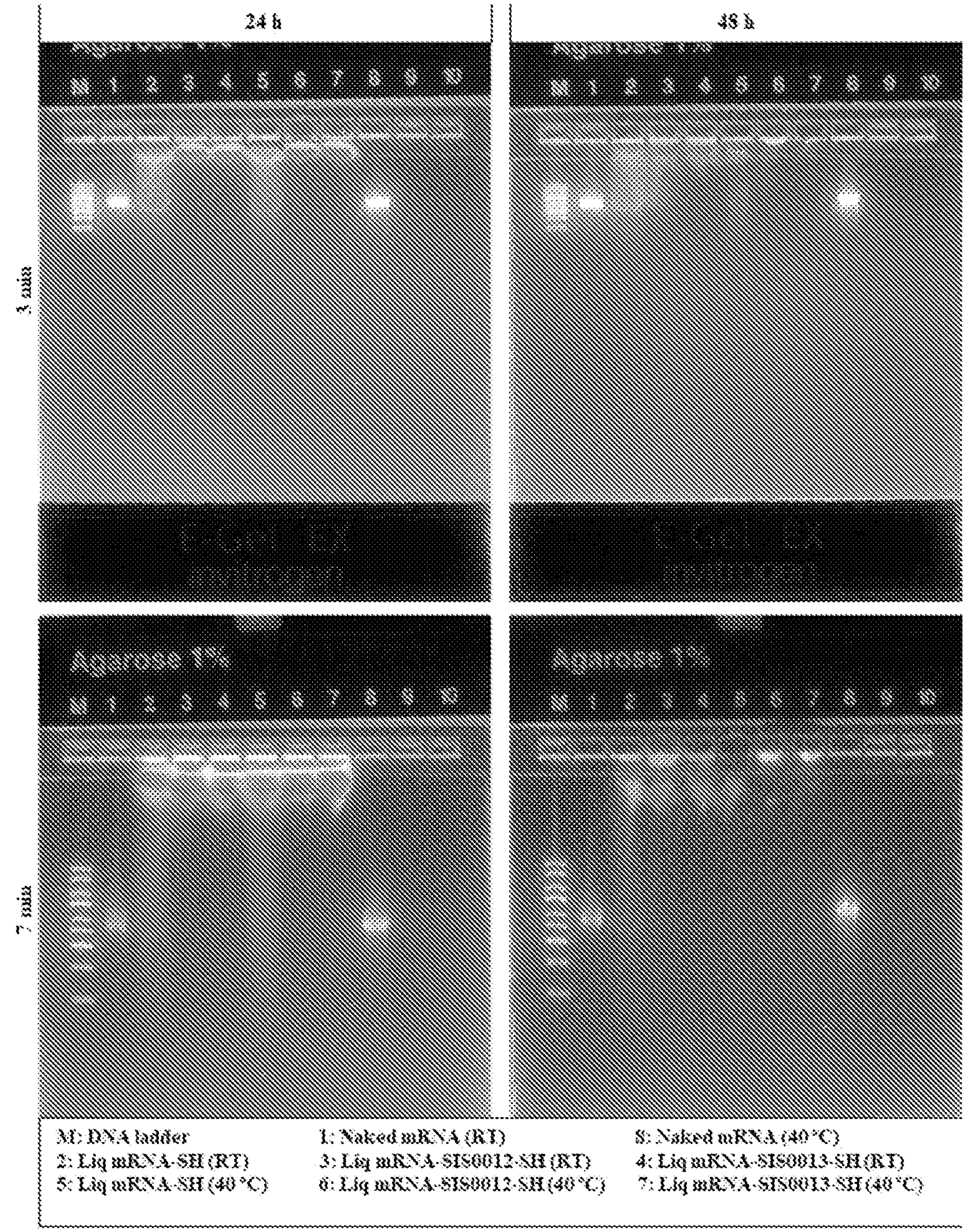
FIG. 2 Gel electrophoresis images of liquid mRNA-Biocourier formulations embedded in sodium hyaluronate biodegradable gels 24 and 48 h after storage at room temperature (RT) or 40° C.

The agarose gel electrophoresis images of the liquid mRNA-delivery system formulations embedded in sodium hyaluronate hydrogel shortly after preparation and up to 48 h after storage at either room temperature or 40° C., are provided in FIGS. 1 and 2. FIG. 1 provides gel electrophoresis images of the liquid mRNA-Delivery System formulations embedded in sodium hyaluronate (SH) hydrogels (3, 4, 6, 7) at the time of preparation and 6 h after storage at room temperature (RT) or 40° C. FIG. 2 provides gel electrophoresis images of the liquid mRNA-Delivery System formulations embedded in sodium hyaluronate hydrogels (3, 4, 6, 7) 24 and 48 h after storage at room temperature (RT) or 40° C. Naked mRNA (1, 8) and naked mRNA embedded in hydrogel (2, 5) were used as controls.

As observed both the naked mRNA (1, 8) and the mRNA embedded in the hydrogel (2, 5) migrated through the agarose gel. Also, some of the hyaluronate co-migrated with mRNA (2, 5) resulting in smeared bands instead of the sharp band observed for naked mRNA (1, 8). The naked mRNA kept at 40° C. (8) started degrading after 48 h as denoted by blurred and fuzzy band. Similarly, the mRNA embedded into the hydrogel and stored at 40° C. (5) showed a weaker signal after 48 h suggesting some level of degradation of mRNA. For the mRNA-delivery system-biodegradable gel formulations (3, 4, 6, 7), there was some leakage of the hyaluronate from the wells into the agarose gel in the areas in vicinity of the wells. However, the short travelled distance in the gel suggests lack of any mRNA release from the biodegradable gels.

Figure 3:
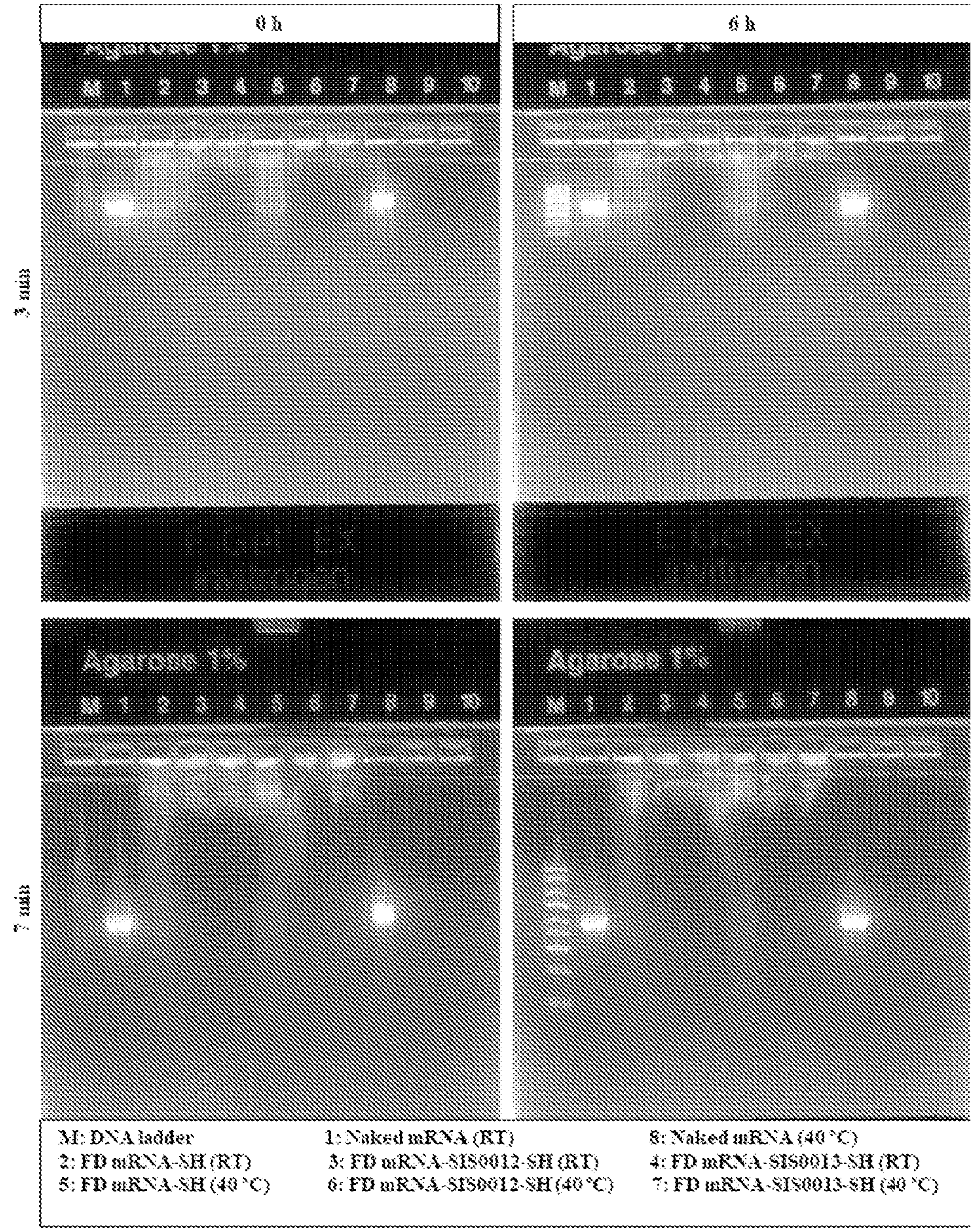
FIG. 3 Gel electrophoresis images of freeze-dried and reconstructed mRNA-Biocourier formulations embedded in sodium hyaluronate biodegradable gels at the time of preparation and 6 h after storage at room temperature (RT) or 40° C.
Figure 4:
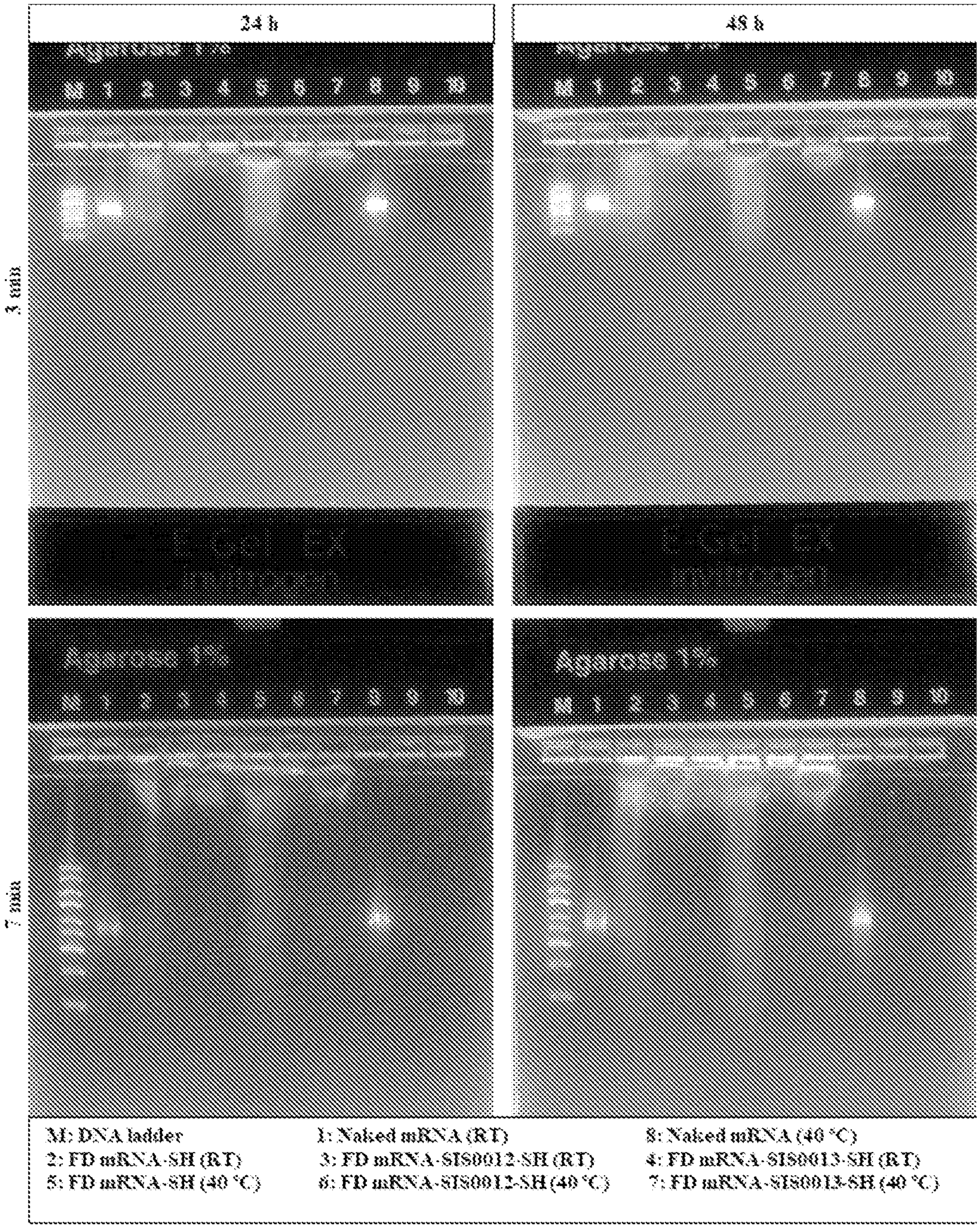
FIG. 4 Gel electrophoresis images of freeze-dried and reconstructed mRNA-Biocourier formulations embedded in sodium hyaluronate biodegradable gels 24 and 48 h after storage at room temperature (RT) or 40° C.

Test 2: Stability of the Freeze-Dried and Reconstituted mRNA-Delivery System Complexes The agarose gel electrophoresis images of the freeze-dried and reconstituted mRNA-delivery system formulations embedded in sodium hyaluronate hydrogel shortly after preparation and up to 48 h after storage at either room temperature or 40° C., are provided in FIGS. 3 and 4. FIG. 3 provides gel electrophoresis images of freeze-dried and reconstructed mRNA-Delivery System formulations embedded in sodium hyaluronate (SH) hydrogels (3, 4, 6, 7) at the time of preparation and 6 h after storage at room temperature (RT) or 40° C. FIG. 4 provides gel electrophoresis images of freeze-dried and reconstituted mRNA-delivery system formulations embedded in sodium hyaluronate (SH) hydrogels (3, 4, 6, 7) 24 and 48 h after storage at room temperature (RT) or 40° C. Naked mRNA (1, 8) and freeze-dried, reconstituted mRNA embedded in hydrogel (2, 5) were used as controls.

Similar to what was observed for the liquid mRNA-delivery system formulations of FIGS. 1 and 2, the freeze-dried and reconstructed mRNA-delivery system formulations embedded in hydrogels (3, 4, 6, 7) stopped the migration of mRNA through the agarose gel and were stable for up to 48 h both at room temperature and at 40° C. whereas the freeze-dried and reconstituted mRNA merely loaded on the hydrogels (2, 5) passed through the gel indicating lack of any complexation between the hydrogel and the mRNA. It can be inferred from these data that the mRNA-delivery system formulations (3, 4, 6, 7) are stable during and after the freeze-drying process and it does not compromise their association or stability.

Example 2

Evaluating the Stability of siRNA Loaded on Delivery Systems and Embedded into Sodium Hyaluronate (2% w/w) Hydrogels Following Storage at Room Temperature or at 40° C. Using Agarose Gel Electrophoresis Preparation of siRNA-Delivery System Complexes The siGLO™ Green stock solution was prepared by dissolving 50 nMol (0.66 mg) siRNA powder in 1 mL nuclease free water.

The sodium hyaluronate biodegradable gels were prepared by dissolving the powders in nuclease free water to give a concentration of 2% w/w.

The siRNA-delivery system complexes were prepared by mixing 4.5 μL of siGLO™ Green stock solution (equal to 3 μg of siRNA) with 23 μL of SIS0012, SIS0013 and MVI0010 Delivery System solutions (i.e., lipid to siRNA weight ratio of 12), and incubated at room temperature to ensure complete complexation. Subsequently, the siGLO-delivery system complexes were freeze-dried overnight. The lyophilized powder was then dissolved in 3 μL of nuclease-free water and embedded into 23 μL of sodium hyaluronate (SH) biodegradable gel. A formulation of siGLO-MVI0010 was also used without freeze-drying and without loading on the biodegradable gel.

All formulations were prepared as 25 μL aliquots (per analysis time point) and stored either at room temperature or in a water bath set to 40° C. for up to 48 h to be analyzed by gel electrophoresis. The amounts of siGLO-delivery system-biodegradable gel formulations, naked siGLO and DNA ladder used for gel retardation assay and total amount of siRNA/DNA per well are shown in Table 2:

TABLE 2

| Type of sample | Amount of sample (μL) | Amount of NFW (μL) | Amount of siRNA/DNA (μg/well) |
|---|---|---|---|
| siGLO-SIS0012-SH | 20 | — | 2.3 |
| siGLO-SIS0013-SH | 20 | — | 2.3 |
| siGLO-MVI0010-SH | 20 | — | 2.3 |
| siGLO-MVI0010 | 20 | — | 2.2 |
| Naked siGLO | 4 | 16 | 0.4 |
| DNA ladder | 2 | 18 | 0.2 |

Agarose Gel Electrophoresis

At designated time points (0, 6, 24, and 48 h) the samples were analyzed by agarose gel electrophoresis using the E-Gel™ Power Snap lectrophoresis device and E-Gel™ agarose (1%) gels. The samples, naked siGLO and DNA-ladder were loaded on the gel at a volume of 20 μL/well. The naked siRNA and the DNA ladder were diluted with nuclease-free water (NFW) prior to loading ion the agarose gel according to Table 1, but the formulations were used without any dilution. The gel was imaged after 3 min and 7 min using E-Gel™ Power Snap electrophoresis camera.

Figure 5:
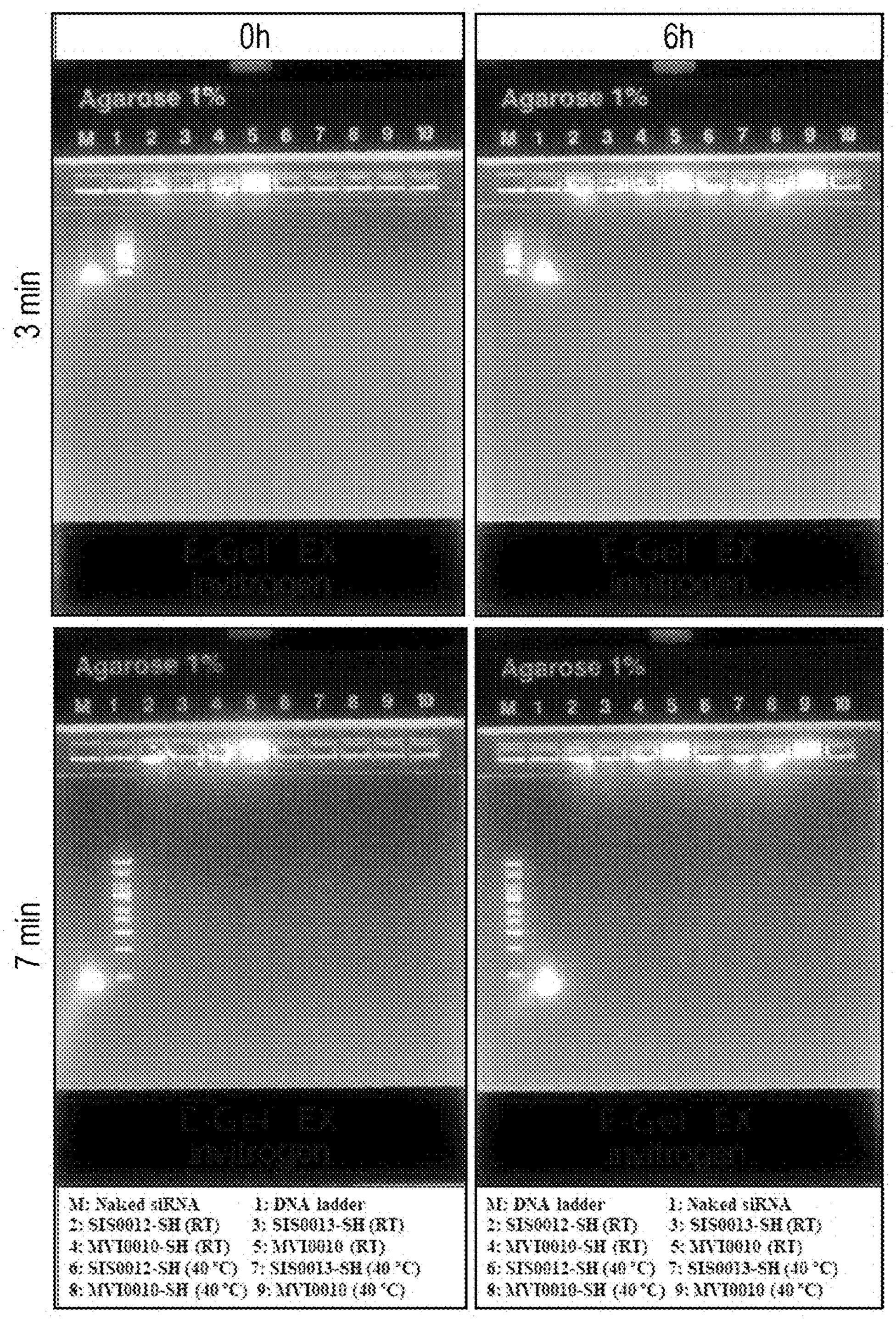
FIG. 5 Gel retardation images of siRNA-Biocourier-biodegradable gel formulations right after preparation and 2 h after storage at room temperature (RT) or 40° C.
Figure 6:
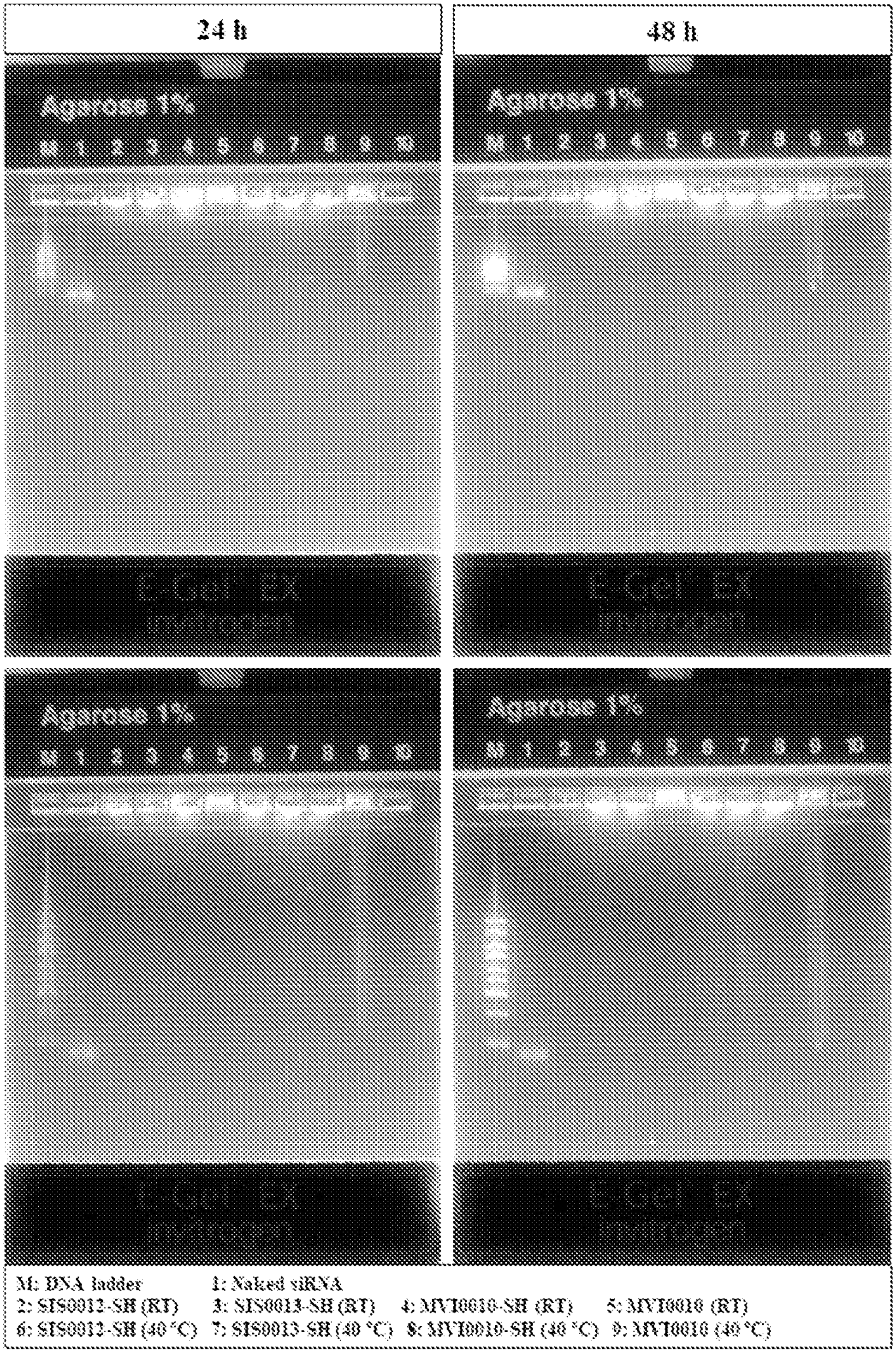
FIG. 6 Gel retardation images of siRNA-Biocourier-biodegradable gel formulations 24-48 h after storage at room temperature (RT) or 40° C.

Test 3: Stability of the Freeze-Dried and Reconstructed siRNA-Delivery System Complexes The gel electrophoresis images of siRNA-delivery system-biodegradable gel formulations loaded with stored at room temperature or 40° C. are presented in FIGS. 5 and 6.

As it could be observed, all formulations complexed the siRNA efficiently and stopped its migration through the gel. The complexes were stable both at room temperature and at 40° C. for 6 h as indicated by lack of any siRNA passing through the gel. However, after 24 h significant amount of siRNA was released into the gel by the MVI0010 formulation in the liquid from stored at 40° C. (9) which indicates lack of stability of this formulation at high temperature. On the other hand, for the siRNA-SIS0012 and SIS0013 formulations embedded into the biodegradable gel (6, 7) only small traces of siRNA were observed passing through the gel after 48 h storage at 40° C. which was slightly higher for SIS0013-biodegradable gel formulation (7) compared to SIS0012-biodegradable gel (6) and MVI0010-biodegradable gel (8) formulations. As it could be inferred from these data, the siRNA-Delivery System formulations embedded into sodium hyaluronate biodegradable gel were stable for 48 hours both at room temperature (2, 3, 4) and at 40° C. (6, 7, 8) whereas siRNA-MVI0010 formulation in the liquid form (5, 9) was only stable at room temperature (5) and at 40° C. (9) it started releasing the siRNA from 24 h. These findings suggest the role of the biodegradable gel matrix in stabilizing the siRNA-delivery system complexes especially at higher temperatures.

Conclusions

Mixing the siRNA-Delivery System complexes with highly concentrated sodium hyaluronate hydrogel resulted in stability at room temperature and 40° C. for 48 h. The siRNA-MVI0010 complexes which were not mixed with hydrogel (5, 9) were stable for 48 h at room temperature (5) but less than 24 h at 40° C. (9) indicating the role of the sodium hyaluronate hydrogel in stabilizing the siRNA-MVI0010 complexes.

Example 3

Evaluating the Stability of siRNA Loaded on Delivery System Formulations SIS0012 and SIS0013 Embedded into Sodium Hyaluronate (2% w/w) or Hypromellose (4% w/w) Hydrogels Following Storage at Room Temperature or at 40° C. Using Agarose Gel Electrophoresis Preparation of the siRNA-Delivery System-Biodegradable Gel Formulations The ADO2-siRNA (with dTdT overhangs) and siGLO™ Green stock solutions were prepared by dissolving siRNA powder in nuclease free DI water according to Table 1. 250 nMol (33.33 mg) ADO2 siRNA is dissolved in 0.5 mL of water to give a 6.66 mg/mL solution and further diluted with water to a 1 μg/μL or 66.5 ng/μL solution. 50 nMol (0.66 mg) siGLO™ Green siRNA is dissolved in 1 mL water to give a 0.66 mg/mL solution and then further diluted with water to a 66.5 ng/μL solution.

The sodium hyaluronate and hypromellose hydrogels were prepared by dissolving the powders in nuclease free water to give concentrations of 2% and 4% w/w respectively.

The siRNA-delivery system-hydrogel formulations were prepared keeping the lipid/siRNA weight ratio constant at 12. The amounts of siRNA, delivery system and hydrogel used for preparation of the different formulations are provided in Table 3. The formulations were prepared in small aliquots (32-33 μL for the formulations containing ADO2 siRNA and siGLO™ Green respectively) and stored either in room temperature or in a water bath at 40° C. for up to 48 h.

TABLE 3

| Formulation | Amount of Delivery System (μL) | Amount of bio-degradable gel (μL) | Amount of siRNA (μg) | Final concentration of siRNA (ng/μL) |
|---|---|---|---|---|
| ADO2-SIS0012-SH | 15 | 15 | 2 | 62.5 |
| ADO2-SIS0012-HY | 15 | 15 | 2 | 62.5 |
| ADO2-SIS0012 | 15 | — | 2 | 117.6 |
| ADO2-SIS0013-SH | 15 | 15 | 2 | 62.5 |
| ADO2-SIS0013-HY | 15 | 15 | 2 | 62.5 |
| ADO2-SIS0013 | 15 | — | 2 | 117.6 |
| ADO2-SH | — | 15 | 1 | 62.5 |
| ADO2-HY | — | 15 | 1 | 62.5 |
| siGLO-SIS0012-SH | 15 | 15 | 2 | 60.6 |
| siGLO-SIS0012-HY | 15 | 15 | 2 | 60.6 |
| siGLO-SIS0012 | 15 | — | 2 | 111.1 |
| siGLO-SIS0013-SH | 15 | 15 | 2 | 60.6 |
| siGLO-SIS0013-HY | 15 | 15 | 2 | 60.6 |
| siGLO-SIS0013 | 15 | — | 2 | 111.1 |
| siGLO-SH | — | 15 | 1 | 60.6 |
| siGLO-HY | — | 15 | 1 | 60.6 |

Agarose Gel Electrophoresis

At designated time points (0, 2, 4, 6, 24, and 48 h) the formulations were analysed by agarose gel electrophoresis. The gel electrophoresis system used for these experiments consists of a gel electrophoresis device, precast agarose gels (1%, with running buffer and electrode provided within the gel) and a camera. The samples, control (naked siRNA), and DNA ladder were mixed with the required amount of the gel loading buffer to make a total volume of 20 μL according to Table 8 prior to loading onto the gel. Subsequently, the gel was inserted into the device chamber, loaded with the samples, control and DNA ladder, and ran for 7 min. The gel was transilluminated and imaged at 3 min and 7 min using the camera.

TABLE 4

| Type of sample | Amount of sample (μL) | Amount of loading buffer (μL) | Amount of siRNA (μg/well) |
|---|---|---|---|
| ADO2-SIS0012-SH | 10 | 10 | 0.62 |
| ADO2-SIS0012-HY | 10 | 10 | 0.62 |
| ADO2-SIS0013-SH | 10 | 10 | 0.62 |
| ADO2-SIS0013-HY | 10 | 10 | 0.62 |
| siGLO-SIS0012-SH | 10 | 10 | 0.61 |
| siGLO-SIS0012-HY | 10 | 10 | 0.61 |
| siGLO-SIS0013-SH | 10 | 10 | 0.61 |
| siGLO-SIS0013-HY | 10 | 10 | 0.61 |
| ADO2-SIS0012 | 10 | 10 | 1.2 |
| ADO2-SIS0013 | 10 | 10 | 1.2 |
| siGLO-SIS0012 | 10 | 10 | 1.1 |
| siGLO-SIS0013 | 10 | 10 | 1.1 |
| ADO2-SH | 10 | 10 | 0.62 |
| ADO2-HY | 10 | 10 | 0.62 |
| siGLO-SH | 10 | 10 | 0.61 |
| siGLO-HY | 10 | 10 | 0.61 |
| Naked ADO2 | 3 | 17 | 0.2 |
| Naked siGLO | 3 | 17 | 0.2 |
| DNA ladder | 2 | 18 | 0.2 |

Test 4: Stability of SIS0012 Formulations Loaded with siRNA

Figure 7:
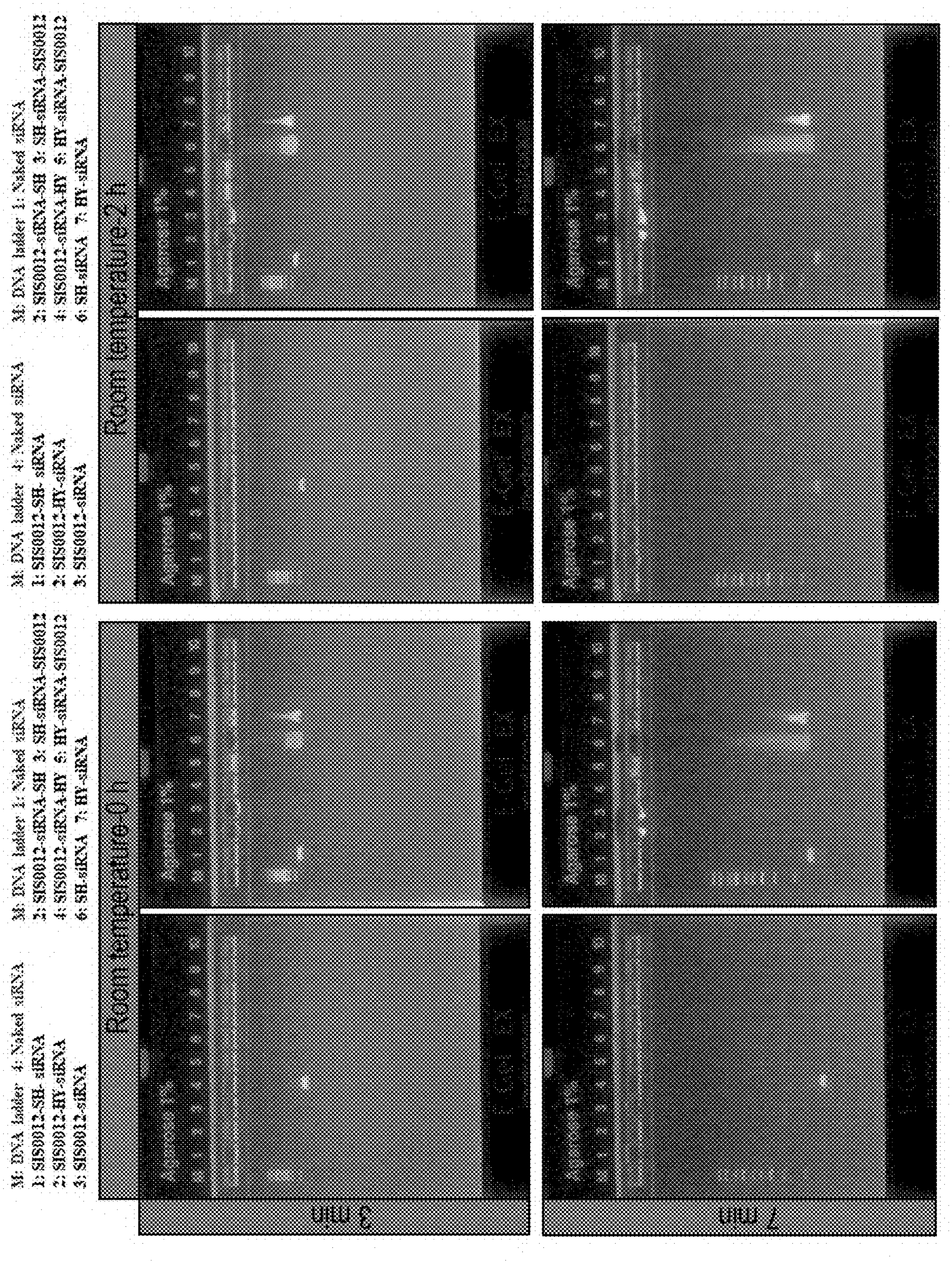
FIG. 7 Gel electrophoresis images of siRNA-SIS0012-biodegradable gel formulations right after preparation (0 h) and 2 h after storage at room temperature.
Figure 8:
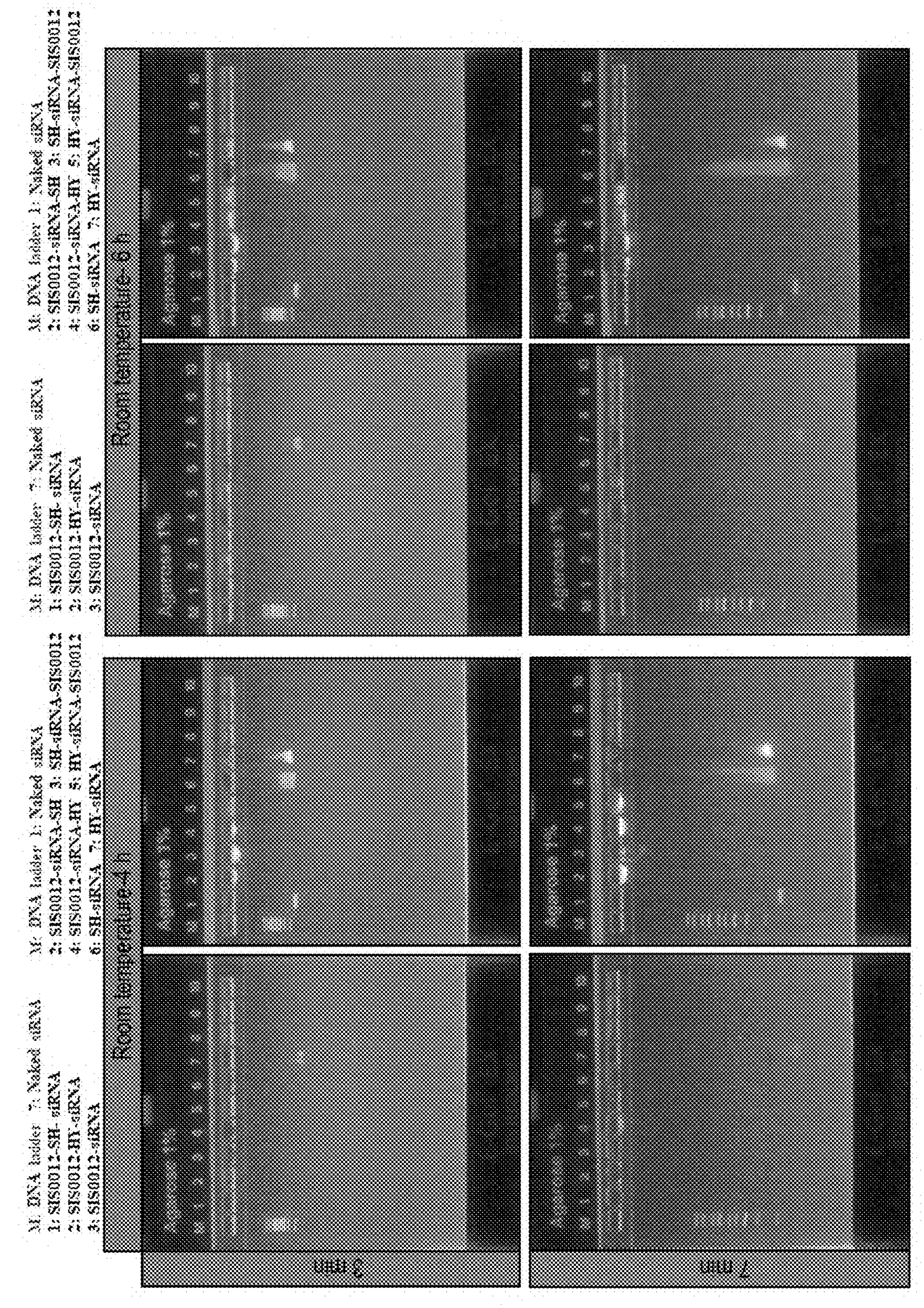
FIG. 8 Gel electrophoresis images of siRNA-SIS0012-biodegradable gel formulations 4-6 h after storage at room temperature.
Figure 9:
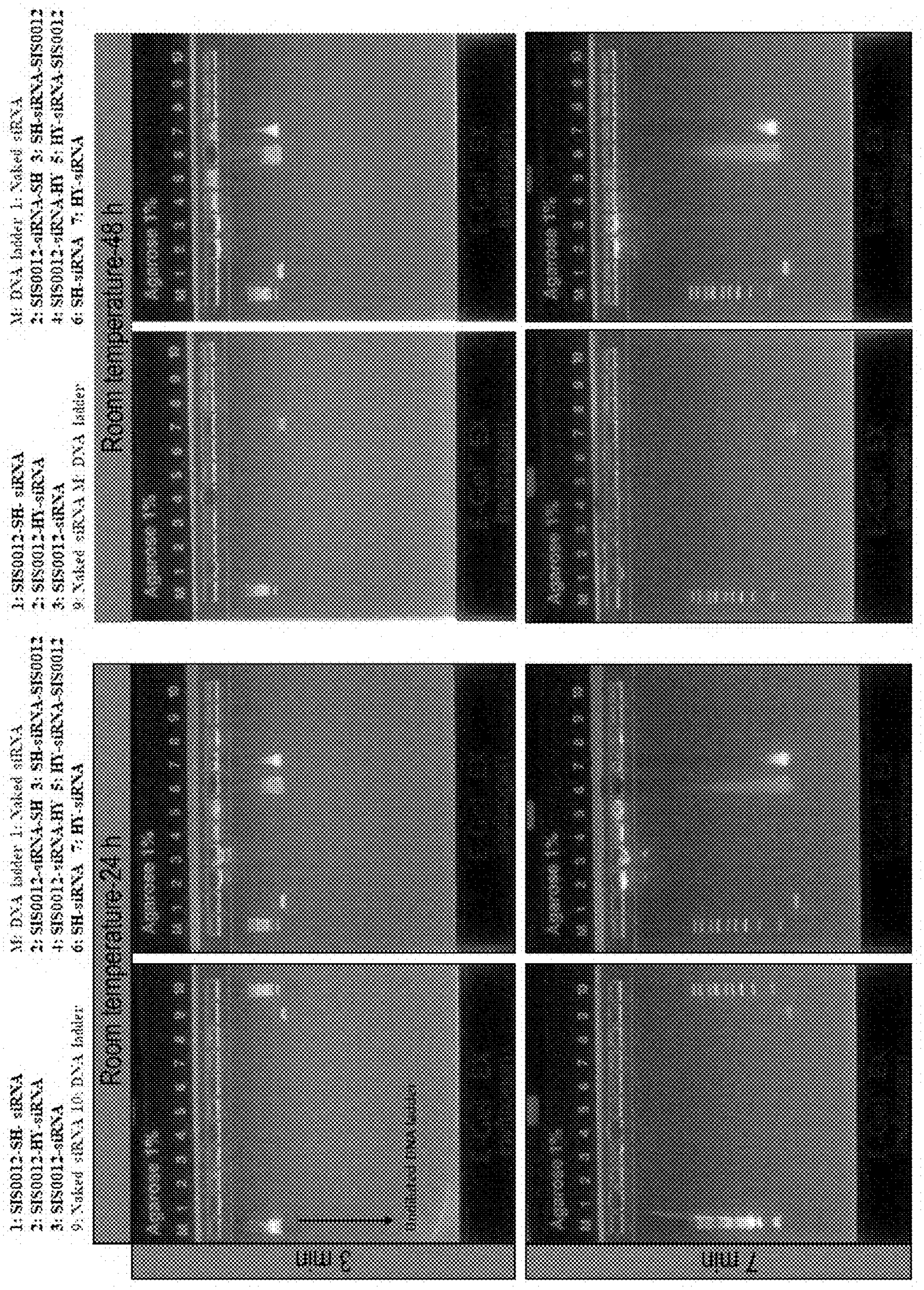
FIG. 9 Gel electrophoresis images of siRNA-SIS0012-biodegradable gel formulations 24-48 h after storage at room temperature.

The gel electrophoresis images of SIS0012-biodegradable gel formulations loaded with ADO2-siRNA or siGLO™ green and stored at room temperature are depicted in FIGS. 7 to 9. As it could be observed, all the formulations complexed the loaded siRNA and stopped its migration through the gel regardless of the order of combination of the components (i.e., delivery system, biodegradable gel and siRNA). On the contrary, the siRNA loaded onto the biodegradable gels without any delivery system, which were used as negative controls, passed through the gel indicating lack of any binding between the siRNA and the biodegradable gels.

Nevertheless, a closer look at the images reveals that in the formulations in which siRNA was first mixed with sodium hyaluronate and then combined with SIS0012 the complexation was not complete, and a small fraction of siRNA passed through the gel. This is supposed to be caused by non-homogenous dispersion of siRNA in the biodegradable gel due to high viscosity of the sodium hyaluronate biodegradable gel. As a result, upon addition of the delivery system the siRNA cannot be completely mixed with the delivery system and the remaining siRNA which is not complexed will pass through the gel. This observation suggests that for efficient complexation of siRNA, either the delivery system should be mixed with the biodegradable gel prior to addition of the siRNA, or the delivery system should be mixed with the siRNA and then embedded within the biodegradable gel. The intensity of the siRNA bands for this particular formulation became considerably less after 48 h storage at room temperature suggesting degradation of the free/unbound siRNA.

As can be inferred from the images, there was no difference between the ADO-2 siRNA and siGLO™ green in terms of complexation and stability. It is also noteworthy that the two types of biodegradable gel behaved differently in terms of releasing the unbound siRNA into the agarose gel. The siRNA released from hypromellose appeared to have a smaller number of fragments whereas the siRNA released from sodium hyaluronate appeared as a mixture of fragments with different sizes. Also, presumably a proportion of hyaluronate may also migrate with the siRNA through the gel due to its negative charge.

Figure 10:
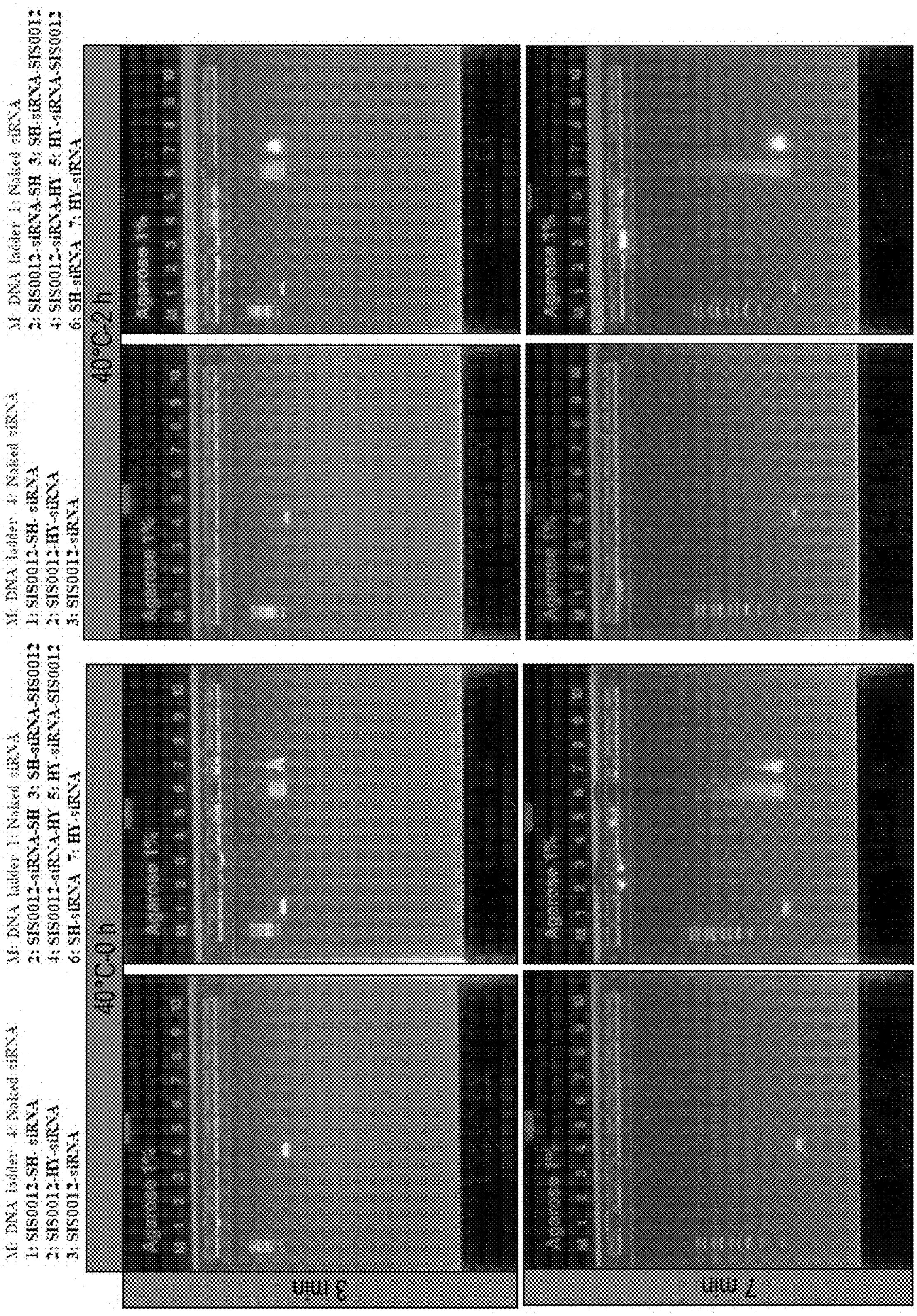
FIG. 10 Gel electrophoresis images of siRNA-SIS0012-biodegradable gel formulations right after preparation (0 h) and 2 h after storage at 40° C.
Figure 11:
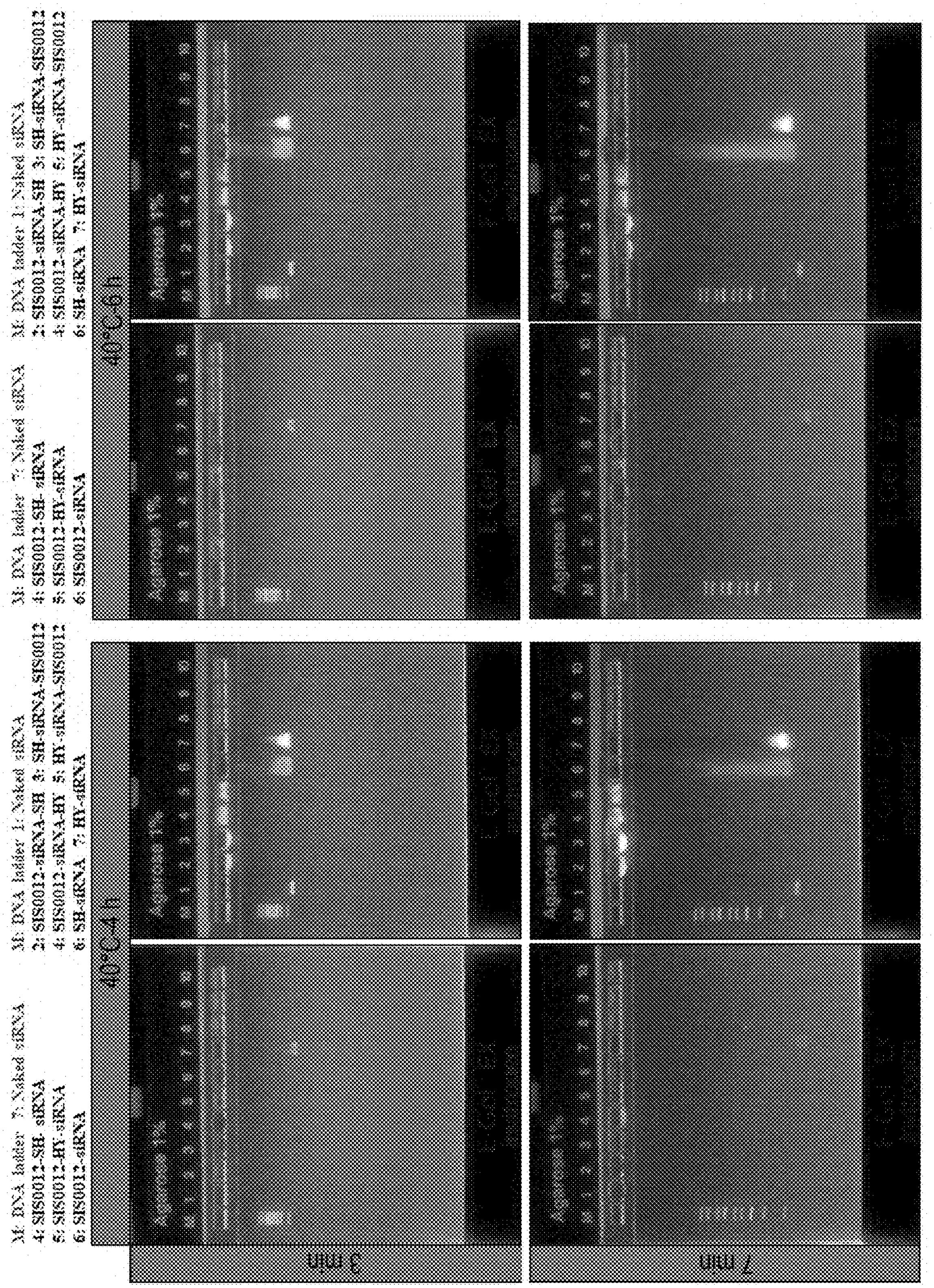
FIG. 11 Gel electrophoresis images of siRNA-SIS0012-biodegradable gel formulations 4-6 h after storage at 40° C.
Figure 12:
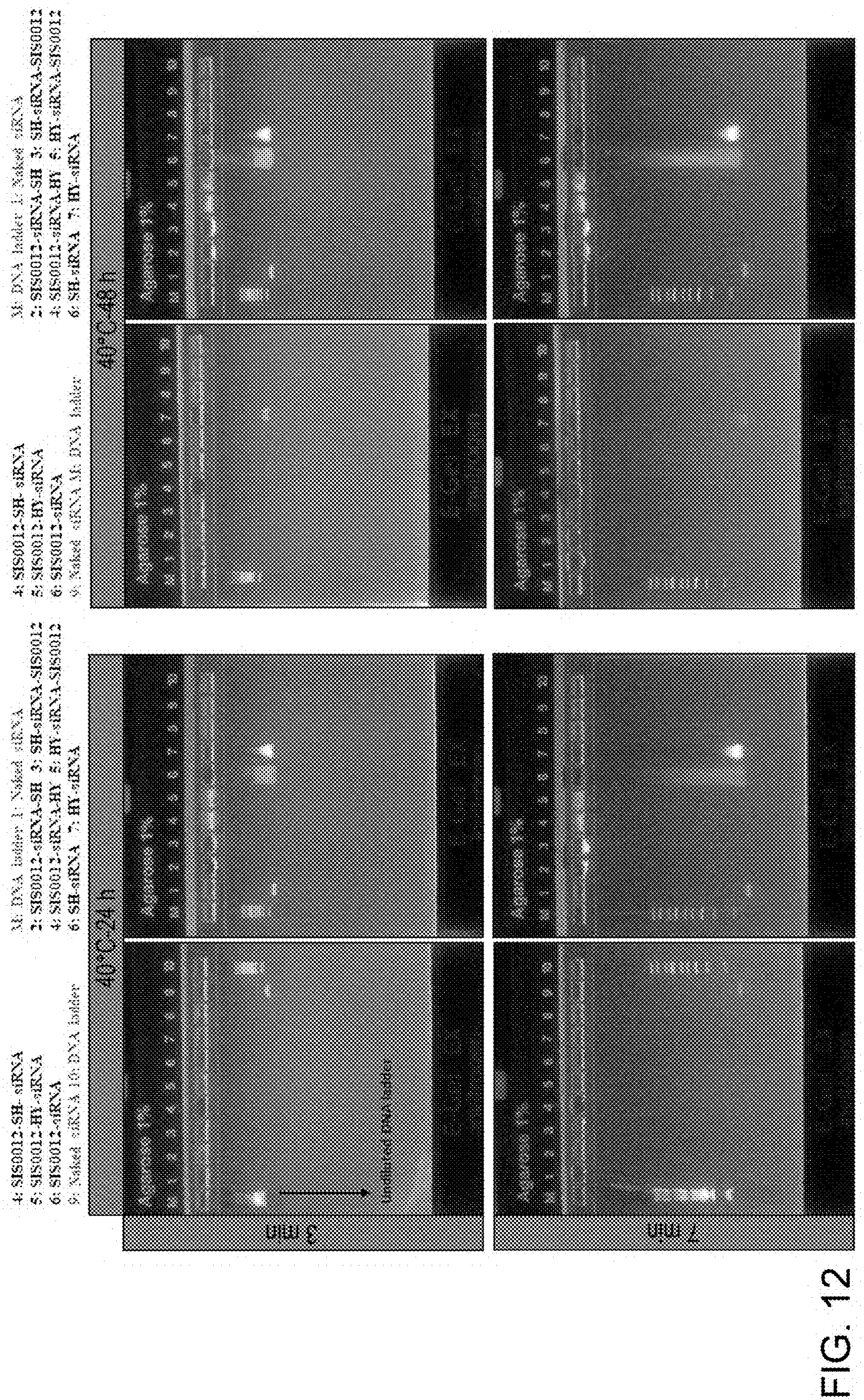
FIG. 12 Gel electrophoresis images of siRNA-SIS0012-biodegradable gel formulations 24-48 h after storage at 40° C.

The gel retardation images of the SIS0012-biodegradable gel-siRNA formulations stored at 40° C. are presented in FIGS. 10 to 12. As can be observed, the SIS0012-biodegradable gel-siRNA formulations stored at 40° C. behaved in a similar manner as the formulations stored at room temperature. Similarly, in the formulation where siRNA was first mixed with sodium hyaluronate and then combined with SIS0012, a fraction of siRNA passed through the gel indicating lack of efficient complexation resulting from no-homogenous dispersion of siRNA within the biodegradable gel. However, lack of the siRNA band for this formulation after 4 h suggests faster degradation of the unbound siRNA at 40° C.

Test 5: Stability of SIS0013 Formulations Loaded with siRNA

Figure 13:
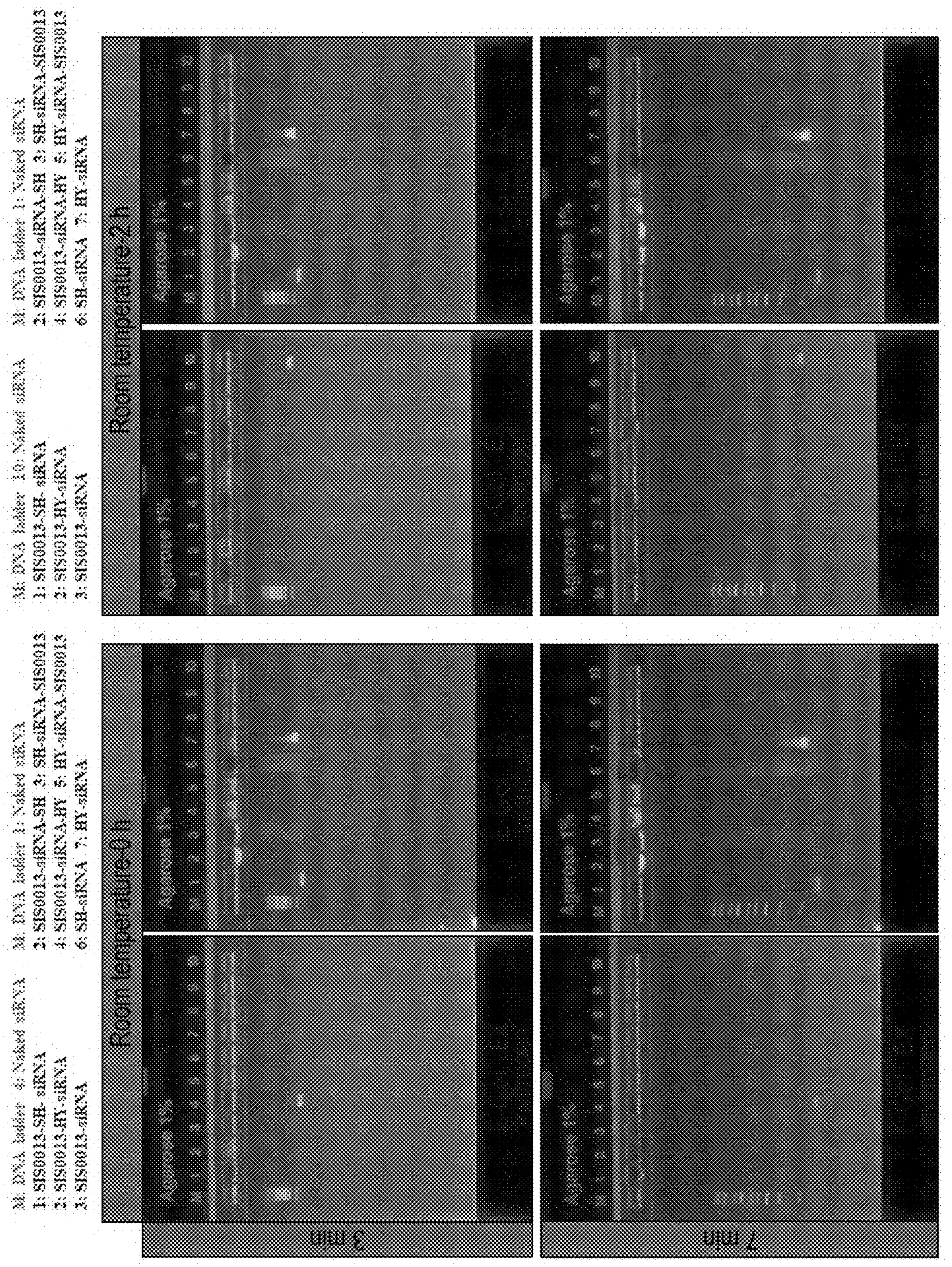
FIG. 13 Gel electrophoresis images of siRNA-SIS0013-biodegradable gel formulations right after preparation (0 h) and 2 h after storage at room temperature.
Figure 14:
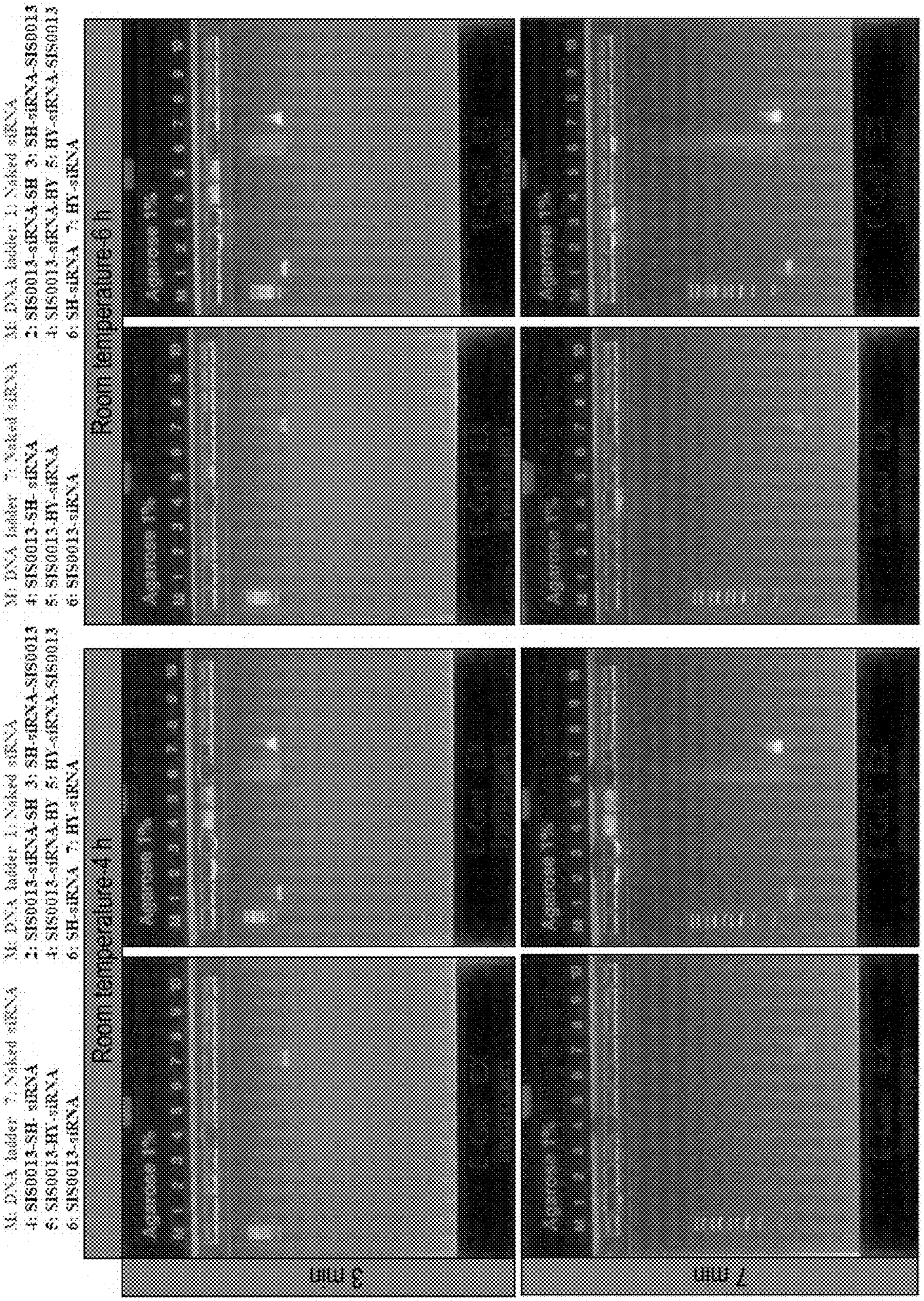
FIG. 14 Gel electrophoresis images of siRNA-SIS0013-biodegradable gel formulations 4-6 h after storage at room temperature.
Figure 15:
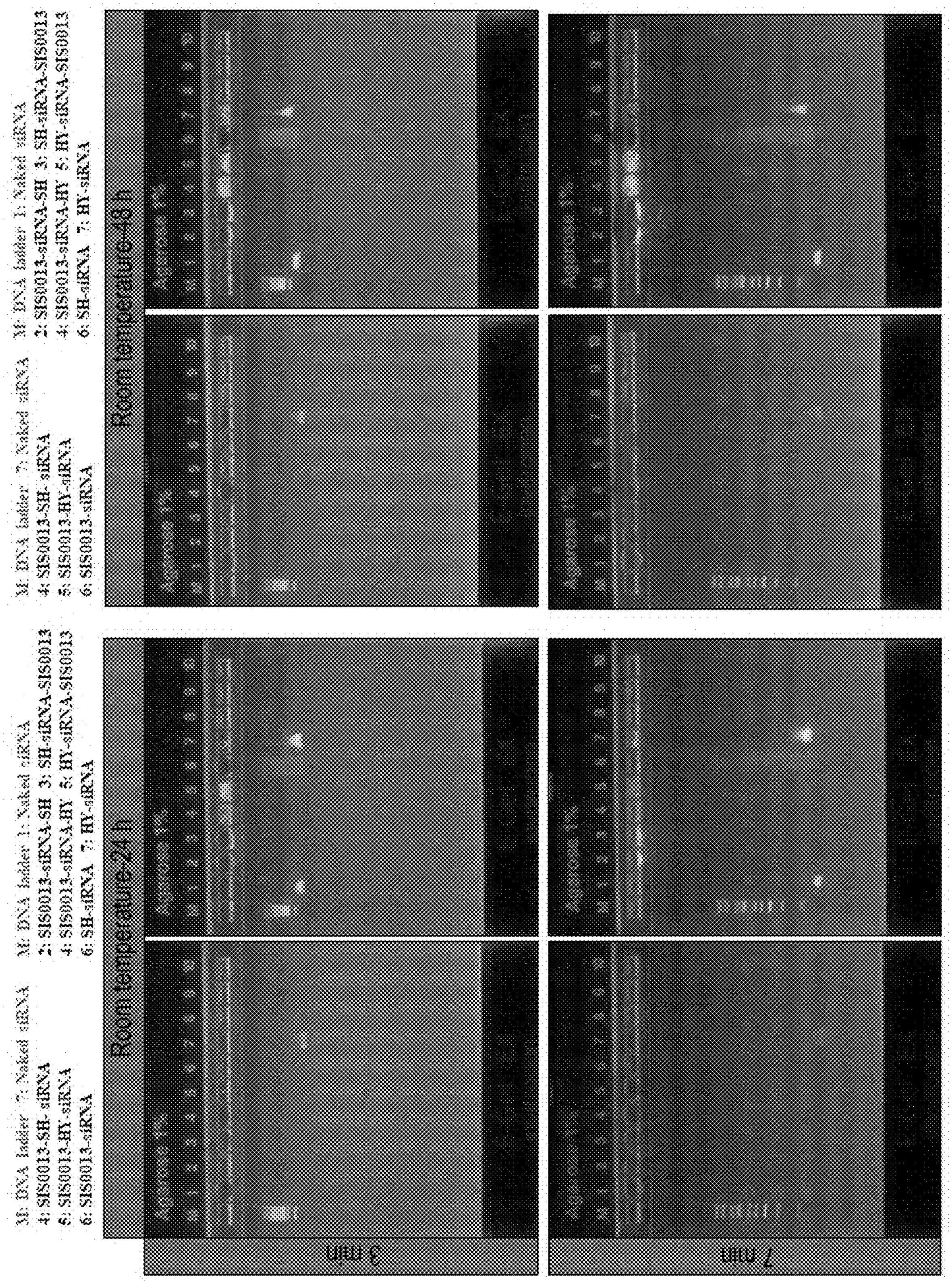
FIG. 15 Gel electrophoresis images of siRNA-SIS0013-biodegradable gel formulations 24-48 h after storage at room temperature.

The gel retardation images of SIS0013-biodegradable gel formulations loaded either with ADO-2 siRNA or with siGLO™ Green and stored at room temperature are provided in FIGS. 13 to 15. As it is evident from these figures, similar to what observed for siRNA-SIS0012-hyaluronate formulations, for siRNA-SIS0013-hyaluronate formulations also embedding the siRNA within the biodegradable gel prior to mixing with the delivery system results in inefficient complexation. The higher intensity of the siRNA band compared to what is observed for SIS0012 indicates larger fraction of unbound siRNA due to poor dispersion of siRNA within the biodegradable gel. This observation further confirms the previously mentioned deduction that for efficient complexation of siRNA, either the siRNA should be mixed with the delivery system first and then embedded into the biodegradable gel or the siRNA should be added to the homogenous mixture of the delivery system and the biodegradable gel. Once again, decreased intensity of the observed siRNA band for this formulation after 4-6 h and clearing of the band after 24 h indicates degradation of the unbound siRNA over time.

Figure 16:
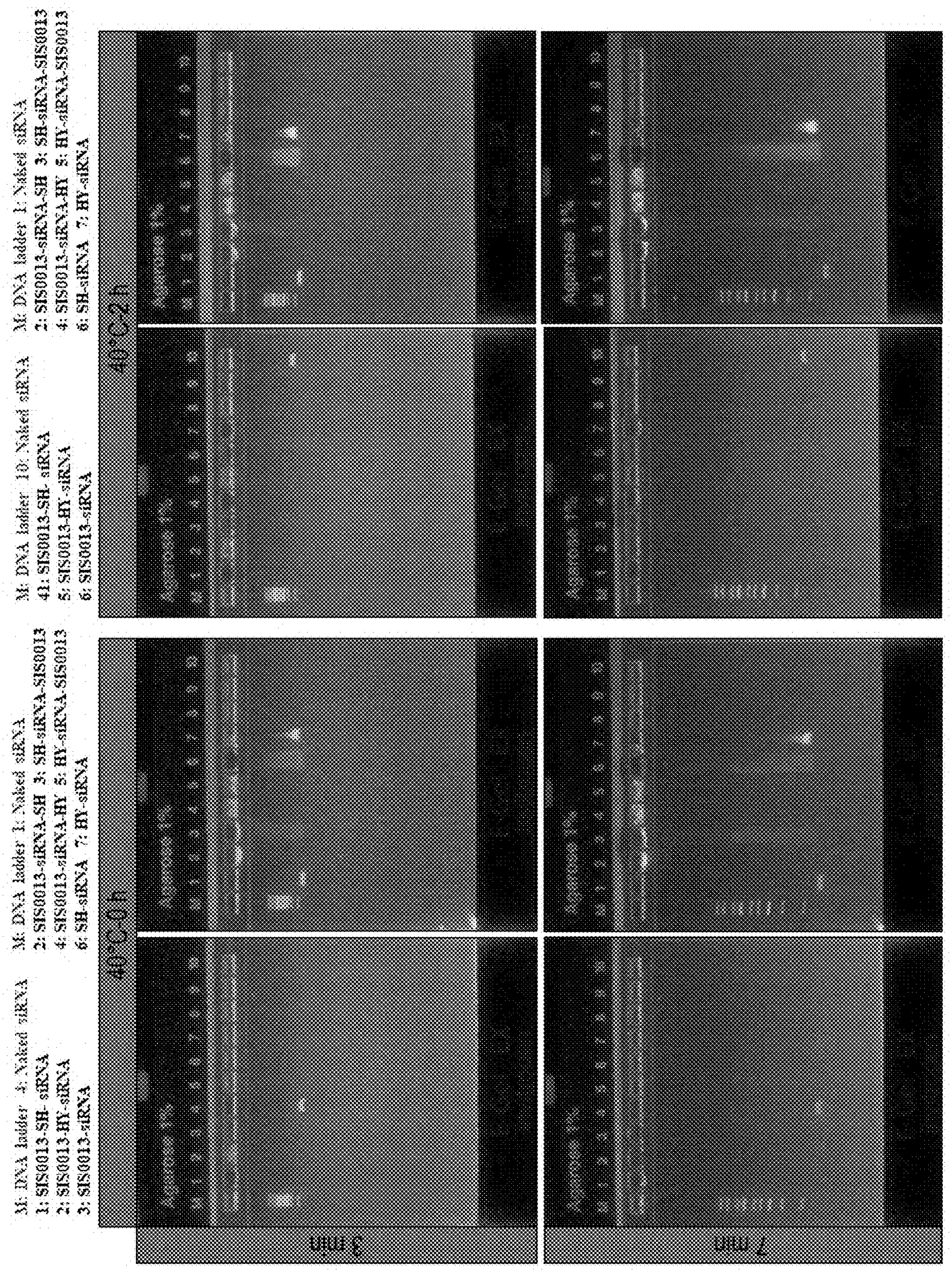
FIG. 16 Gel electrophoresis images of siRNA-SIS0013-biodegradable gel formulations immediately following preparation (0 h) and 2 h after storage at 40° C.
Figure 17:
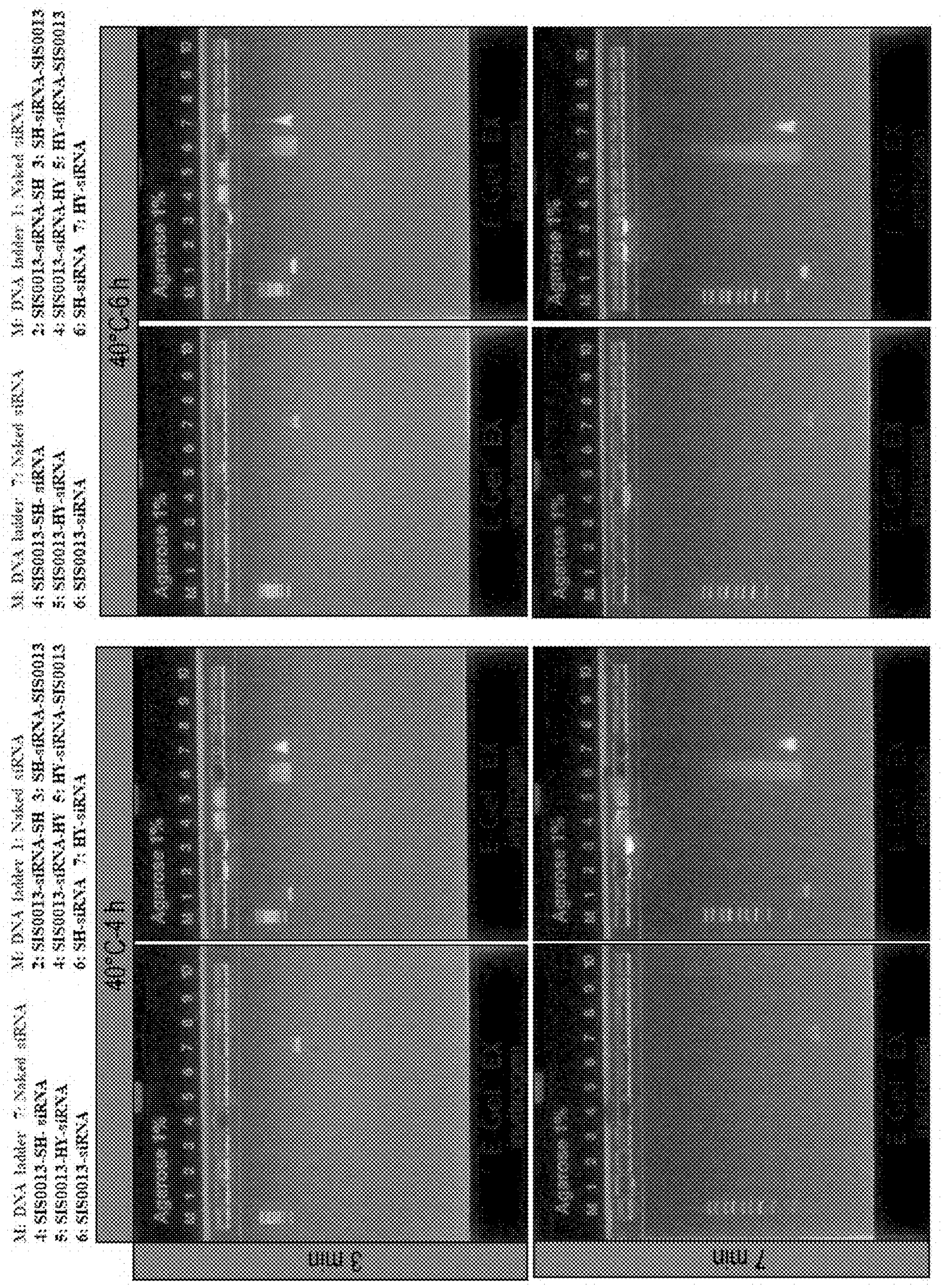
FIG. 17 Gel electrophoresis images of siRNA-SIS0013-biodegradable gel formulations 4-6 h after storage at 40° C.
Figure 18:
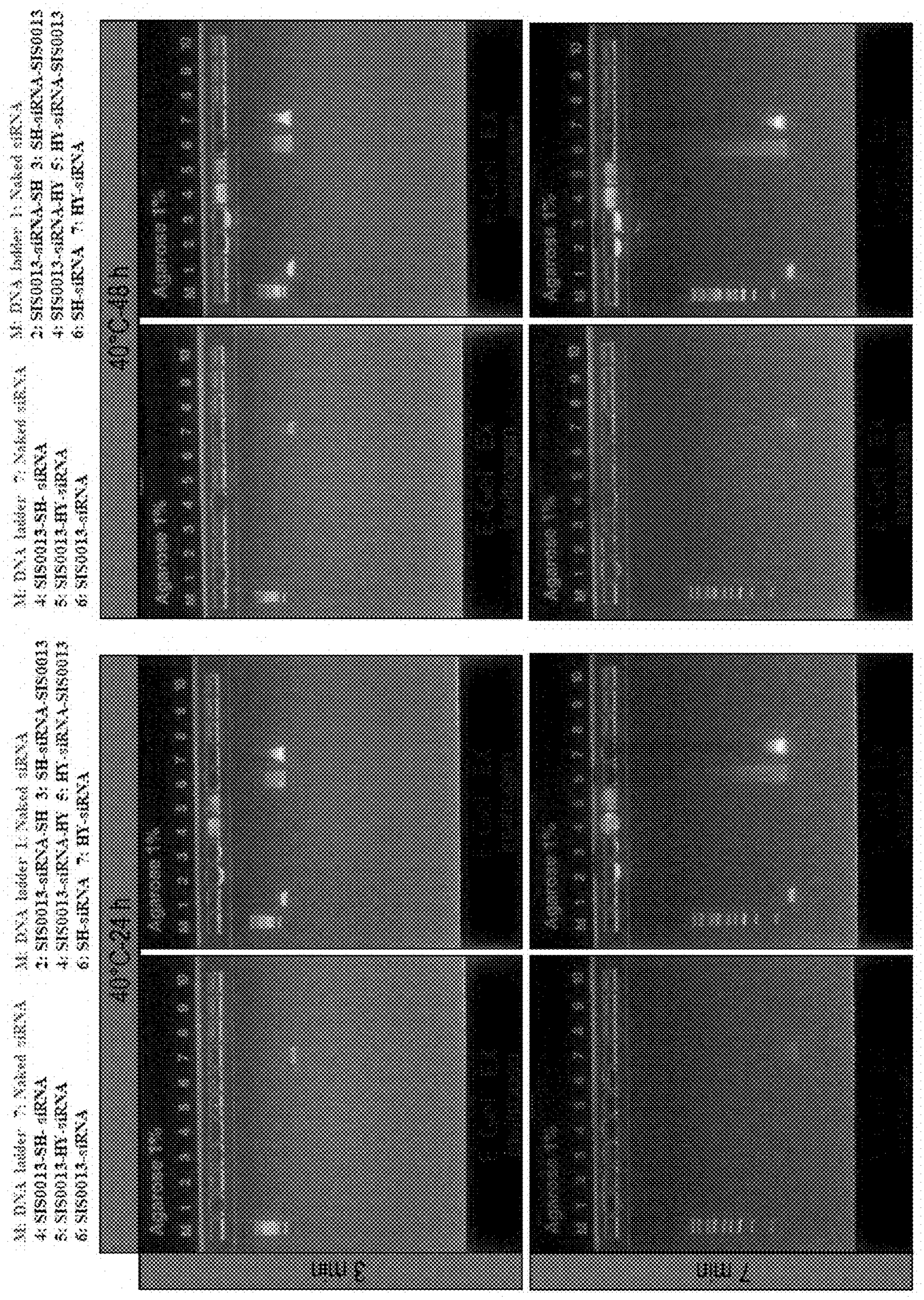
FIG. 18 Gel electrophoresis images of siRNA-SIS0013-biodegradable gel formulations 24-48 h after storage at 40° C.
Figure 19:
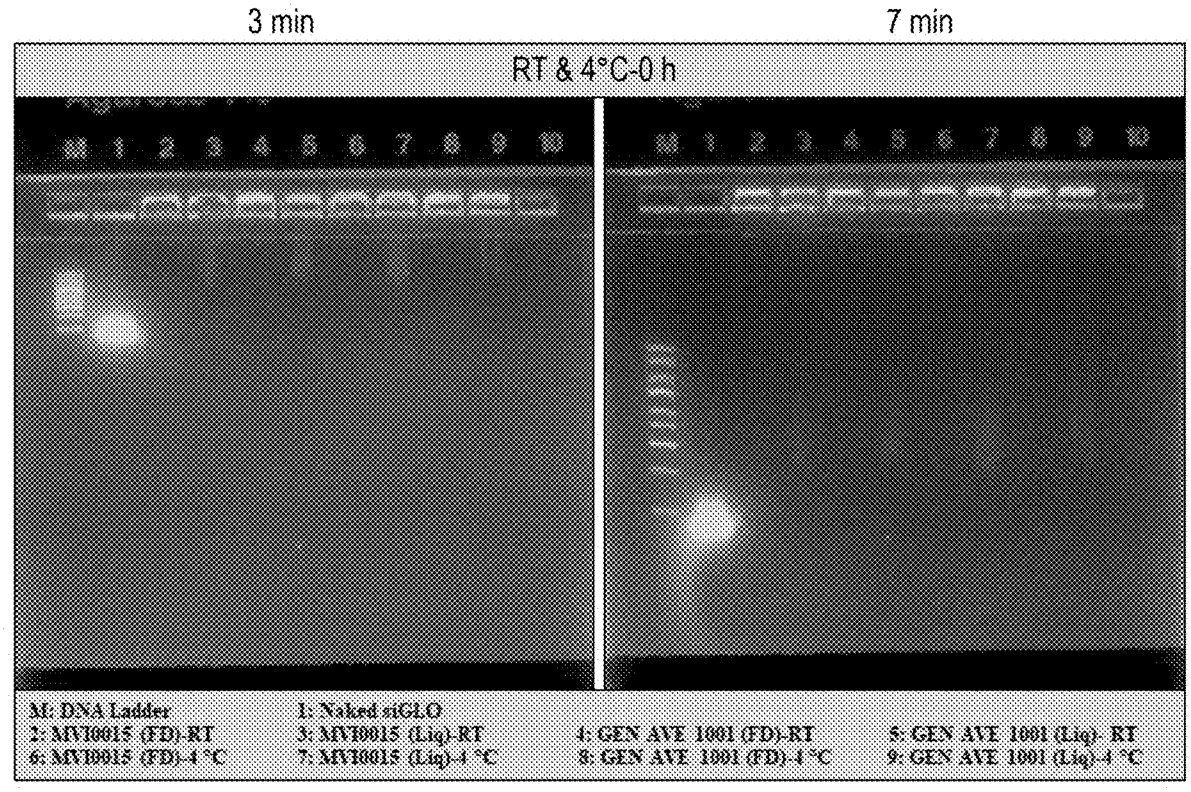
FIG. 19 Gel electrophoresis images of the siGLO-Delivery System complexes in the liquid form (Liq) or resuspended freeze-dried powder (FD) shortly after preparation.
Figure 20:
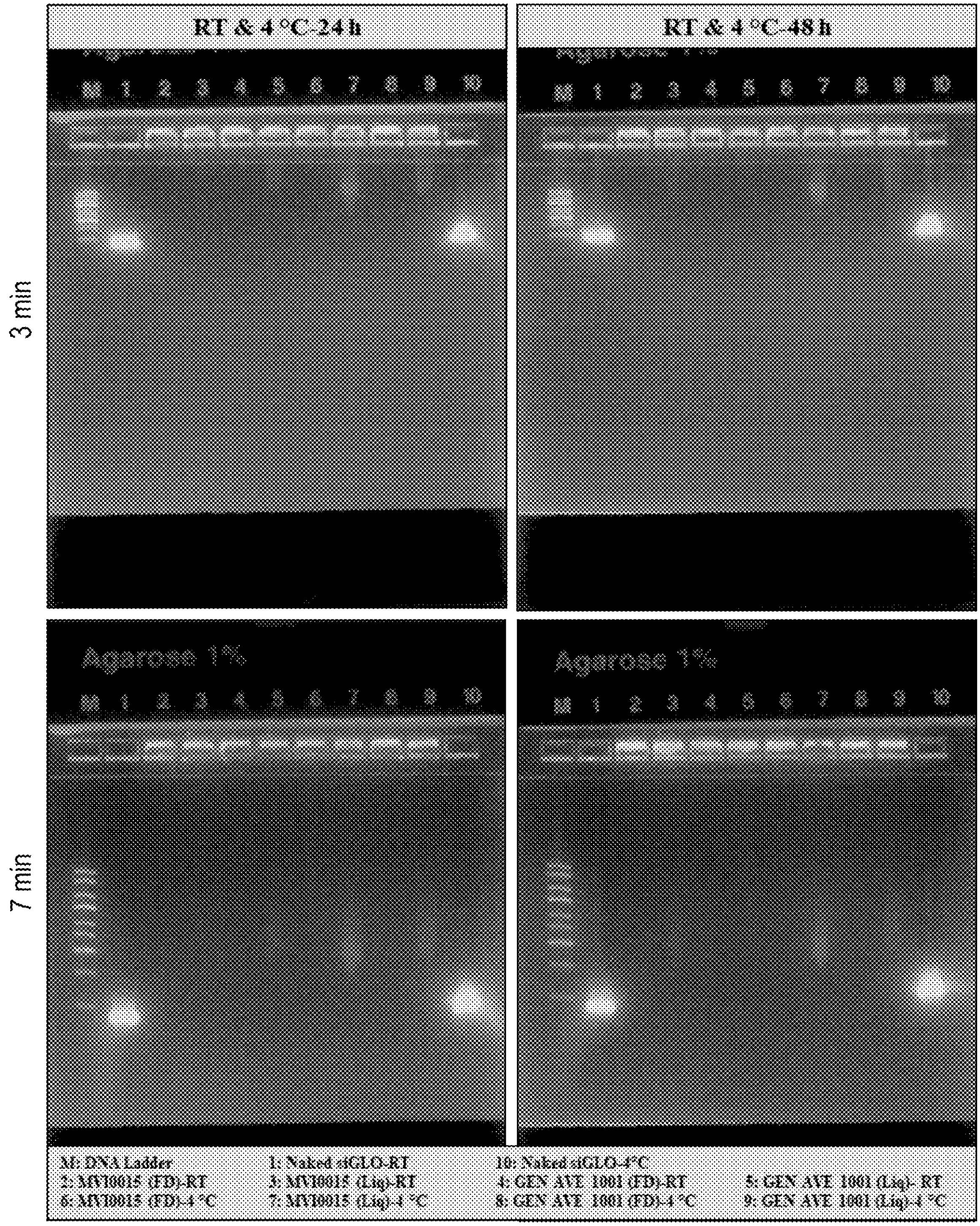
FIG. 20 Gel electrophoresis images of the siGLO-Delivery System complexes in the liquid form (Liq) or resuspended freeze-dried powder (FD) 24-48 h after storage at room temperature (RT) or 4° C.
Figure 21:
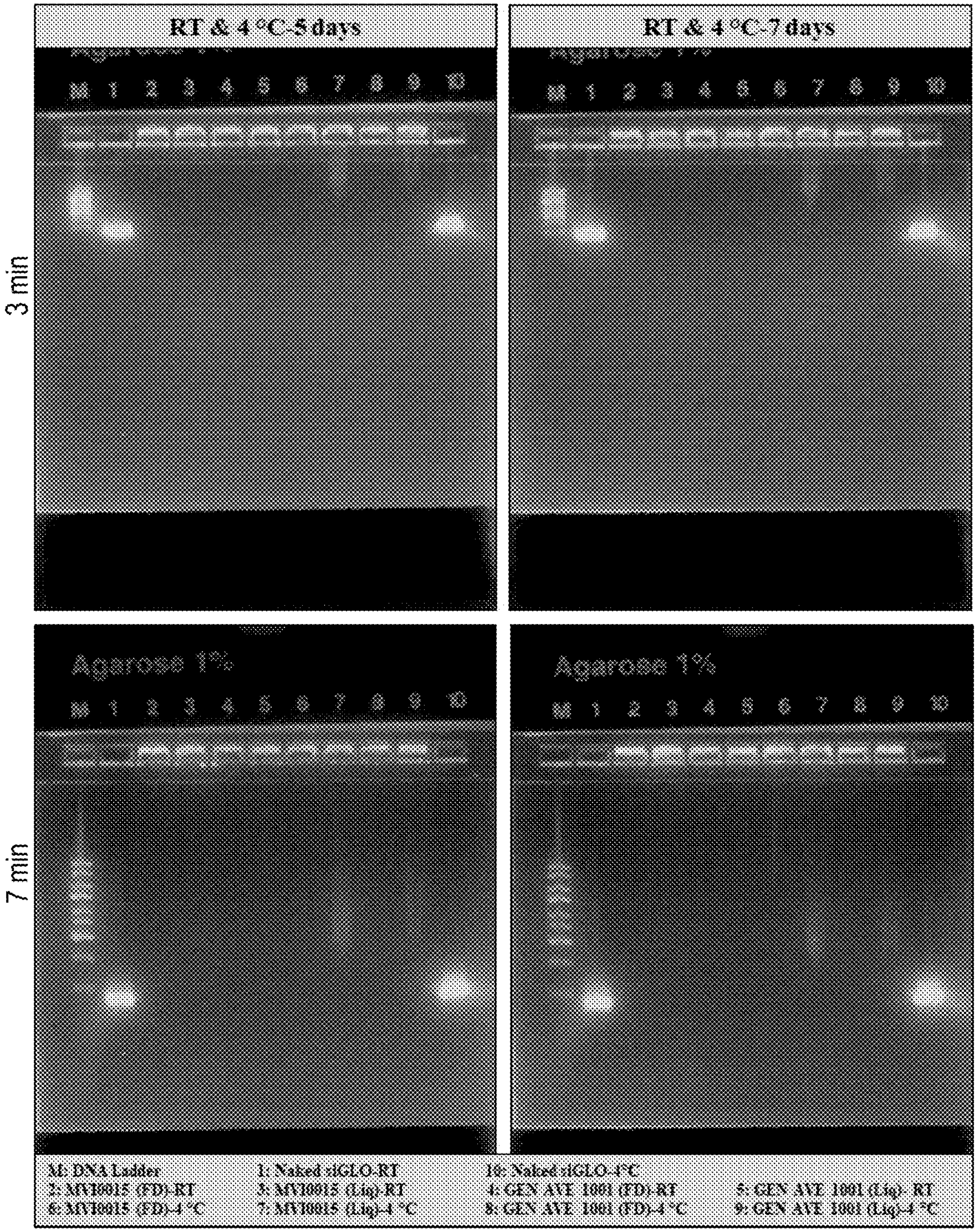
FIG. 21 Gel electrophoresis images of siGLO-Delivery System complexes in the liquid form (Liq) or resuspended freeze-dried powder (FD), 5 & 7 days after storage at room temperature (RT) or 4° C.
Figure 22:
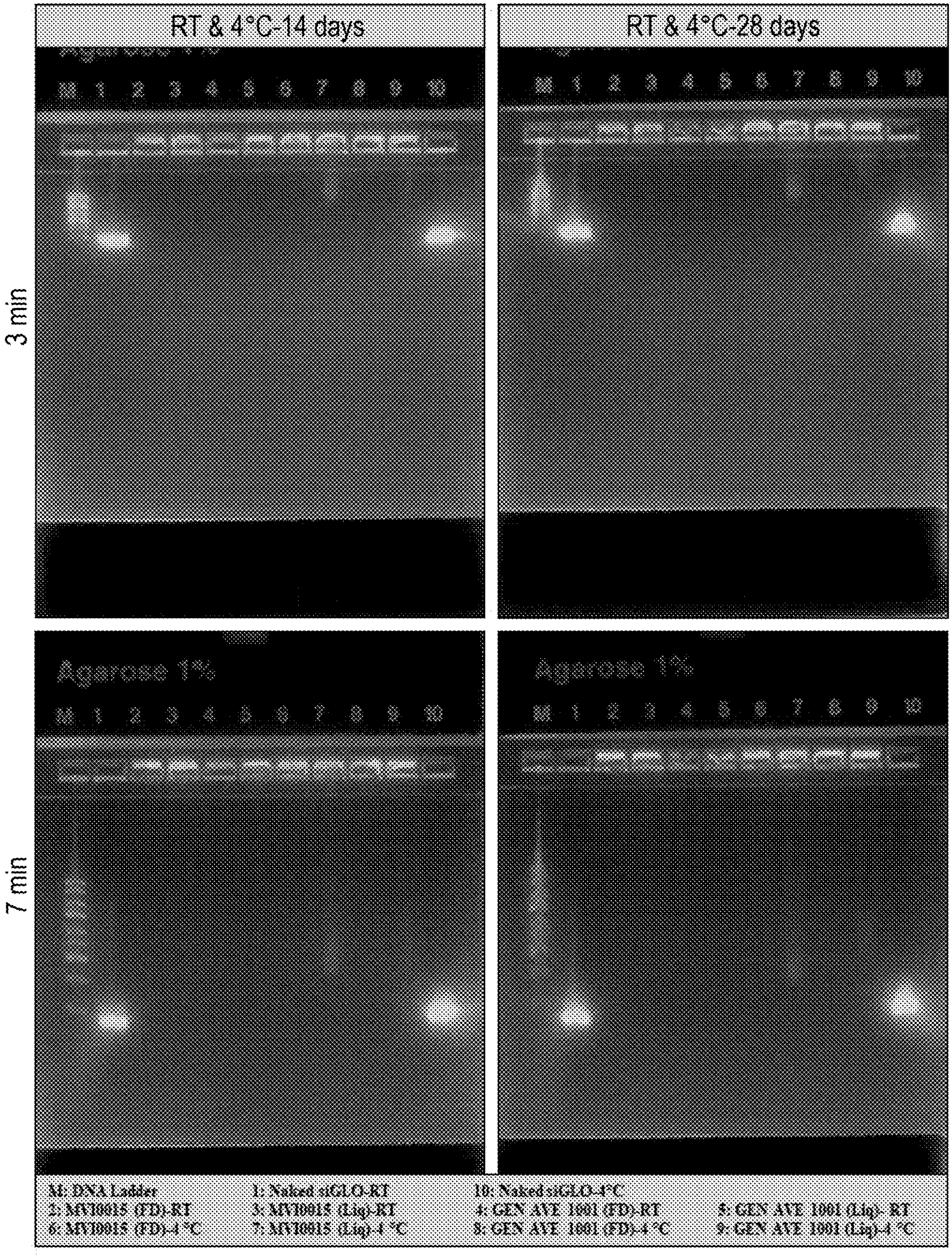
FIG. 22 Gel electrophoresis images of siGLO-Delivery System complexes in the liquid form (Liq) or resuspended freeze-dried powder (FD), 14 & 28 days after storage at room temperature (RT) or 4° C.
Figure 23:
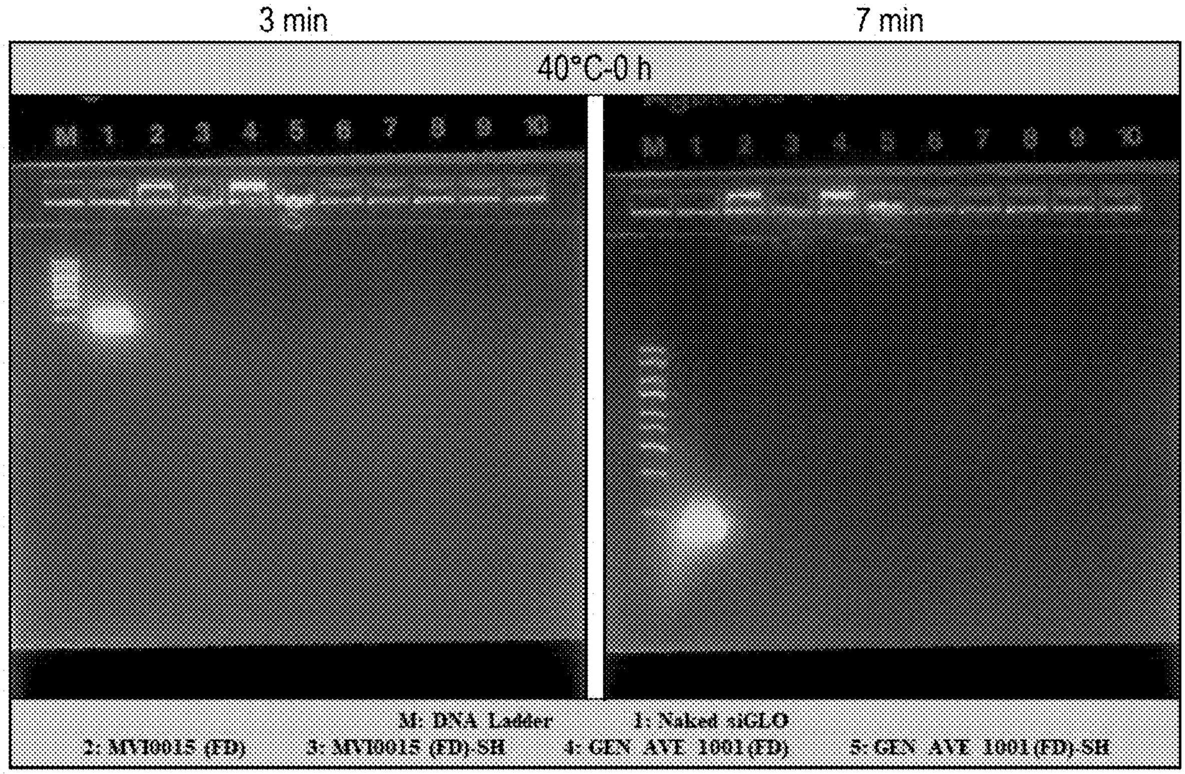
FIG. 23 Gel electrophoresis images of the siGLO-Delivery System complexes as resuspended freeze-dried powder (FD) or loaded on sodium hyaluronate (SH) hydrogels shortly after preparation.
Figure 24:
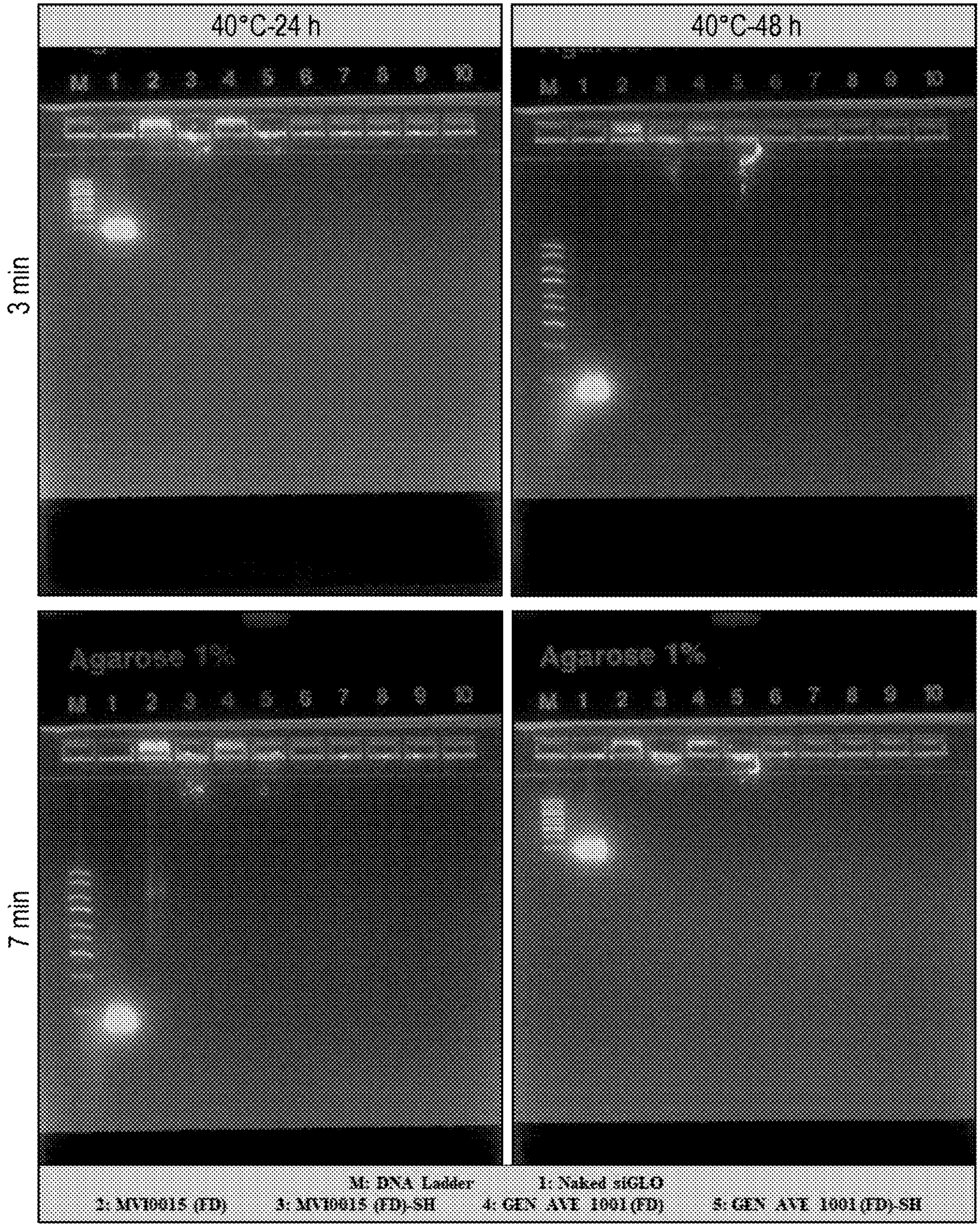
FIG. 24 Gel electrophoresis images of the siGLO-Delivery System complexes as resuspended freeze-dried powder (FD) or loaded on sodium hyaluronate (SH) hydrogels 24-48 after storage at 40° C.
Figure 25:
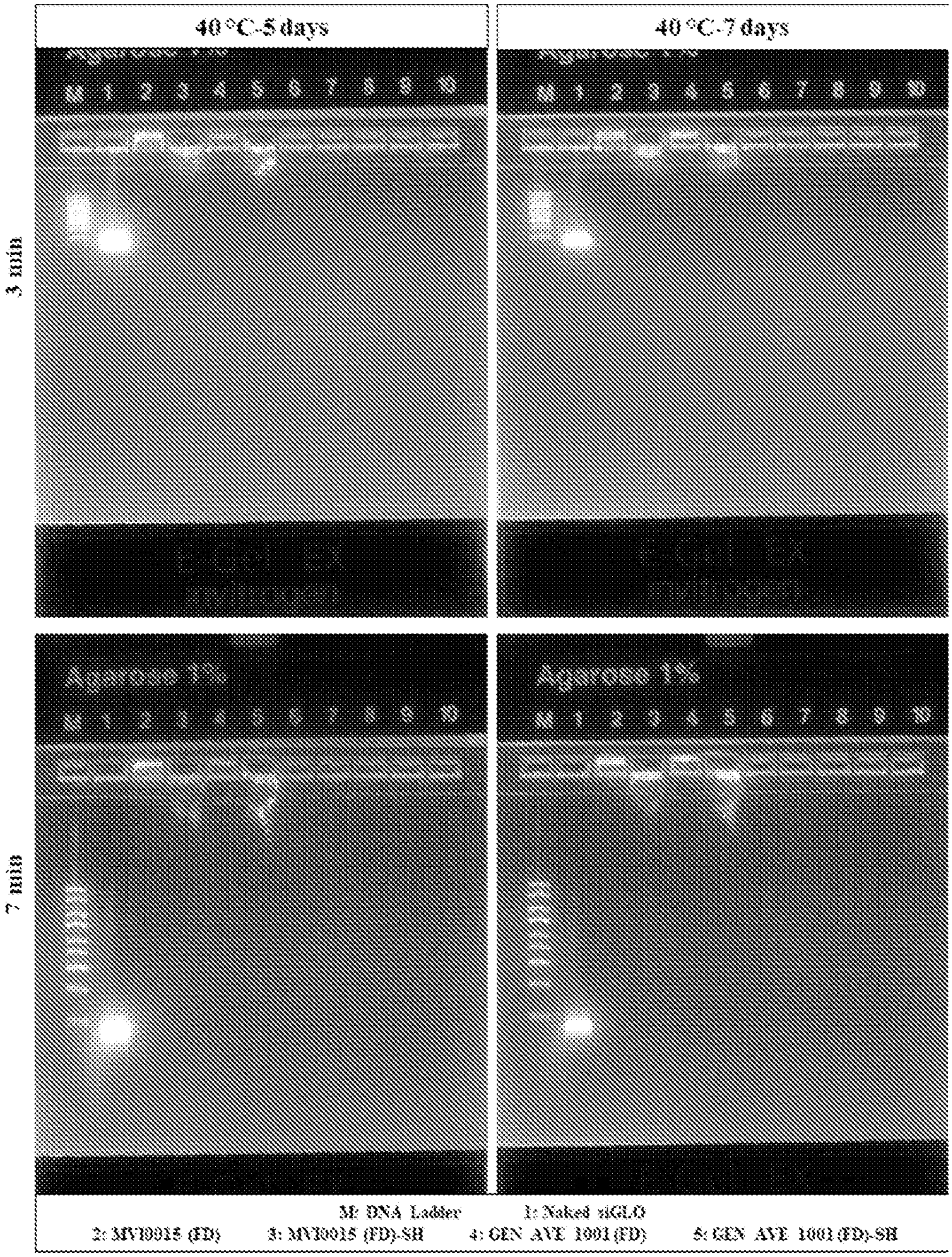
FIG. 25 Gel electrophoresis images of siGLO-Delivery System complexes as resuspended freeze-dried powder (FD) or loaded on sodium hyaluronate (SH) hydrogels 5 & 7 days after storage at 40° C.
Figure 26:
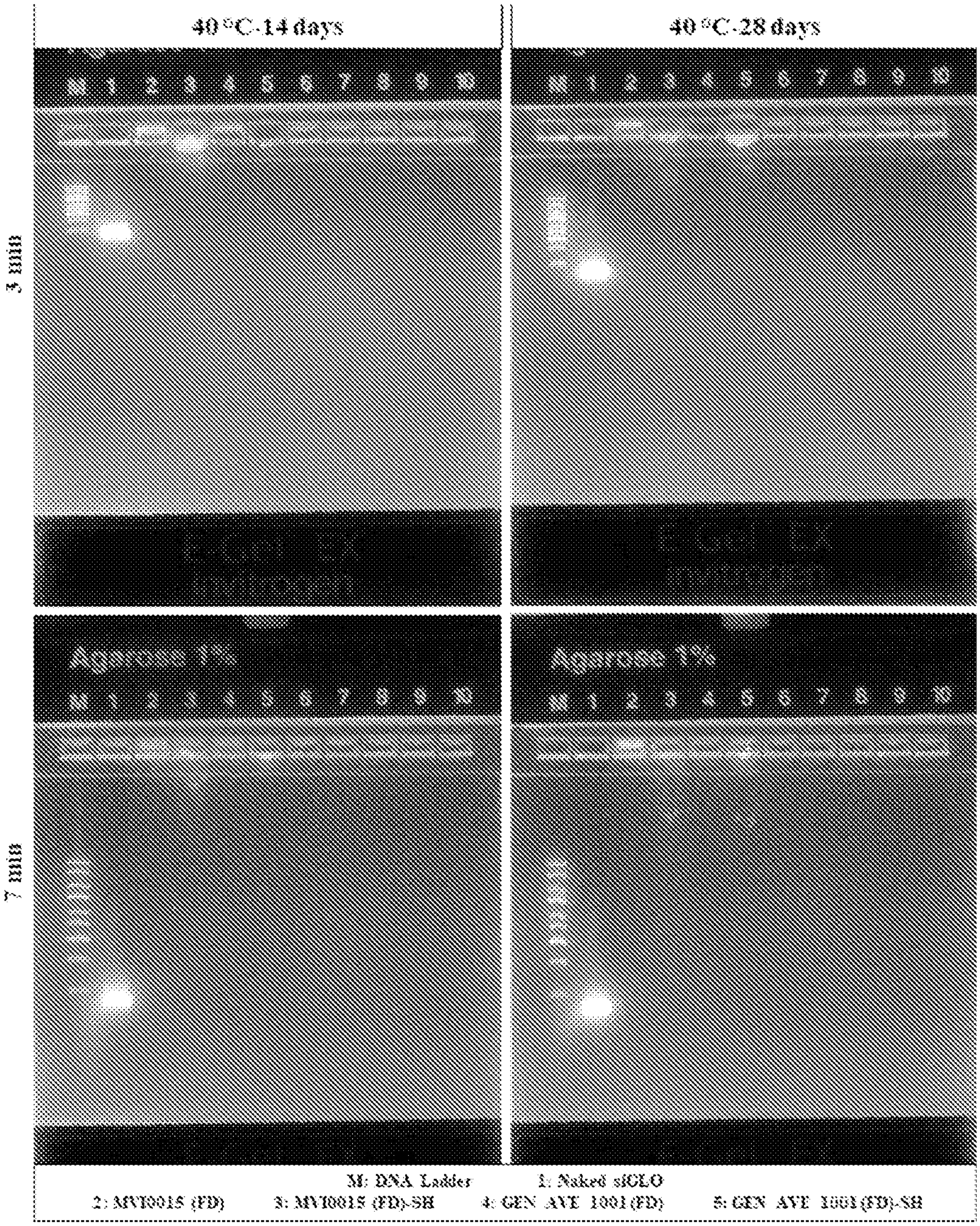
FIG. 26 Gel electrophoresis images of siGLO-Delivery System complexes as resuspended freeze-dried powder (FD) or loaded on sodium hyaluronate (SH) hydrogels 14 & 28 days after storage at 40° C.

The gel retardation images of SIS0013-biodegradable gel formulations loaded with either ADO2 siRNA or siGLO™ Green and stored at 40° C. are depicted in FIGS. 16 to 18. In a similar manner to the samples stored at room temperature, all the formulations appeared to be stable for 48 h indicated by lack of siRNA migration except the formulation in which the siRNA was first embedded into the hyaluronate biodegradable gel and then combined with the Delivery System. Fading of the signal for the siRNA associated with this formulation after 4 h indicates fast degradation of unbound siRNA at 40° C.

Observations

Loading siRNA onto SIS0012 and SIS0013 delivery system formulations mixed with sodium hyaluronate ranging from 1-2% or hypromellose 2-4% biodegradable gels with a lipid/siRNA weight ratio of 12 resulted in complete complexation of siRNA suggesting this ratio as the optimum ratio for complexation. The formulations were stable both at room temperature and at 40° C. for 48 h. For efficient mixing and complexation of siRNA with the delivery system, it is recommended to either mix the siRNA with the delivery system prior to embedding them into the biodegradable gel or mix the delivery system with the biodegradable gel prior to addition of siRNA. This approach will ensure homogenous dispersion of the siRNA in the mixture which would allow for complete complexation of the siRNA with the delivery system. There was no difference between the ADO-2 siRNA and the siGLO™ green in terms of complexation with the delivery system suggesting that siGLO™ green could be used as an alternative to ADO-2 siRNA for complexation and stability assays by gel electrophoresis.

Example 4

This experiment was carried out to provide validation of stabilisation data for siRNA as such or complexed with Bio-Courier delivery system embedded into gels, at various temperature (4° C., RT and 40° C.) using deliberately overloaded conditions agarose gel electrophoresis.

In order to reconfirm that the lack of detectable siRNA bands in previous studies (Examples 1, 2 and 3) is not due to the under-loading of the agarose gel well with RNA or the degradation of RNA on the edges of the well, the agarose gel well cell was deliberately overloaded with a siRNA amount of 2.6 μg/well.

siGLO was loaded onto different Biocourier formulations in liquid and freeze-dried form. The siGLO-Biocourier complexes embedded in hydrogels were examined at different storage temperatures using agarose gel electrophoresis.

Each well cell was overloaded with siRNA as such or complexed with the Bio-Courier delivery system. The aim of this experiment was to determine whether the absence of shearing or smearing bands of siRNA for the Bio-Courier delivery system complexed with biological species as such and/or embedded into the gel (experiments related to Example 1, 2 and 3) is not due to a low level detection of siRNA or eventual degradation of the biological species within the well but attributable to effectiveness of the binding offered by the presence of the solid particle system complexed with the biological species and embedding into the biodegradable gel.

Preparation of siRNA-Delivery System Complexes

The siRNA-delivery system formulations were prepared by mixing the Delivery System solution with the siRNA solution (0.66 mg/mL) at a weight ratio of 12:1. The mixtures were incubated at room temperature for 40 min to allow for complete complexation and then either used in the liquid form or freeze-dried overnight and then resuspended in nuclease free water. For the samples which were loaded on hydrogel, the freeze-dried powder was directly added to the hydrogel. The samples were split into 30 μL aliquots and stored at different temperatures (room temperature, 4° C. and 40° C.). At designated time points provided in Table 5 the samples were analyzed by gel electrophoresis.

TABLE 5

| | Storage | Measurement time point (days) | | | | | | |
|---|---|---|---|---|---|---|---|---|
| Formulation | temperature | 0 | 1 | 2 | 5 | 7 | 14 | 28 |
| MVI0015 (FD) | RT | ✓ | ✓ | ✓ | ✓ | ✓ | ✓ | ✓ |
| | 4° C. | ✓ | ✓ | ✓ | ✓ | ✓ | ✓ | ✓ |
| | 40° C. | ✓ | ✓ | ✓ | ✓ | ✓ | ✓ | ✓ |
| MVI0015 (Liq) | RT | ✓ | ✓ | ✓ | ✓ | ✓ | ✓ | ✓ |
| | 4° C. | ✓ | ✓ | ✓ | ✓ | ✓ | ✓ | ✓ |
| MVI0015 -SH | 40° C. | ✓ | ✓ | ✓ | ✓ | ✓ | ✓ | ✓ |
| GEN AVE1001 (FD) | RT | ✓ | ✓ | ✓ | ✓ | ✓ | ✓ | ✓ |
| | 4° C. | ✓ | ✓ | ✓ | ✓ | ✓ | ✓ | ✓ |
| | 40° C. | ✓ | ✓ | ✓ | ✓ | ✓ | ✓ | ✓ |
| GEN AVE1001 (Liq) | RT | ✓ | ✓ | ✓ | ✓ | ✓ | ✓ | ✓ |
| | 4° C. | ✓ | ✓ | ✓ | ✓ | ✓ | ✓ | ✓ |
| GEN AVE1001-SH | 40° C. | ✓ | ✓ | ✓ | ✓ | ✓ | ✓ | ✓ |

Agarose Gel Electrophoresis

The siGLO-delivery system complexes were analyzed by agarose gel electrophoresis using E-Gel™ agarose gel (1%) in the E-Gel™ Power Snap electrophoresis device. The naked siGLO stored at similar conditions was used as control in all cases. 20 μL of each sample (containing a total of 2.6 μg of siGLO) was loaded onto the agarose gel. For the control (naked siGLO) and the DNA ladder, 2 μL of the concentrated solution was diluted with 18 μL nuclease free water before loading on the agarose gel.

The gel was transilluminated and imaged at 3 min and 7 min using the E-Gel™ Power Snap electrophoresis camera.

Test 5. Validation of siRNA-Delivery System Complexes at Various Temperatures when Agarose Gel Well Overloaded with siRNA The gel electrophoresis images of the siGLO-delivery system complexes shortly after preparation are presented in FIGS. 19-26. For the freeze-dried formulations complete complexation was observed and no free siGLO was passing through the gel while for the liquid formulations some traces of siGLO were passing through the gels, indicating presence of some unbound siGLO. Nevertheless, the amounts of unbound siGLO were insignificant compared to the large amounts of siGLO loaded on the formulations.

The presence of a strong signal on the edges of all the wells suggests lack of siGLO degradation in any of the siGLO-delivery system complexes and stability of the formulations until 28 days under refrigerated and room temperature conditions. The only band didn't stay at the edge of the ladder of agarose gel was our control group, siRNA free form/siGLO, which travelled in the agarose gel as previously observed. The intensity of the band of naked siGLO, which was used as control, was very intensive and sharp band and well detectable confirming the system was working and able to show if there was any unbinding of siRNA-complex Drug Delivery. It is important to born in mind that due to very large amounts of siGLO loaded on the agarose gel which gives rise to a very strong signal, it would not be possible to detect small reductions in the signal caused by partial degradation of the naked siGLO, as observed in examples 1, 2 and 3, where the Gel assay was performed under non saturated conditions.

When formulations were exposed to 40° C., they proved to be also stable for up to 7 days and the presence of a strong signal in the edges of the wells indicated a lack of siGLO degradation. However, after 28 days, the signal from siGLO-GEN AVE1001 was not observed in the edge of well anymore suggesting degradation of siGLO while siGLO-MVI0015 still showed a fairly strong signal until 28 days.

Observations and General Remarks

The stabilisation of nucleic acid, mRNA and siRNA via incorporation within a delivery system comprising particles of biocompatible silicon ("Biocourier") has been demonstrated using an agarose gel electrophoresis assay. Binding of RNA with the complex remained stable at various temperatures indicating the complex is stable, without loss of binding over time. The embedding of the RNA-Biocourier complex in hydrogel improved the stability of RNA even further, which offers the potential to use RNA without the need for cold storage. Overloading the agarose gel well with siRNA as such or complexed with Biocourier confirmed the validity of the stabilisation data obtained for the RNA-Biocourier complex in hydrogel. When an agarose gel retardation assay was used under saturated conditions i.e. overloaded gel wells, the marked shearing or smearing bands, as previously reported in Experiments 1, 2 and 3, were again not observed. The absence of marked shearing or bands under saturated conditions was neither attributable to a degradation of the siRNA nor to lack of detectability of siRNA due to insufficient amounts of biological species complexed in the gel well but was due to the effectiveness of the binding offered by the Biocourier delivery system and the embedding of this system in a biodegradable gel. The effectiveness of the binding is illustrated by the intensity of the bands at the edges of the wells, which is similar to the intensity of the saturated naked siRNA control that migrated to the agarose gel wells.

Example 5—Investigation in Relation to Methicillin Resistant *Staphylococcus aureus* (MRSA)

The formulation set out in the following table was prepared, having a peptide as the API:

| Ingredients | Investigational Drug (proprietary peptide) | Si-NPs | Hydrogenated Phosphatidylcholine | Arginine | Glycine | Vitamin E |
|---|---|---|---|---|---|---|
| Amount | 20 mg | 4 mg | 8 mg | 400 ug | 200 ug | 200 ug |

To prepare the formulation, the lipid components were dissolved in methanol. Simultaneously, porous silicon nanoparticles (SiNPs) of 30 nm diameter (obtained from American Elements, CAS #7440-21-3, supplier code SI-E-0181M-NP100N) were dispersed in methanol and subsequently the solvent was evaporated in a slow evaporation process to yield the activated SiNPs. This activation step is aimed at rendering the SiNPs amenable to dispersion in water. The activated SiNPs were dispersed in nuclease-free water together with glycine and arginine and the peptide API.

After solvent evaporation, the lipid thin film was hydrated with the aqueous dispersion of functionalised SiNPs. The delivery system was then dispersed in a hydrogel, for which details are provided below. The prepared sample was refrigerated until further analysis.

- Formulation loaded with 0.11%; 0.33% or 1% w/w of peptide
- Embedded in 1% hypromellose hydrogel gel C: hypromellose 0.5%+pluronic 0.5%

In Vivo Analysis—Application to Human Skin

Figure 27:
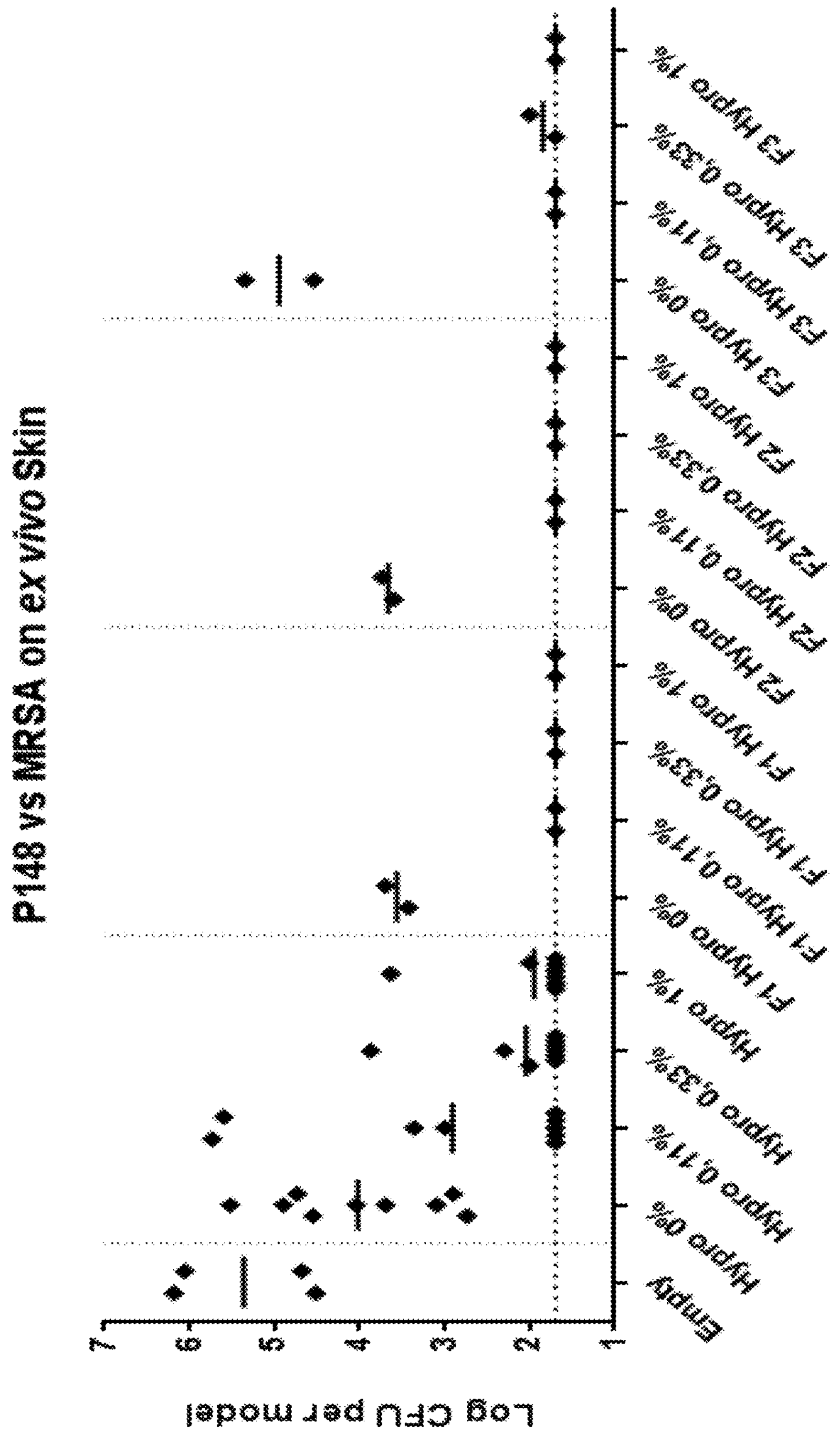
FIG. 27 Chart showing MRSA bacterial population on the skin of human volunteers following inoculation and treatment with peptide API in conventional chassis; loaded in formulations of the invention; or control (no peptide).

The skin of human volunteers was inoculated with 10 μl of $1\times10^7$ MRSA/ml suspension. After 1 hour incubation at 37° C. and 5% $CO_2$ with one of the following:

- Peptide (at varying concentrations, see FIG. 27) in hypromellose gel alone;
- Peptide (at varying concentrations, see FIG. 27) bound to the silicon-containing formulations of the present invention, with hypromellose gel;
- No peptide (control)

in a volume of 50 μl, was applied onto the inoculated skin. After an additional 1 h incubation, the numbers of viable bacteria determined microbiologically. Results are expressed as colony forming units (CFU). These results are shown in FIG. 27.

Further In Vivo Analysis—Application to Mouse Nasal Carriage

Figure 28:
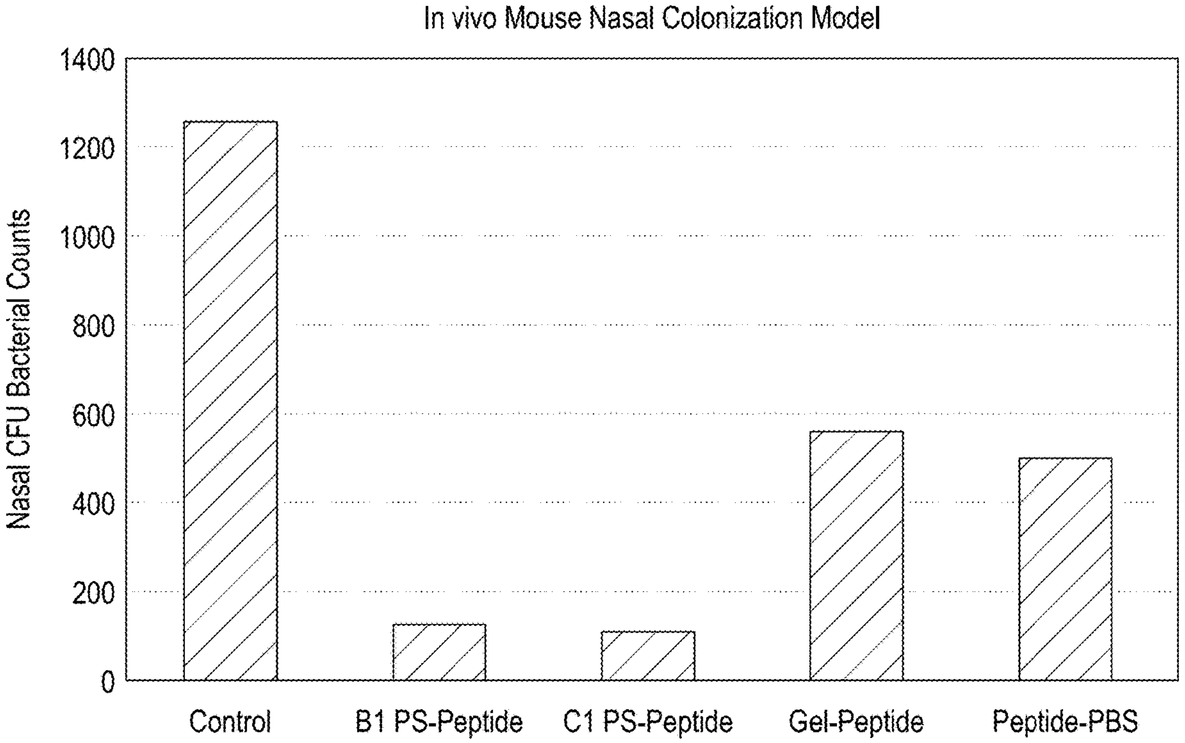
FIG. 28 Chart showing results of MRSA-Biofilm mouse nasal carriage model testing silicon-containing formulations.

An in vivo MRSA-Biofilm mouse nasal carriage model was used to test selected formulations, namely B1 PS-peptide and C1-PS peptide, aimed at reducing the MRSA bacterial load in the nasal passage. The proposed formulations aimed to stabilise the peptide at nasal pH and temperature, said stabilisation improving its activity against MRSA. As shown in FIG. 28, the formulations demonstrated enhanced performance at reducing MRSA bacterial counts >90%. The details of the formulations used are provided below.

Gel B1-Peptide: Formulation loaded with 1% of peptide bound to the silicon-containing formulation above, embedded in 1% Hypromellose hydrogel Gel C1-Peptide: Formulation loaded with 1% of peptide bound to the silicon-containing formulation above, embedded in Hypromellose 0.5%+Pluronic 0.5%

GEL-Peptide: Peptide at 1% concentration, embedded in 1% Hypromellose hydrogel

Peptide-PBS: Peptide at 1% concentration, embedded in 1% Hypromellose hydrogel

Example 6—Complexation of Further Silicon-Containing Formulations with mRNA or siRNA Alternatives were investigated to replace cationic lipids, such as DOTAP used in SIS0012 and SIS0013.

One such alternative is lipopeptides. These are amphiphiles that consist of a lipid chain (generally, 12-18 carbon-atoms long) conjugated to a peptide sequence (generally, of 3-20 amino acid residues). A particular example of such lipopeptides is palmitoyl pentapeptide-4 (abbreviated as PAL-KTTKS):

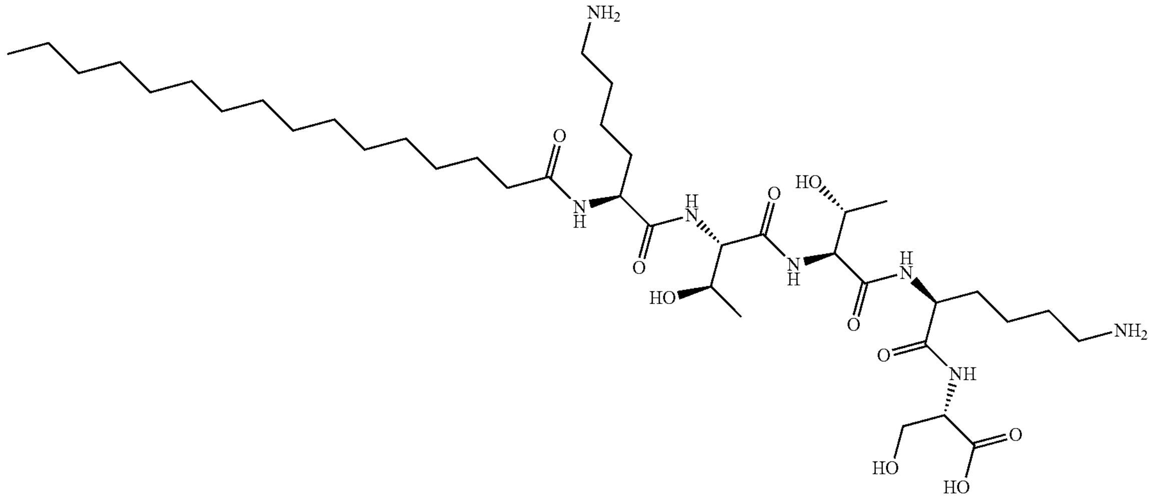

Palmitoyl pentapeptide-4

PAL-KTTKS is thought to be a good candidate for an alternative to cationic lipids, due to its cationic lysine residues, which assist binding to negatively charged RNA.

Other candidates investigated with SIS0012 and SIS0013 include NAD, tyrosine (TYR) and quercetin (QUE). With these ligands, it is thought that organ-specific uptake of RNA may be enhanced, and that cell internalisation and targeting may be improved. Moreover, they can assist in providing a positively charged environment for binding of negatively charged RNA.

Nicotinamide adenine dinucleotide (NAD) is a coenzyme. In its oxidised form, NAD+, it has the following structure:

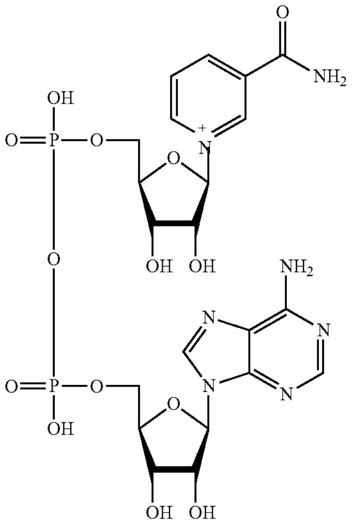

NAD+

Tyrosine is a naturally occurring amino acid, having the following structure at physiological pH (pH 7.4):

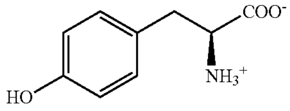

Tyrosine at physiological pH

Quercetin is a flavanol, having the following structure:

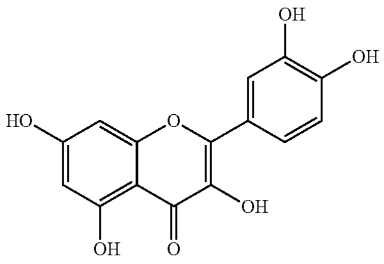

Quercetin

NAD, TYR and QUE—Investigation of Addition to, or Replacement of, DOTAP in SIS0012 and SIS0013

Figure 29:
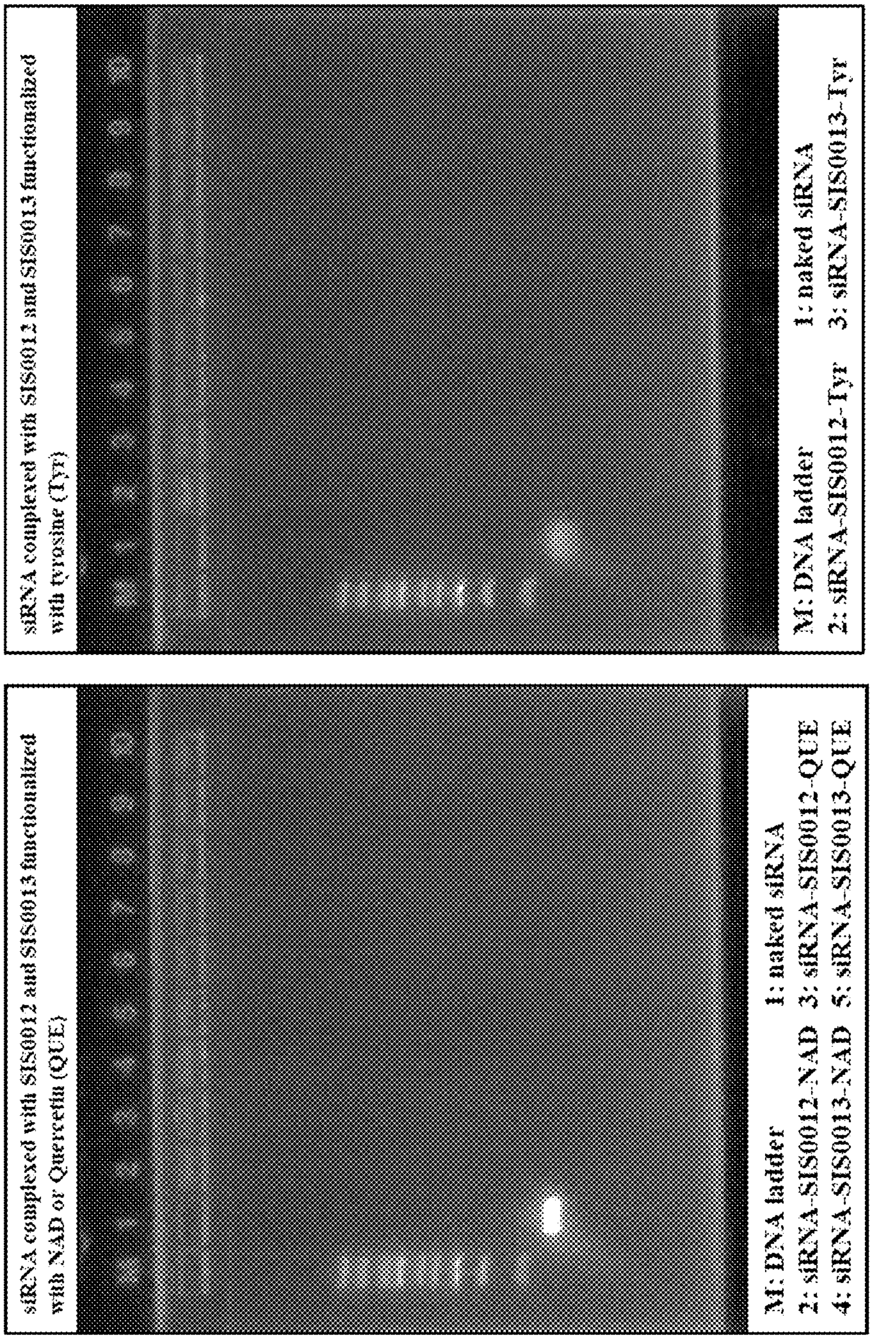
FIG. 29 shows gel electrophoresis images of SIS0012 and SIS0013 with NAD, TYR and QUE, when loaded with siRNA.

Modified SIS0012 and SIS0013 compositions were prepared by adding, to the usual compositions as set out above (i.e., in addition to DOTAP), 0.2 mg of NAD, TYR and QUE. Complexation with siRNA was then assessed. FIG. 29 shows gel electrophoresis results that indicate siRNA was successfully and fully bound in these formulations.

Dynamic light scattering measurements were also performed, using a Zetasizer (obtainable from Malvern Instruments) to assess size and charge, both prior to and following the formation of siRNA complexes, as shown in the table below. As the table indicates, size increases were observed after siRNA complexation, along with a 10-15 mV drop in surface charge.

| | Size (nm) | | PDI | | Zeta Potential (mV) | |
|---|---|---|---|---|---|---|
| Sample Code | Before Complexation | After Complexation | Before Complexation | After Complexation | Before Complexation | After Complexation |
| SIS0012-Empty | 119.0 ± 5.5 | 216.9 ± 1.5 | 0.22 ± 0.04 | 0.12 ± 0.01 | 58.3 ± 1.1 | 47.1 ± 0.5 |
| SIS0012 - NAD | 90.9 ± 1.3 | 186.0 ± 2.0 | 0.09 ± 0.02 | 0.25 ± 0.01 | 60.6 ± 1.0 | 42.7 ± 0.2 |
| SIS0012 - QUE | 91.6 ± 0.3 | 217.4 ± 2.5 | 0.07 ± 0.02 | 0.39 ± 0.01 | 63.2 ± 4.5 | 41.6 ± 0.2 |
| SIS0012 - TYR | 77.7 ± 0.5 | 334.0 ± 19.2 | 0.09 ± 0.01 | 0.45 ± 0.04 | 67.5 ± 1.1 | 44.8 ± 0.3 |
| SIS0013-Empty | 100.0 ± 0.4 | 165.8 ± 3.3 | 0.16 ± 0.03 | 0.19 ± 0.01 | 55.1 ± 1.4 | 46.9 ± 0.7 |
| SIS0013 - NAD | 104.8 ± 1.7 | 178.3 ± 1.5 | 0.09 ± 0.01 | 0.18 ± 0.01 | 58.5 ± 2.2 | 41.8 ± 0.3 |
| SIS0013 - QUE | 99.8 ± 0.3 | 175.2 ± 0.9 | 0.05 ± 0.01 | 0.25 ± 0.01 | 60.3 ± 0.8 | 43.3 ± 0.5 |
| SIS0013 - TYR | 94.2 ± 0.9 | 160.7 ± 1.1 | 0.09 ± 0.01 | 0.22 ± 0.01 | 64.6 ± 0.4 | 48.6 ± 0.4 |

The replacement of DOTAP by NAD, TYR or QUE (rather than simply addition of NAD, TYR or QUE to DOTAP-containing compositions) was then investigated.

For this study, DPPC and DOPE were selected for use alongside NAD, TYR or QUE, as DPPC and DOPE are zwitterionic lipids that play no significant role in surface charge at neutral pH.

Thus, DPPC/DOPE formulations were prepared with (i) 0.2 mg and (ii) 1 mg of NAD, TYR and QUE. The formulations are set out in the tables below.

TABLE

Composition of DPPC/DOPE LNP Biocourier functionalised with beta nicotinamide adenine dinucleotide (NAD).

| | Lipid phase | | Hydrating solution | | | | |
|---|---|---|---|---|---|---|---|
| Formulation | DPPC | DOPE | Activated siNPs (30 nm) | Glycine | Trehalose | NAD | NFW |
| DPPC/DOPE-NAD-0.2 mg | 7.75 mg | 8.25 mg | 1 mg | 0.5 mg | 1 mg | 0.2 mg | Up to 10 mL |
| DPPC/DOPE-NAD-1 mg | 7.75 mg | 8.25 mg | 1 mg | 0.5 mg | 1 mg | 1 mg | Up to 10 mL |

TABLE

Composition of DPPC/DOPE LNP Biocourier functionalised with Quercetin (QUE).

| | Lipid phase | | | Hydrating solution | | | |
|---|---|---|---|---|---|---|---|
| Formulation | DPPC | DOPE | Quercetin | Activated siNPs (30 nm) | Glycine | Trehalose | NFW |
| DPPC/DOPE-QUE-0.2 mg | 7.75 mg | 8.25 mg | 0.2 mg | 1 mg | 0.5 mg | 1 mg | Up to 10 mL |
| DPPC/DOPE-QUE-1 mg | 7.75 mg | 8.25 mg | 1 mg | 1 mg | 0.5 mg | 1 mg | Up to 10 mL |

TABLE

Composition of DPPC/DOPE LNP Biocourier SIS0012 functionalised with Tyrosine (TYR) solution

| | Lipid phase | | Hydrating solution | | | | |
|---|---|---|---|---|---|---|---|
| Formulation | DOTAP | DOPE | Activated SiNPs (30 nm) | Glycine | Trehalose | Tyrosine | NFW |
| DPPC/DOPE-TYR-0.2 mg | 7.75 mg | 8.25 mg | 1 mg | 0.5 mg | 1 mg | 0.2/1 mg | Up to 10 mL |
| DPPC/DOPE-TYR-1 mg | 7.75 mg | 8.25 mg | 1 mg | 0.5 mg | 1 mg | 0.2/1 mg | Up to 10 mL |

Zetasizer measurements were obtained, revealing negative zeta potentials across all formulations, irrespective of the amount of NAD, TYR or QUE; as shown in the table below.

TABLE

DPPC/DOPE LNPs functionalised with 0.2 mg and 1 mg of NAD, TYR and QUE.

| Sample | Size | PDI | Zeta-Empty |
|---|---|---|---|
| DPPC/DOPE-NAD-0.2 mg | 78.46 ± 2.65 | 0.18 ± 0.04 | −20.76 ± 0.68 |
| DPPC/DOPE-NAD-1 mg | 88.46 ± 1.22 | 0.16 ± 0.05 | −25.75 ± 0.57 |
| DPPC/DOPE-QUE-0.2 mg | 86.0 ± 0.63 | 0.17 ± 0.02 | −25.81 ± 0.82 |
| DPPC/DOPE-QUE-1 mg | 78.35 ± 2.19 | 0.18 ± 0.02 | −20.2 ± 1.43 |
| DPPC/DOPE-TYR-0.2 mg | 84.16 ± 2.33 | 0.19 ± 0.03 | −24.99 ± 0.44 |
| DPPC/DOPE-TYR-1 mg | 83.21 ± 2.57 | 0.16 ± 0.03 | −18.81 ± 0.46 |

Lipopeptides—Investigation of Replacement of DOTAP in SIS0012 and SIS0013

Also known as peptide amphiphiles (PA), lipopeptides were explored as another alternative to DOTAP.

It is thought that lipopeptides may offer a solution to the problem of replacing, or reducing the amount of, cationic lipids such as DOTAP, in transfection compositions. Lipopeptides consist of an alkyl chain conjugated to a peptide sequence. It is thought that their alkyl chain may be assimilated in lipid bilayers, while the surface of the bilayer is decorated with the peptide moiety.

An exemplary PA is the molecule palmitoyl pentapeptide-4 (abbreviated as PAL-KTTKS, see above). The two cationic lysine residues may perform a similar function to cationic lipid, such as DOTAP, exhibiting an electrostatic interaction with negatively charged RNA.

DPPC and DOPE were selected as neutral lipids to formulate with PAL-KTTKS. Various formulations were prepared with different silicon nanoparticles or without silicon at all; and with pH 4 buffer (to investigate the effect of pH).

Full details of the DPPC, DOPE and PAL-KTTKS-containing formulations are provided in the table below.

TABLE

Various formulation compositions of DPPC, DOPE and Pal-KTTKS with silicon nanoparticles, boron-doped silicon and boric acid/silicon nanoparticles. Formulation counterparts without silicon nanoparticles were also formulated as controls. All formulations were prepared up to 10 ml final volume.

| Sample | Lipids | | | Silicon-Trehalose-Glycine | | | Total lipid |
|---|---|---|---|---|---|---|---|
| Sample | DPPC | Lip-Peptide | DOPE | Silicon | Trehalose | Glycine | amount |
| 1- KTTKS-BC | 7.75 | 8.25 | 8.25 | 1 (Classic AE Si) | 1 | 0.5 | 24.25 |
| 2- KTTKS-BC | 8.25 | 7.75 | — | 1 (Classic AE Si) | 1 | 0.5 | 16 |
| 3- KTTKS-BC | 3.875 | 3.875 | 8.25 | 1 (Classic AE Si) | 1 | 0.5 | 16 |
| 4- KTTKS-BC | 7.75 | 8.25 | 8.25 | 1 (Boron doped Si) | 1 | 0.5 | 24.25 |
| 5- KTTKS-BC | 7.75 | 8.25 | 8.25 | 1 (Boric acid Si) | 1 | 0.5 | 24.25 |
| 6- KTTKS-BC pH 4 buffer | 7.75 | 8.25 | 8.25 | 1 (Classic AE Si) | 1 | 0.5 | 24.25 |
| 7- KTTKS-BC pH 4 buffer | 7.75 | 8.25 | 8.25 | — | — | — | 24.25 |
| 8- KTTKS-BC(Nuclease free water) | 7.75 | 8.25 | 8.25 | — | — | — | 24.25 |

All 8 formulations had positively charged surfaces, with zeta potentials (measured with a Zetasizer, obtainable from Malvern Instruments) provided in the table below.

Based on these results, it is thought that during assembly of the lipid film, PAL-KTTKS is arranges itself in the lipid bilayer with the peptide portion exposed on the nanoparticle surface. Furthermore, the lysine residues on that surface contribute to a positively charged formulation.

TABLE

Zeta potential measurements for all 8 DPPC/DOPE/PAL-KTTKS formulations.

| Sample | Zeta-Empty |
|---|---|
| 1-KTTKS-BC | 60.09 ± 0.84 |
| 2-KTTKS-BC | 48.48 ± 2.54 |
| 3-KTTKS-BC | 37.24 ± 0.63 |
| 4-KTTKS-BC | 54.38 ± 2.11 |
| 5-KTTKS-BC | 55.43 ± 1.11 |
| 6-KTTKS-BC pH 4 buffer | 59.44 ± 0.81 |
| 7-KTTKS-BC pH4 buffer | 55.51 ± 0.39 |
| 8-KTTKS-BC(Nuclease free water) | 53.11 ± 0.39 |

All formulations were assessed for their ability to electrostatically bind to siRNA and mRNA.

Figure 30:
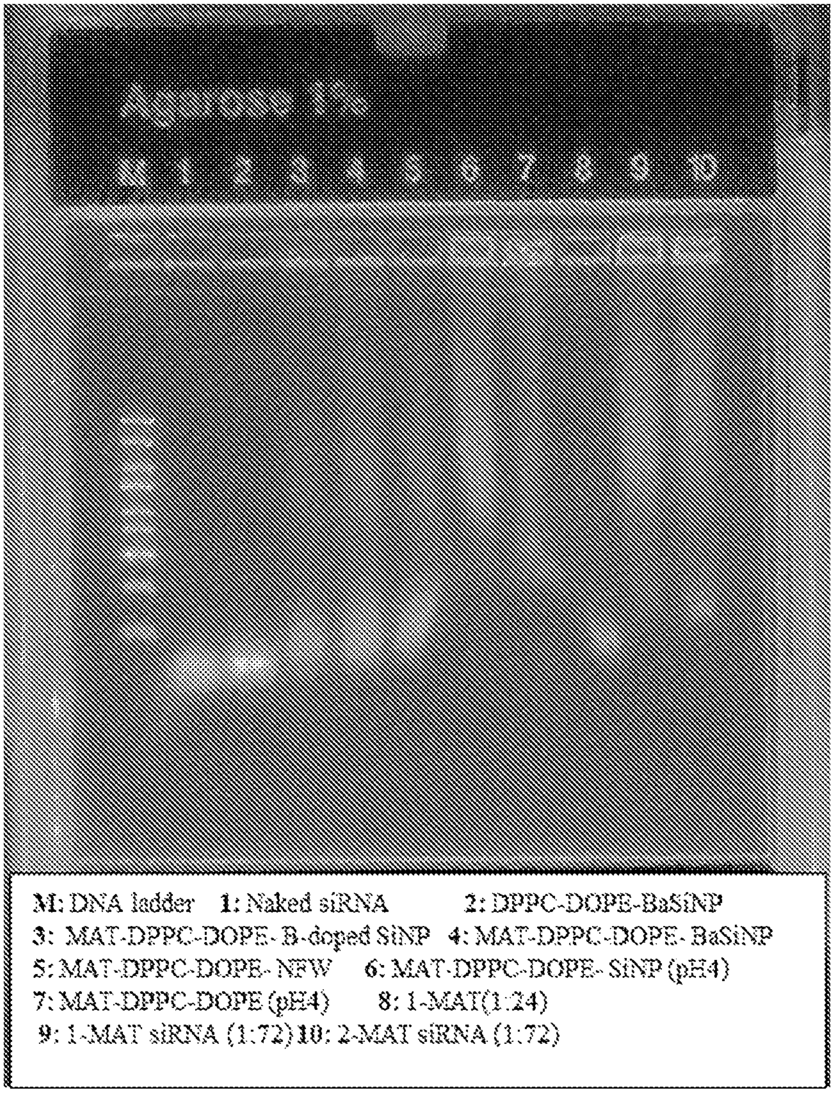
FIG. 30 shows a gel electrophoresis image of the DPPC/PAL-KTTKS-DOPE formulations of Example 6, when loaded with siRNA.
Figure 31:
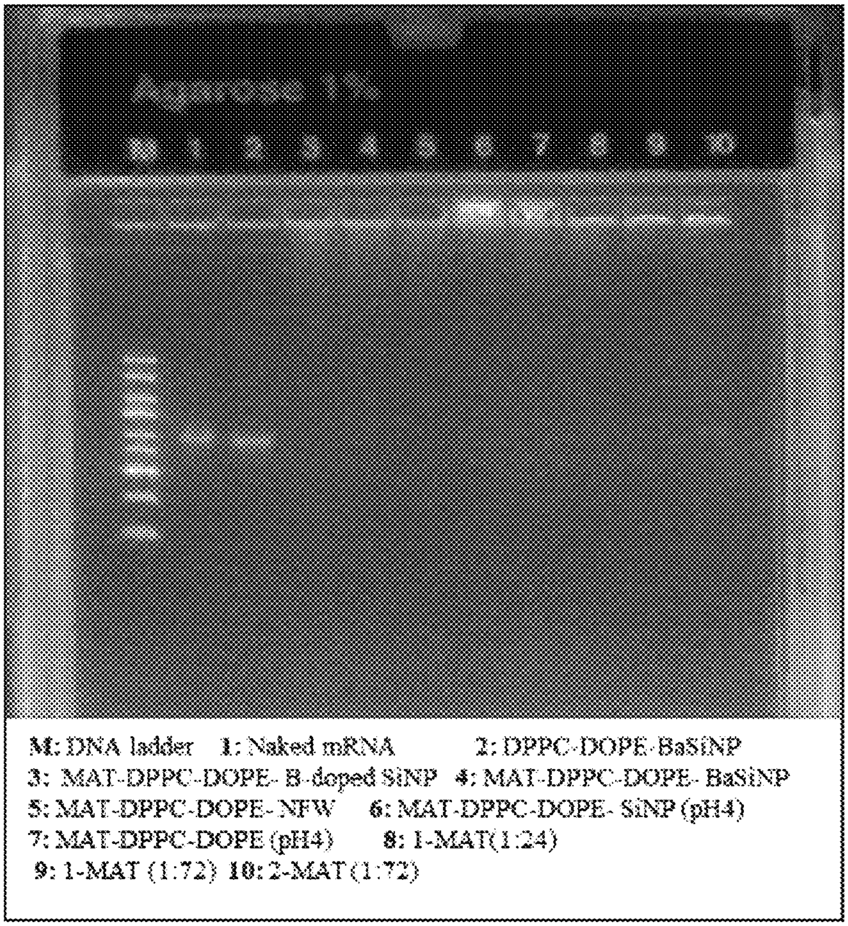
FIG. 31 shows a further gel electrophoresis image of DPPC/PAL-KTTKS-DOPE formulations of Example 6, when loaded with siRNA.

Gel electrophoresis analysis was performed. Full complexation was not observed for siRNA. However, full complexation was observed for mRNA. FIG. 30 shows the gel electrophoresis results for siRNA; FIG. 31 shows the gel electrophoresis results for mRNA.

Figure 32:
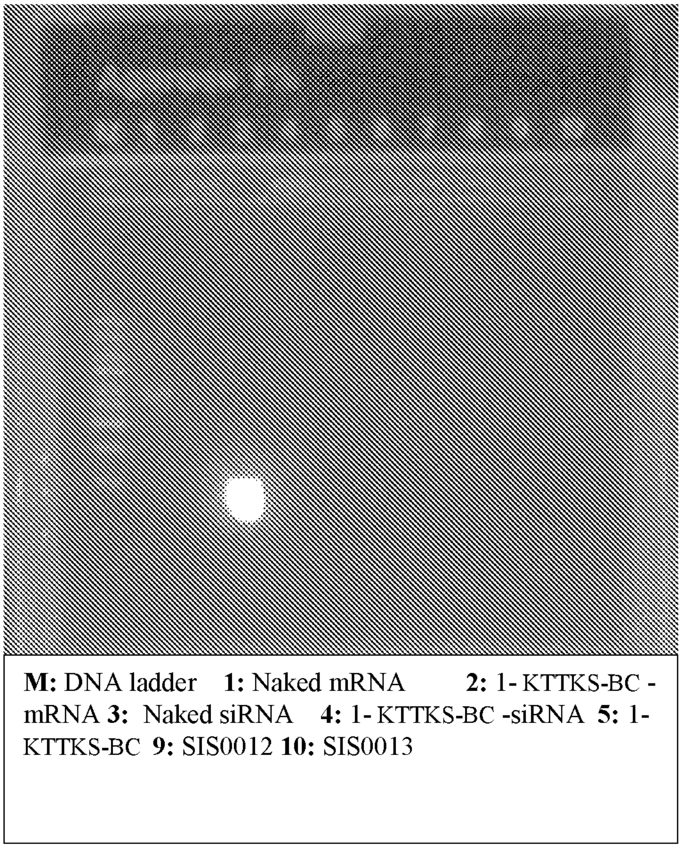
FIG. 32 shows a further gel electrophoresis image of DPPC/PAL-KTTKS-DOPE formulations of Example 6, when loaded with mRNA.

To address the partial complexation of siRNA with DPPC/DOPE/PAL-KTTKS, an alternative loading method was adopted. FIG. 32 shows gel electrophoresis of complexes after the alternative loading method was used, indicating successful complete complexation of siRNA. (The bright dot in lane 3 of FIG. 32 is an artefact of the imaging device.)

In the alternative loading method, compared to the protocol described hereinabove, the following steps were adopted:

1. A thin lipid film was prepared by dissolving DPPC, DOPE and Pal-KTTKS in methanol and evaporating using a rotary evaporator.
2. The lipid film was rehydrated with a suspension containing activated silicon (SIS0012) or activated boron-doped silicon (SIS0013) with trehalose and glycine as well as either siRNA or mRNA. Rehydration was performed at 40° C. for 10 mins to ensure no lipid-silicon film remained on the walls of the round bottomed rot-evap flask.

Lipopeptides are highly versatile molecules; they may be fine-tuned, by altering their alkyl chain and/or their peptide sequence. It is thought that customisation of the peptide may enhance cell and/or tissue targeting. In the field of gene therapy, customisation of the peptide may enhance electrostatic interactions with nucleic acids, such as RNA, particularly mRNA. As an example, PAL-KTTKS, when formulated with DPPC and DOPE, resulted in a positively charged surface, as confirmed by zeta potential.

Lipopeptides, being amphiphilic molecules, have very similar properties to surfactants, which can self-assemble to form micelles; it is thought that this is due at least in part to the alkyl chain being amenable to hydrophobic interactions, whilst the peptide sequence can form inter-molecular hydrogen bonding. Phospholipids, such as DPPC and DOPE, are also able to self-assemble into liposomes. Thus, when incorporating PAs, of which PAL-KTTKS is a representative example (although other lipopeptides may be used) the alkyl chain is able to form hydrophobic interactions with DPPC and DOPE leading to liposomal structures.

Meanwhile, the silicon nanoparticles provide structural stability for the complex as a whole, and are able to interact with the lipid and other ligands, such as lipopeptide, NAD, QUE or TYR, via non-covalent (electrostatic) interactions, thus promoting long-term stability and binding of nucleic acid.

The invention claimed is:

1. A method of preparing an injectable or oral storage stable formulation, comprising:

(i) contacting a biological species with a delivery system comprising (a) biocompatible solid particles that comprise hydrolysable silicon and (b) a lipid component comprising a cationic lipid and/or an ionisable lipid, to form a complex; then (ii) optionally, lyophilising the complex to form a powder; and then (iii) dispersing the complex in a biodegradable gel material to form the formulation, comprising the complex embedded in the biodegradable gel material.

2. The method of claim 1, wherein the delivery system further comprises a non-reducing disaccharide.

3. An injectable or oral storage stable formulation, comprising a biodegradable gel material in which is embedded a biological species complexed to a delivery system comprising biocompatible solid particles that comprise hydrolysable silicon, a lipid component comprising a cationic lipid and/or an ionisable lipid, and, optionally, a non-reducing disaccharide.

4. An injectable or oral storage stable formulation prepared according to the method of claim 1.

5. A method of preparing a medicament comprising a biological species for oral administration or administration by injection, the method comprising:

(i) providing a formulation in accordance with claim 3; then (ii) optionally, storing the formulation; and then (iii) preparing the medicament comprising the biological species and delivery system for oral administration or administration by injection, wherein the step (iii) of preparing the medicament does not include any extraction steps, such that the medicament comprises all the constituents of the formulation.

6. The method of claim 5 wherein in the step (ii) of storing the formulation, the formulation is stored at a temperature above 4° C. for at least 3 months.

7. An oral or injectable medicament obtained by the method of claim 5, either comprising: the biological species complexed with the delivery system, wherein the complex is embedded in a biodegradable gel material; or comprising: a complex of the biological species and the delivery system, together with compounds capable of forming the matrix of a biodegradable gel dispersed in a carrier system, wherein the delivery system comprises particles of hydrolysable silicon, a lipid component comprising a cationic lipid, and, optionally, a non-reducing disaccharide.

8. The medicament of claim 7, wherein the medicament is in the form of an injectable solution.

9. A method of treating or preventing a disease or disorder, the method comprising administering orally or by injection the medicament of claim 7 to a subject in need thereof.

10. A method of protecting a biological species from degradation, comprising:

(i) contacting the biological species with a delivery system comprising (a) biocompatible solid particles that comprise hydrolysable silicon and (b) a lipid component comprising a cationic lipid and/or an ionisable lipid, to form a complex; then (ii) optionally, lyophilising the complex to form a powder; and then (iii) dispersing the complex in a biodegradable gel material to form an oral or injectable formulation comprising the complex embedded in the biodegradable gel material.

11. The method of claim 10, wherein the delivery system further comprises a non-reducing disaccharide.

12. An injection device comprising the formulation of claim 3.

13. An oral dosage form comprising the formulation of claim 3.

14. The formulation of claim 3, wherein the delivery system comprises the non-reducing disaccharide trehalose.

15. The formulation of claim 3, wherein the biological species comprises one or more of: a nucleic acid, an antigen and a vaccine.

16. The formulation of claim 15, wherein the biological species comprises RNA or plasmid DNA; and, optionally, one or more enzymes.

17. The formulation of claim 3, wherein the lipid component further comprises a phospholipid and, optionally, a PEG-lipid and/or a structural lipid.

18. The formulation of claim 3, wherein the delivery system comprises an amino acid.

19. The formulation of claim 18, wherein the amino acid is selected from the group consisting of: arginine, histidine, lysine, proline and glycine.

20. The formulation of claim 19, wherein the amino acid is glycine or a combination of glycine with arginine or lysine.

21. The formulation of claim 18, wherein the lipid component is or comprises one or more phospholipids.

22. The formulation of claim 21, wherein the amino acid is tyrosine.

23. The formulation of claim 16, wherein the biological species comprises mRNA.

* * * * *